(12) United States Patent
Devita et al.

(10) Patent No.: US 11,547,712 B2
(45) Date of Patent: Jan. 10, 2023

(54) KINASE INHIBITOR COMPOUNDS AND COMPOSITIONS AND METHODS OF USE

(71) Applicant: ICAHN SCHOOL OF MEDICINE AT MOUNT SINAI, New York, NY (US)

(72) Inventors: Robert Devita, New York, NY (US); Andrew Stewart, New York, NY (US); Avner Schlessinger, New York, NY (US); Kunal Kumar, New York, NY (US); Peter Man-Un Ung, New York, NY (US); Hui Wang, New York, NY (US); Hailing Li, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 16/765,542

(22) PCT Filed: Nov. 20, 2018

(86) PCT No.: PCT/US2018/062023
§ 371 (c)(1),
(2) Date: May 20, 2020

(87) PCT Pub. No.: WO2019/100062
PCT Pub. Date: May 23, 2019

(65) Prior Publication Data
US 2020/0306257 A1 Oct. 1, 2020

Related U.S. Application Data

(60) Provisional application No. 62/588,792, filed on Nov. 20, 2017.

(51) Int. Cl.
*A61K 31/549* (2006.01)
*C07D 417/10* (2006.01)
*C07D 417/14* (2006.01)
*A61K 45/06* (2006.01)
*A61P 3/10* (2006.01)

(52) U.S. Cl.
CPC ............ *A61K 31/549* (2013.01); *A61K 45/06* (2013.01); *A61P 3/10* (2018.01); *C07D 417/10* (2013.01); *C07D 417/14* (2013.01)

(58) Field of Classification Search
CPC .. C07D 403/14; C07D 417/04; C07D 417/10; C07D 417/14
See application file for complete search history.

(56) References Cited

U.S. PATENT DOCUMENTS

| | | |
|---|---|---|
| 9,951,050 B2 | 4/2018 | Aberger et al. |
| 11,266,647 B2 | 3/2022 | Stewart et al. |
| 2004/0116474 A1 | 6/2004 | Munchhof et al. |
| 2004/0192583 A1 | 9/2004 | Medicherla et al. |
| 2005/0032869 A1 | 2/2005 | Berta et al. |
| 2007/0060619 A1 | 3/2007 | Burns et al. |
| 2007/0208053 A1 | 9/2007 | Arnold et al. |
| 2008/0221171 A1 | 9/2008 | Eberle et al. |
| 2009/0196912 A1 | 8/2009 | Eickhoff et al. |
| 2009/0312322 A1 | 12/2009 | Berg et al. |
| 2010/0173931 A1 | 7/2010 | Ellies et al. |
| 2010/0184758 A1 | 7/2010 | Dobbelaar et al. |
| 2010/0197562 A1 | 8/2010 | De Lera Ruiz et al. |
| 2011/0053930 A1 | 3/2011 | Yu et al. |
| 2011/0123651 A1 | 5/2011 | Mower et al. |
| 2012/0071512 A1 | 3/2012 | Hu et al. |

(Continued)

FOREIGN PATENT DOCUMENTS

| | | |
|---|---|---|
| CN | 102977096 A | 3/2013 |
| CN | 105884767 A | 8/2016 |

(Continued)

OTHER PUBLICATIONS

International Search Report and Written Opinion for corresponding Application No. PCT/US2018/062023 (dated Feb. 4, 2019).
Chunduru et al., "One-Pot Synthesis of 1,3,4-Thiadiazin-5-yl-chromen-2-one Derivatives via Three-Component Reaction," Synthetic Communications 42:1454-1460 (2011).
Kumar et al., "Novel Selective Thiadiazine DYRK1A Inhibitor Lead Scaffold with Human Pancreatic B-Cell Proliferation Activity," European Journal of Medicinal Chemistry 157:1005-1016 (2018).
PubmedCompound Summary for CID 17565749, "PNJQHHXWPZEHTA-UHFFFAOYSA-N," U.S. National Library of Medicine, pp. 1-10 (2007).

(Continued)

*Primary Examiner* — Susanna Moore
(74) *Attorney, Agent, or Firm* — Troutman Pepper Hamilton Sanders LLP (Rochester)

(57) ABSTRACT

The present invention is directed to kinase inhibitor compounds having the following structure: or a stereoisomer, pharmaceutically acceptable salt, oxide, or solvate thereof, where $R^1$, $R^2$, X, n, $R^3$, Y, Z, $R^4$, $R^5$, $R^6$, and = are as defined herein. The present invention also relates to compositions containing the kinase inhibitor compounds, methods of inhibiting activity of a kinase in a cell, methods of increasing cell proliferation in a population of pancreatic beta cells, methods of treating a subject for a condition associated with insufficient insulin secretion, and methods of treating a subject for a neurological disorder.

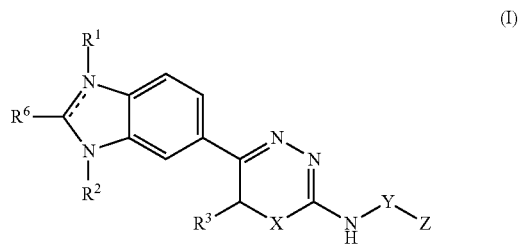

17 Claims, 5 Drawing Sheets

(56) References Cited

U.S. PATENT DOCUMENTS

| | | |
|---|---|---|
| 2013/0023491 A1 | 1/2013 | Annes et al. |
| 2013/0102627 A1 | 4/2013 | Higgins et al. |
| 2013/0210060 A1 | 8/2013 | Hosoya et al. |
| 2014/0275064 A1 | 9/2014 | Leblond et al. |
| 2014/0288068 A1 | 9/2014 | Ellies et al. |
| 2015/0174034 A1 | 6/2015 | Hu et al. |
| 2015/0266878 A1 | 9/2015 | Yang et al. |
| 2015/0297573 A1 | 10/2015 | Dalle et al. |
| 2016/0038500 A1 | 2/2016 | Klein et al. |
| 2016/0039845 A1 | 2/2016 | Wang et al. |
| 2016/0122361 A1 | 5/2016 | Reddy et al. |
| 2016/0186143 A1 | 6/2016 | Melton et al. |
| 2016/0289315 A1 | 10/2016 | Mirza et al. |
| 2017/0056379 A1 | 3/2017 | Chen et al. |
| 2017/0280720 A1 | 10/2017 | Chesworth et al. |
| 2017/0281607 A1 | 10/2017 | Davies |
| 2018/0216076 A1 | 8/2018 | Hebrok et al. |
| 2019/0328738 A1 | 10/2019 | Stewart et al. |
| 2021/0032601 A1 | 2/2021 | Stewart et al. |
| 2021/0094950 A1 | 4/2021 | Kumar et al. |
| 2022/0064146 A1 | 3/2022 | Devita et al. |
| 2022/0162182 A1 | 5/2022 | Devita et al. |

FOREIGN PATENT DOCUMENTS

| | | |
|---|---|---|
| GB | 2447791 A | 9/2008 |
| WO | 2010/123583 A2 | 10/2010 |
| WO | 2010/137350 A1 | 12/2010 |
| WO | 2011/075665 A2 | 6/2011 |
| WO | 2011/133795 A2 | 10/2011 |
| WO | 2011/133882 A1 | 10/2011 |
| WO | 2011/133888 A1 | 10/2011 |
| WO | 2011/161256 A1 | 12/2011 |
| WO | 2012/024433 A2 | 2/2012 |
| WO | 2013/119518 A1 | 8/2013 |
| WO | 2014/004857 A1 | 1/2014 |
| WO | 2014/058080 A1 | 4/2014 |
| WO | 2014/063477 A1 | 5/2014 |
| WO | 2014/202638 A1 | 12/2014 |
| WO | 2014/203217 A1 | 12/2014 |
| WO | 2015/011331 A1 | 1/2015 |
| WO | 2015/058031 A1 | 4/2015 |
| WO | 2015/157093 A1 | 10/2015 |
| WO | 2017040993 A1 | 3/2017 |
| WO | 2017/085198 A1 | 5/2017 |
| WO | 2017/106630 A1 | 6/2017 |
| WO | 2017/117556 A1 | 7/2017 |
| WO | 2017/168245 A1 | 10/2017 |
| WO | 2017/197151 A1 | 11/2017 |
| WO | 2018/081401 A1 | 5/2018 |
| WO | 2018/083157 A1 | 5/2018 |
| WO | 2018/098561 A1 | 6/2018 |
| WO | 2019/136320 A1 | 7/2019 |
| WO | 2019/183245 A1 | 9/2019 |
| WO | 2020/142485 A1 | 7/2020 |
| WO | 2020/142486 A1 | 7/2020 |

OTHER PUBLICATIONS

Extended European Search Report in corresponding Application No. 18878625.5 (dated Feb. 23, 2021).
Office Action in Europe Application No. 17863636.1, dated Jan. 12, 2021.
Wang et al., "Diabetes Mellitus—Advances and Challenges in Human β-Cell Proliferation," Nat. Rev. Endocrinol. 11(4):201-212 (2015).
EP Search Report and Opinion for EP Application No. 178636361. 1, dated May 6, 2020.
Shen et al., "Inhibition of DYRK1A and GSK3B induces human β-cell proliferation," Nature Comm. 6:8372 (2015).
Madhu et al., "Dual Inhibition of Activin/Nodal/TGF-β and BMP Signaling Pathways by SB431542 and Dorsomorphin Induces Neuronal Differentiation of Human Adipose Derived Stem Cells," Stem Cells Int. 1-13 (2016).
Vogt et al.,"The Specificities of Small Molecule Inhibitors of the TGFβ and BMP Pathways," Cell. Signal. 23(11):1831-1842 (2011).
Wang et al., "Combined Inhibition of DYRK1A, SMAD, and Trithorax Pathways Synergizes to Induce Robust Replication in Adult Human Beta Cells," Cell Metab. 29(3):638-652 (2019).
Nassar et al. "A TGF-Beta Receptor 1 Inhibitor for Prevention of Proliferative Vitreoretinopathy," Experimental Eye Research, 2014, vol. 123, pp. 72-86 (Year: 2014).
Wang et al., "A High-throughput Chemical Screen Reveals That Harmine-Mediated Inhibition of DYRK1A Increases Human Pancreatic Bela Cell Replication," Nature Medicine 21(4):383-388 (2015).
Huynh et al., "Screening and Identification of a Novel Class of TGF-[beta] Type 1 Receptor Kinase Inhibitor," Journal of Biomolecular Screening 16(7):724-733 (2011).
Dhawan et al., "Inhibition of TGF-beta Signaling Promotes Human Pancreatic Bela Cell Replication," Diabetes 65(5):1208-1218 (2016).
Pagliuca et al., "Generation of Functional Human Pancreatic [beta] Cells In Vitro," Cell 159(2):428-439 (2014).
PCT International Search Report and Opinion for corresponding PCT/US2017/058498, dated Jan. 9, 2018.
Xiao et al., "Resveratrol Attenuates Renal Injury and Fibrosis by Inhibiting Transforming Growth Factor β Pathway on Matrix Metalloproteinase 7," Experimental Biology and Medicine, Jan. 2016, vol. 241, pp. 140-146. (Year: 2016).
Office Action in Europe Application No. 17863636.1, dated Oct. 22, 2021.
Restriction Requirement in U.S. Appl. No. 16/344,230 (dated Feb. 6, 2020).
Office Action in U.S. Appl. No. 16/344,230 (dated May 4, 2020).
Office Action in U.S. Appl. No. 16/344,230 (dated Nov. 2, 2020).
Office Action in U.S. Appl. No. 16/344,230 (dated Apr. 13, 2021).
International Search Report and Written Opinion for International Application No. PCT/2019/012442 (dated Apr. 24, 2019).
Shah et al., "The DPP-4 Inhibitor Linagliptin Restores Beta-Cell Function and Survival in Human Isolated Islets through GLP-1 Stabilization," J. Clin. Endocrinol. Metabol. 98(7):1163-1172 (2013).
Navarro et al., "Genetic Disruption of Adenosine Kinase in Mouse Pancreatic Beta-Cells Protects Against High-Fat Diet-Induced Glucose Intolerance," Diabetes 66(7):928-1938 (2017).
Supplementary European Search Report and Written Opinion in EP 19735846.8 (dated Aug. 18, 2021).
Kumar et al., "Development of Kinase-Selective, Harmine-Based DYRK1A Inhibitors that Induce Pancreatic Human β-Cell Proliferation," J. Med. Chem. 61(17):7687-7699 (2018) [Author Manuscript].
Amisten et al., "An Atlas and Functional Analysis of G-Protein Coupled Receptors in Human Islets of Langerhans," Pharmacology & Therapeutics 139:359-391 (2013).
Zhao et al., "Repurposing cAMP-Modulating Medications to Promoate β-Cell Replication," Mol. Endocrinol. 28(10):1682-1697 (2014).
Reimann & Gribble, "G Protein-Coupled Receptors as New Therapeutic Targets for Type 2 Diabetes," Diabetologica 59:229-233 (2016).
Bachem, "Peptides for Diabetes Research," Peptides and Diabetes, published by Global Marketing Bachem Group (2017).
Nance et al., "Discovery of a Novel Series of Orally Bioavailable and CNS Penetrant Glucagon-Like Peptide-1 Receptor (GLP-1R) Noncompetitive Antagonists Based on a 1,3-Disubstituted-7-Aryl-5,5-Bis(Trifluoromethyl)-5,8-Dihydropyrimido[4,5-d]Pyrimidine-2,4(1H,3H)-Dione Core," J. Med. Chem. 60:1611-1616 (2017).
Restriction Requirement in U.S. Appl. No. 16/959,390 (dated Nov. 1, 2021).
International Search Report and Written Opinion for PCT/US2019/023206, dated Jul. 29, 2019.
Ishida et al., "Antitumor Agents 201. Cytotoxicity and B-Carboline Analogs," Bioorg. Med. Chem. Lett. 9:3319-3324 (1999).
International Search Report and Written Opinion for International Application No. PCT/US2019/069057 (dated Mar. 9, 2020).
Multhoff et al., "Chronic Inflammation in Cancer Development," Front. Immunol. 2(98):1-17 (2012).

(56) References Cited

OTHER PUBLICATIONS

International Search Report and Written Opinion for PCT/US2019/069059, dated Mar. 9, 2020.
Dirice, E., et al., "Inhibition of DYRK1A Stimulates Human beta-Cell Proliferation," Diabetes, 65:1660-1671 (2016).
Pubchem CID 53496098, pp. 1-9 (2011).
Pubchem CID 116977135, pp. 1-7 (2016).
Pubchem CID 84152473, pp. 1-7 (2104).
Pubchem CID 66793828, pp. 1-9 (2012).
Pubchem CID 20199687, pp. 1-9 (2007).
Pubchem CID 68046670, pp. 1-8 (2012).
Pubchem CID 76281619, pp. 1-10 (2014).
Tahtouh et al., "Selectivity, Cocrystal Structures, and Neuroprotective Properties of Leucettines, a Family of Protein Kinase Inhibitors Derived from the Marine Sponge Alkaloid Leucettamine B," J. Med. Chem. 55:9312-9330 (2012).
Rosselot et al., "Human Beta Cell Mass Expansion in Vivo with a Harmine and Extendin-4 Combination: Quantification and Visualization by iDISCO+ 3D Imaging," bioRxiv preprint (2021).
Supplementary Partial European Search Report and Opinion in EP Application No. 19771612.9, dated Dec. 20, 2021.
Balint et al., "Structure-Based Design and Synthesis of Harmine Derivatives with Different Selectivity Profiles in Kinase versus Monoamine Oxidase Inhibition," ChemMedChem. 12(12):932-939 (2017).
Drung et al., "Computational & Experimental Evaluation of the Structure/Activity Relationship of β-Carbolines as DYRK1A Inhibitors," Bioorg. Med. Chem. Lett. 24(20):4854-4860 (2014).
Yadav and Nandi, "QSAR and Anticancer Drug Design of β-Carboline Compounds Utilizing Computed Molecular Descriptors," Journal of Computational Methods in Molecular Design 4(3):92-105 (2014).
Frederick et al., "Novel Trisubstituted Harmine Derivatives with Original in Vitro Anticancer Activity," J. Med. Chem. 55(14):6489-6501 (2012).
Cuny et al., "Structure-Activity Relationship Study of Beta-Carboline Derivatives as Haspin Kinase Inhibitors," Bioorg. Med. Chem. Lett. 22(5):2015-2019 (2012) [Author Manuscript].
Filali et al., "Synthesis of New Harmine Isoxazoles and Evaluation of their Potential Anti-Alzheimer, Anti-inflammatory, and Anticancer Activities," Med. Chem. 12(2):184-190 (2016).
Filali et al., "Synthesis of New Isoxazoline Derivatives from Harmine and Evaluation of their Anti-Alzheimer, Anti-Cancer and Antiinflammatory Activities," 30(3):371-376 (2015).
European Search Report and Opinion in EP Application No. 19771612.9, dated Mar. 22, 2022.
International Search Report and Written Opinion International Application No. PCT/US21/39132 (dated Dec. 7, 2021).
Gupta et al., "Models for the Prediction of Receptor Tyrosine Kinase Activity of Substituted 3-Aminoindazole Analogues," Sci. Pharm 79:239-257 (2011).
Pubchem SID 194152017, pp. 1-7 (2014).
Pubchem SID 245038163, pp. 1-7 (2015).
Bresson et al., "Anti-CD3 and Nasal Proinsulin Combination Therapy Enhances Remission from Recent-Onset Autoimmune Diabetes by Inducing Tregs," J. Clin. Invest. 116(5):1371-1381 (2006).
Herold et al., "An Anti-CD3 Antibody, Teplizumab, in Relatives at Risk for Type 1 Diabetes," N. Engl. J. Med. 381:603-613 (2019).
Sims et al., "Teplizumab Improves and Stabilizes Beta Cell Function in Antibody Positive High-Risk Individuals," Sci. Transl. Med. 13(583):eabc8980 (2021) [Author Manuscript].
Heagopian et al., "Teplizumab Preserves C-Peptide in Recent-Onset Type 1 Diabetes: Two-Year Results from the Randomized, Placebo-Controlled Protégé Trial," Diabetes 62(11):3901-3908 (2013).
Herold et al., "Teplizumab (Anti-CD3 mAb) Treatment Preserves C-Peptide Responses in Patients With New-Onset Type 1 Diabetes in a Randomized Control Trial: Metabolic and Immunologic Features at Baseline Identify a Subgroup of Responders," Diabetes 62(11):3766-3774 (2013).
Sherry et al., "Teplizumab for Treatment of Type 1 Diabetes (Protege Study): 1 Year Results from a Randomised, Placebo-Controlled Trial," Lancet 378:487-497 (2011).
Bluestone et al., "Immunotherapy: Building A Bridge to a Cure for Type 1 Diabetes," Science 373:510-516 (2021).
Von Herrath et al., "Anti-lnterieukin-21 Antibody and Liraglutide for the Preservation of β-Cell Function in Adults with Recent-Onset Type 1 Diabetes: A Randomised, Double-Blind, Placebo-Controlled, Phase 2 Trial," Lancet Diabetes Endocrinol. 9:212-224 (2021).
Office Action in U.S. Appl. No. 16/959,390 (dated Mar. 30, 2022).
Office Action in JP 2020-527899 (drafted Oct. 20, 2022).
"5-(2-Benzylimino-3,6-dihydro-1,3,4-thiadiazin-5-yl)-1,3-dihydrobenzimidazol-2-one," Web page <https://pubchem.ncbi.nlm.nih.gov/compound/135783279>, 11 pages, Jan. 17, 2019, retrieved from <https://pubchem.ncbi.nlm.nih.gov/compound/135783279> on Oct. 24, 2022.
European Search Report and Opinion in EP Application No. 19907897.3, dated Sep. 12, 2022.
Gupta et al., "Synthesis of 4-Aryl and Unsymmetrical 4,6-Diarylpyrimidines by the Suzuki-Miyaura Cross-Coupling Reaction," Heterocycles 96(9):1549-1569 (2018).
Coombs et al., "Small-Molecule Pyrimidine Inhibitors of the CDC2-Like (Clk) and Dual Specificity Tyrosine Phosphorylation-Regulated (Dyrk) Kinases: Development of Chemical Probe ML315," Bioorganic & Medicinal Chemistry Letters 23(12):3654-3661 (2013) [Author Manuscript].
European Search Report and Opinion in EP Application No. 19907044.2, dated Aug. 5, 2022.
Pu et al., "Design, Synthesis and Biological Evaluation of Indole Derivatives as Vif Inhibitors," Bioorganic & Medicinal Chemistry Letters 27(17):4150-4155 (2017).
Office Action in U.S. Appl. No. 16/959,390 (dated Sep. 15, 2022).
Examination Report in EP Application No. 17863636.1, dated Aug. 11, 2022.

KINASE INHIBITOR COMPOUNDS AND COMPOSITIONS AND METHODS OF USE

This application is a national stage application under 35 U.S.C § 371 of PCT International Application Serial No. PCT/US2018/062023, filed Nov. 20, 2018, which claims the priority benefit of U.S. Provisional Patent Application Ser. No. 62/588,792, filed Nov. 20, 2017, which are hereby incorporated by reference in their entirety.

This invention was made with government support under grant number DK015015 and DK116904 awarded by the National Institutes of Health. The government has certain rights in the invention.

FIELD OF THE INVENTION

The present invention relates to kinase inhibitor compounds and compositions and methods of use thereof.

BACKGROUND OF THE INVENTION

The Dual-Specificity Tyrosine-Regulated kinases ("DYRKs") belong to the CMCG family of eukaryotic protein kinases which include the CDK-like kinases (CLKs), Glycogen Synthase Kinase 3 (GSK3), Cyclin Dependent Kinases (CDKs), and Mitogen-Activated Protein Kinases (MAPKs). DYRK family proteins self-activate by autophosphorylation of the conserved tyrosine residue in the activation loop, then subsequently phosphorylate substrates only on serine and threonine residues (Lochhead et al., "Activation-Loop Autophosphorylation is Mediated by a Novel Transitional Intermediate Form of DYRKs," *Cell* 121(6): 925-936 (2005); Walte et al., "Mechanism of Dual Specificity Kinase Activity of DYRK1A," *FEBS J.* 280(18):4495-4511 (2013); and Becker et al., "Activation, Regulation, and Inhibition of DYRK1A," *FEBS J.* 278(2):246-256 (2011)). The DYRK family consists of five subtypes, including 1A, 1B, 2, 3 and 4. Among them, DYRK1A is the most extensively studied subtype. It is ubiquitously expressed and has been shown to play an important role in brain development and function (Becker et al., "DYRK1A: A Potential Drug Target for Multiple Down Syndrome Neuropathologies," *CNS Neurol. Disord.: Drug Targets* 13(1):26-33 (2014)), neurodegenerative diseases (Wegiel et al., "The Role of DYRK1A in Neurodegenerative Diseases," *FEBS J.* 278(2): 236-245 (2011) and Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012)), tumorigenesis, apoptosis (Ionescu et al., "DYRK1A Kinase Inhibitors With Emphasis on Cancer," *Mini-Rev. Med. Chem.* 12(13):1315-1329 (2012) and Fernandez-Martinez et al., "DYRK1A: The Double-Edged Kinase as a Protagonist in Cell Growth and Tumorigenesis," *Mol. Cell. Oncol.* 2(1):e970048 (2015)), and human pancreatic β-cell proliferation (Wang et al., "A High-Throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," *Nat. Commun.* 6:8372 (2015); Rachdi et al., "Dyrk1A Induces Pancreatic β Cell Mass Expansion and Improves Glucose Tolerance," *Cell Cycle* 13(14):2221-2229 (2014); and Dirice et al., "Inhibition of DYRK1A Stimulates Human Beta-Cell Proliferation," *Diabetes* 65:(6):1660-1671 (2016)).

Regulated expression of DYRK1A during fetal, postnatal life, as well as in adults, is essential for normal neuronal development and brain function. DYRK1A is located in the Down Syndrome Critical region ("DSCR") on human chromosome 21, a genomic region that has an important role in pathogenesis of Down Syndrome ("DS"), one of the most common and frequent human genetic disorders (Becker et al., "Activation, Regulation, and Inhibition of DYRK1A," *FEBS J.* 278(2):246-256 (2011) and Becker et al., "Structural and Functional Characteristics of Dyrk, a Novel Subfamily of Protein Kinases With Dual Specificity," *Prog. Nucleic Acid Res. Mol. Biol.* 62:1-17 (1999)). Overexpression of DYRK1A in mouse and *Drosophila* models mimics the neurodevelopmental abnormalities associated with DS (Becker et al., "DYRK1A: A Potential Drug Target for Multiple Down Syndrome Neuropathologies," *CNS Neurol. Disord.: Drug Targets* 13(1):26-33 (2014); Wegiel et al., "The Role of DYRK1A in Neurodegenerative Diseases," *FEBS J.* 278(2):236-245 (2011); Park et al., "Function and Regulation of Dyrk1A: Towards Understanding Down Syndrome," *Cell. Mol. Life Sci.* 66(20):3235-3240 (2009); and Ogawa et al., "Development of a Novel Selective Inhibitor of the Down Syndrome-Related Kinase Dyrk1A," *Nat. Commun.* 1: Article Number 86 (2010)). Recent evidences has also implicated DYRK1A in the tau dysfunction and tau pathology of Alzheimer's disease ("AD"), dementia with Lewy bodies, and Parkinson's disease (Wegiel et al., "The Role of DYRK1A in Neurodegenerative Diseases," *FEBS J.* 278(2):236-245 (2011); Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012); and Stotani et al., "DYRK1A Inhibition as Potential Treatment for Alzheimer's Disease," *Future Med. Chem.* 8(6):681-696 (2016)). It has been reported that DYRK1A is overexpressed in various tumors such as, ovarian cancer, colon cancer, lung cancer, and pancreatic cancer, signifying its role in tumorigenesis and uncontrolled cell proliferation (Ionescu et al., "DYRK1A Kinase Inhibitors With Emphasis on Cancer," *Mini-Rev. Med. Chem.* 12(13):1315-1329 (2012) and Fernandez-Martinez et al., "DYRK1A: The Double-Edged Kinase as a Protagonist in Cell Growth and Tumorigenesis," *Mol. Cell. Oncol.* 2(1):e970048 (2015)). Inhibition of DYRK1A leads to destabilized EGFR and reduced EGFR-dependent tumor growth in glioblastoma (Pozo et al., "Inhibition of DYRK1A Destabilizes EGFR and Reduces EGFR-Dependent Glioblastoma Growth," *J. Clin. Invest.* 123(6):2475-2487 (2013)). Also, DYRK1A inhibition induces activation of caspase-9 which leads to massive apoptosis in specific cancer cell types (Seifert et al., "DYRK1A Phosphorylates Caspase 9 at an Inhibitory Site and is Potently Inhibited in Human Cells by Harmine," *FEBS J.* 275(24):6268-6280 (2008)). Recently, DYRK1A has been shown to be involved in molecular pathways relevant to human β-cell proliferation, making it a potential therapeutic target for β-cell regeneration in Type 1 and Type 2 diabetes (Wang et al., "A High-throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," *Nat. Commun.* 6:8372 (2015); Rachdi et al., "Dyrk1A Induces Pancreatic β Cell Mass Expansion and Improves Glucose Tolerance," *Cell Cycle* 13(14):2221-2229 (2014); and Dirice et al., "Inhibition of DYRK1A Stimulates Human Beta-cell Proliferation," *Diabetes* 65:(6):1660-1671 (2016)). DYRK1A inhibition has been proposed to drive β-cell proliferation by inducing translocation of the nuclear factor of activated T cells ("NFAT") family of transcription factors to the nucleus, allowing access to the promoters of genes which subsequently activate human β-cell proliferation (Wang et al., "A High-throughput Chemical Screen Reveals That Harmine-Mediated Inhibition of DYRK1A Increases Human Pancreatic Beta Cell Replication," *Nat. Med.* 21(4):383-388 (2015) and Rachdi et al., "Dyrk1A Induces Pancreatic β Cell Mass Expansion and Improves Glucose Tolerance," *Cell Cycle* 13(14):2221-2229 (2014)).

Because of its involvement in neurodegenerative disease, cancer, and diabetes, DYRK1A has attracted increasing interest as a potential therapeutic target. A significant amount of work has been carried out to not only understand its underlying role in diseases, but also in identifying novel DYRK1A inhibitors (Becker et al., "Activation, Regulation, and Inhibition of DYRK1A," *FEBS J.* 278(2):246-256 (2011); Becker et al., "DYRK1A: A Potential Drug Target for Multiple Down Syndrome Neuropathologies," *CNS Neurol. Disord.: Drug Targets* 13(1):26-33 (2014); Wegiel et al., "The Role of DYRK1A in Neurodegenerative Diseases," *FEBS J.* 278(2):236-245 (2011); Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012); Ionescu et al., "DYRK1A Kinase Inhibitors with Emphasis on Cancer," *Mini-Rev. Med. Chem.* 12(13):1315-1329 (2012); Fernandez-Martinez et al., "DYRK1A: The Double-Edged Kinase as a Protagonist in Cell Growth and Tumorigenesis," *Mol. Cell. Oncol.* 2(1):e970048 (2015); Wang et al., "A High-throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," Nat. Commun. 6:8372 (2015); and Dirice et al., "Inhibition of DYRK1A Stimulates Human Beta-cell Proliferation," *Diabetes* 65:(6):1660-1671 (2016)).

Several DYRK1A inhibitors from natural sources as well as small molecule drug discovery programs have been identified and characterized. Among all the DYRK1A inhibitors, harmine and its analogues (β-carbolines) are the most commonly studied and remain the most potent and orally bioavailable class of inhibitors covered to date (Becker et al., "Activation, Regulation, and Inhibition of DYRK1A," *FEBS J.* 278(2):246-256 (2011) and Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012)).

Apart from harmine, EGCg and other flavan-3-ols (Guedj et al., "Green Tea Polyphenols Rescue of Brain Defects Induced by Overexpression of DYRK1A," *PLoS One* 4(2):e4606 (2009) and Bain et al., "The Specificities of Protein Kinase Inhibitors: An Update," *Biochem. J.* 371(1):199-204 (2003)), leucettines (Tahtouh et al., "Selectivity, Cocrystal Structures, and Neuroprotective Properties of Leucettines, a Family of Protein Kinase Inhibitors Derived from the Marine Sponge Alkaloid Leucettamine B," *J. Med. Chem.* 55(21):9312-9330 (2012) and Naert et al., "Leucettine L41, a DYRK1A-preferential DYRKs/CLKs Inhibitor, Prevents Memory Impairments and Neurotoxicity Induced by Oligomeric Aβ25-35 Peptide Administration in Mice," *Eur. Neuropsychopharmacol.* 25(11):2170-2182 (2015)), quinalizarin (Cozza et al., "Quinalizarin as a Potent, Selective and Cell-permeable Inhibitor of Protein Kinase CK2," *Biochem. J* 421(3):387-395 (2009)), peltogynoids Acanilol A and B (Ahmadu et al, "Two New Peltogynoids from *Acacia nilotica* Delile with Kinase Inhibitory Activity," *Planta Med.* 76(5):458-460 (2010)), benzocoumarins (dNBC) (Sarno et al., "Structural Features Underlying the Selectivity of the Kinase Inhibitors NBC and dNBC: Role of a Nitro Group that Discriminates Between CK2 and DYRK1A," *Cell. Mol. Life Sci.* 69(3):449-460 (2012)), and indolocarbazoles (Staurosporine, rebeccamycin and their analogues) (Sanchez et al., "Generation of Potent and Selective Kinase Inhibitors by Combinatorial Biosynthesis of Glycosylated Indolocarbazoles," *Chem. Commun.* 27:4118-4120 (2009), are other natural products that have been shown to inhibit DYRK1A and other kinases.

Among the other scaffolds identified from small molecule drug discovery attempts, INDY (Ogawa et al., "Development of a Novel Selective Inhibitor of the Down Syndrome-Related Kinase Dyrk1A," *Nat. Commun.* 1: Article Number 86 (2010)), DANDY (Gourdain et al., "Development of DANDYs, New 3,5-Diaryl-7-Azaindoles Demonstrating Potent DYRK1A Kinase Inhibitory Activity," *J. Med. Chem.* 56(23):9569-9585 (2013)), and FINDY (Kii et al., "Selective Inhibition of the Kinase DYRK1A by Targeting its Folding Process," *Nat. Commun.* 7:11391 (2016)), pyrazolidine-diones (Koo et al., "QSAR Analysis of Pyrazolidine-3,5-Diones Derivatives as Dyrk1A Inhibitors," *Bioorg. Med. Chem. Lett.* 19(8):2324-2328 (2009); Kim et al., "Putative Therapeutic Agents for the Learning and Memory Deficits of People with Down Syndrome," *Bioorg. Med. Chem. Lett.* 16(14):3772-3776 (2006)), amino-quinazolines (Rosenthal et al., "Potent and Selective Small Molecule Inhibitors of Specific Isoforms of Cdc2-Like Kinases (Clk) and Dual Specificity Tyrosine-Phosphorylation-Regulated Kinases (Dyrk)," *Bioorg. Med. Chem. Lett.* 21(10):3152-3158 (2011)), meriolins (Giraud et al., "Synthesis, Protein Kinase Inhibitory Potencies, and In Vitro Antiproliferative Activities of Meridianin Derivatives," *J. Med. Chem.* 54(13):4474-4489 (2011); Echalier et al., "Meriolins (3-(Pyrimidin-4-yl)-7-Azaindoles): Synthesis, Kinase Inhibitory Activity, Cellular Effects, and Structure of a CDK2/Cyclin A/Meriolin Complex," *J. Med. Chem.* 51(4):737-751 (2008); and Akue-Gedu et al., "Synthesis and Biological Activities of Aminopyrimidyl-Indoles Structurally Related to Meridianins," *Bioorg. Med. Chem.* 17(13):4420-4424 (2009)), pyridine and pyrazines (Kassis et al., "Synthesis and Biological Evaluation of New 3-(6-hydroxyindol-2-yl)-5-(Phenyl) Pyridine or Pyrazine V-Shaped Molecules as Kinase Inhibitors and Cytotoxic Agents," *Eur. J Med. Chem.* 46(11):5416-5434 (2011)), chromenoidoles (Neagoie et al., "Synthesis of Chromeno[3,4-b]indoles as Lamellarin D Analogues: A Novel DYRK1A Inhibitor Class," *Eur. J Med. Chem.* 49:379-396 (2012)), 11H-indolo[3,2-c]quinoline-6-carboxylic acids, 37 thiazolo[5,4-f]quinazolines (EHT 5372) (Foucourt et al., "Design and Synthesis of Thiazolo[5,4-f] quinazolines as DYRK1A Inhibitors, Part I," *Molecules* 19(10):15546-15571 (2014) and Coutadeur et al., "A Novel DYRK1A (Dual Specificity Tyrosine Phosphorylation-Regulated Kinase 1A) Inhibitor for the Treatment of Alzheimer's Disease: Effect on Tau and Amyloid Pathologies In Vitro," *J Neurochem.* 133(3):440-451 (2015)), and 5-iodotubercidin (Dirice et al., "Inhibition of DYRK1A Stimulates Human Beta-cell Proliferation," *Diabetes* 65:(6):1660-1671 (2016) and Annes et al., "Adenosine Kinase Inhibition Selectively Promotes Rodent and Porcine Islet β-cell Replication," *Proc. Natl. Acad. Sci.* 109(10):3915-3920 (2012)) showed potent DYRK1A activity with varying degrees of kinase selectivity.

Most of these compounds are non-selective inhibitors of DYRK1A and exhibit pharmacological side effects, such as CNS activity or apoptosis, thereby limiting their therapeutic utility and potential for pharmaceutical development. This non-selectivity may be attributed to the fact that all these DYRK1A inhibitors are Type I kinase inhibitors, which bind to a highly conserved ATP binding pocket.

The present invention is directed to overcoming deficiencies in the art.

SUMMARY OF THE INVENTION

One aspect of the present invention relates to a compound of formula (I) having the following structure:

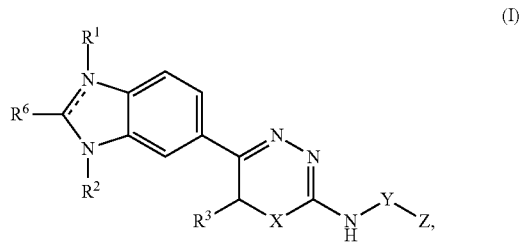

(I)

or a stereoisomer, pharmaceutically acceptable salt, oxide, or solvate thereof, where
  $R^1$ is optionally present;
  $R^1$, when present, and $R^2$ are independently selected at each occurrence thereof from H, $CH_3$, $CF_3$, halogen, and cyano;
  X is selected from S, SO, and $SO_2$;
  n is an integer selected from 1 and 2;
  $R^3$ is selected from H, D, halogen, and $C_1$-$C_6$ substituted or unsubstituted alkyl;
  Y is selected from a bond and branched on linear $C_1$-$C_6$ substituted or unsubstituted alkyl;
  Z is selected from substituted or unsubstituted aryl, heteroaryl, cycloalkyl, alkyl, and heterocycle, ether, amine, and sulfonyl;
  $R^4$ is independently selected at each occurrence thereof from H, $C_1$-$C_6$ alkyl, halogen, and —$OR^5$;
  $R^5$ is selected from H and $C_1$-$C_6$ alkyl;
  $R^6$ is optionally present, and when present is a carbonyl or $C_1$-$C_1$ alkyl; and
  === is a single or double bond, with the proviso that when $R^1$ and $R^2$ are both H, n is 1, $R^3$ is H, X is S, and Y is $CH_2$, then Z cannot be phenyl.

Another aspect of the present invention relates to a method of inhibiting activity of a kinase in a cell. This method involves contacting the cell with a compound of formula (I) of the present invention under conditions effective to inhibit activity of the kinase in the cell.

A further aspect of the present invention relates to a method of increasing cell proliferation in a population of pancreatic beta cells. This method involves contacting a population of pancreatic beta cells with a compound of formula (I) according to the present invention under conditions effective to increase cell proliferation in the population of pancreatic beta cells.

Another aspect of the present invention relates to a composition comprising a compound of formula (I) according to the present invention and a carrier.

An additional aspect of the present invention relates to a method of treating a subject for a condition associated with insufficient insulin secretion. This method involves administering to a subject in need of treatment for a condition associated with an insufficient level of insulin secretion a compound or composition of the present invention.

A further aspect of the present invention relates to a method of treating a subject for a neurological disorder. This method involves administering to a subject in need of treatment for a neurological disorder a compound of formula (I) according to the present invention under conditions effective to treat the subject for the condition.

Although efforts have been made toward the discovery of potent and selective DYRK1A inhibitors, most of them are still in early stages of lead identification.

Described herein infra is the identification and evaluation of a highly potent and novel class of thiadiazine analogue inhibitors.

DETAILED DESCRIPTION OF THE INVENTION

Figure 1:
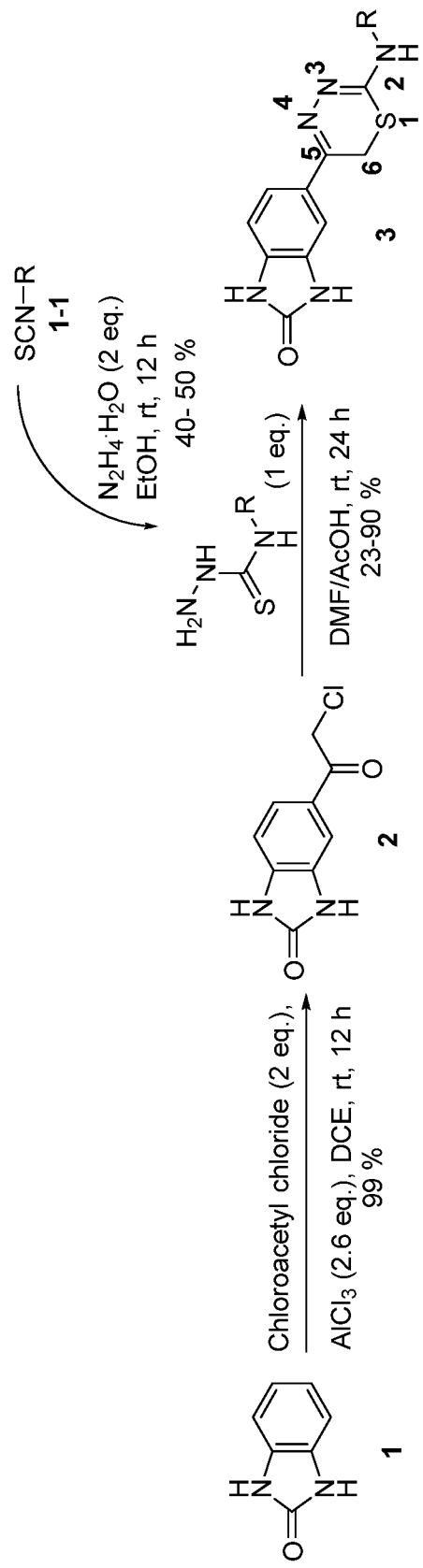
FIG. 1 is a schematic illustration showing the synthesis of 1,3,4-thiadiazine compounds. Acylation of commercially available 2-hydroxybenzimidazole with chloroacetyl chloride in the presence of $AlCl_3$ gave compound 2 in 95% yield. Subsequently, α-chloro ketone 2 underwent smooth cyclo-condensation with purchased or synthesized thiosemicarbazides containing various R-groups to afford the desired thiadiazine analogues in a range of 23-90% yield.

The present invention relates to kinase inhibitor compounds and compositions and methods of their use.

One aspect of the present invention relates to a compound of formula (I) having the following structure:

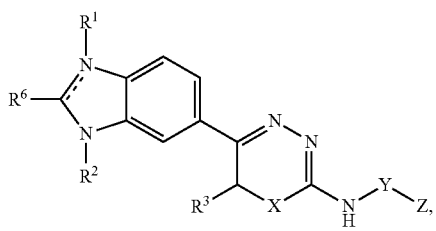

(I)

or a stereoisomer, pharmaceutically acceptable salt, oxide, or solvate thereof, where
R$^1$ is optionally present;
R$^1$, when present, and R$^2$ are independently selected at each occurrence thereof from H, CH$_3$, CF$_3$, halogen, and cyano;
X is selected from S, SO, and SO$_2$;
n is an integer selected from 1 and 2;
R$^3$ is selected from H, D, halogen, and C$_1$-C$_6$ substituted or unsubstituted alkyl;
Y is selected from a bond and branched on linear C$_1$-C$_6$ substituted or unsubstituted alkyl;
Z is selected from substituted or unsubstituted aryl, heteroaryl, cycloalkyl, alkyl, and heterocycle, ether, amine, and sulfonyl;
R$^4$ is independently selected at each occurrence thereof from H, C$_1$-C$_6$ alkyl, halogen, and —OR$^5$;
R$^5$ is selected from H and C$_1$-C$_6$ alkyl;
R$^6$ is optionally present, and when present is a carbonyl or C$_1$-C$_1$ alkyl; and
=== is a single or double bond, with the proviso that when R$^1$ and R$^2$ are both H, n is 1, R$^3$ is H, X is S, and Y is CH$_2$, then Z cannot be phenyl.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs.

As used herein, the term "halogen" means fluoro, chloro, bromo, or iodo.

The term "alkyl" means an aliphatic hydrocarbon group which may be straight or branched having about 1 to about 6 carbon atoms in the chain (or the number of carbons designated by "CG-CG", where n is the numerical range of carbon atoms). Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic, saturated or unsaturated, mono- or multi-cyclic ring system of about 3 to about 7 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl." Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-TH-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocycle" refers to a stable 3- to 18-membered ring (radical) of carbon atoms and from one to five heteroatoms selected from nitrogen, oxygen, and sulfur. The heterocycle may be a monocyclic or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The phrases "substituted or unsubstituted" and "optionally substituted" mean a group may (but does not necessarily) have a substituent at each substitutable atom of the group (including more than one substituent on a single atom), and the identity of each substituent is independent of the others.

The term "substituted" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture and formulation into an efficacious therapeutic agent.

By "compound(s) of the invention" and equivalent expressions, it is meant compounds herein described, which expression includes the prodrugs, the pharmaceutically acceptable salts, the oxides, and the solvates, e.g. hydrates, where the context so permits.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. All tautomeric forms are also intended to be included.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed by the present invention.

The term "pharmaceutically acceptable salt" refers to salts prepared from pharmaceutically acceptable non-toxic acids or bases including inorganic acids and bases and organic acids and bases.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

In one embodiment of the compound of formula (I), $R^1$ and $R^2$ are H;

X is S;

N is 1;

$R^3$ is H; and $R^4$ is H.

In accordance with this embodiment, Z may be an unsubstituted phenyl ring or a phenyl ring substituted with a halogen, —$CF_3$, a nitrile, or —$CONH_2$. Z may be selected from pyridinyl, cyclohexane, naphthalene, and morpholine. Y may be selected from a bond, —$CH_2$—, —$CH(CH_3)$—, —$CH_2CH_2$—, —$CH_2CH(CH_3)$, and —$CH(CH_3)CH_2$—.

In another, the compound of formula (I) has the following structure of formula (II):

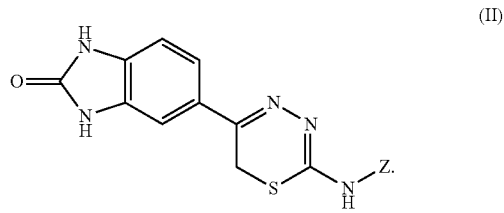

(II)

In accordance with this embodiment, Z may be selected from

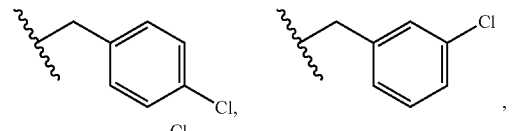

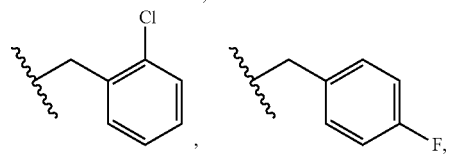

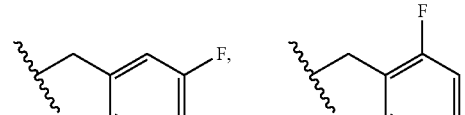

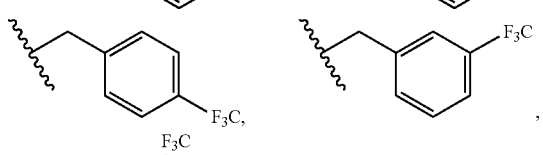

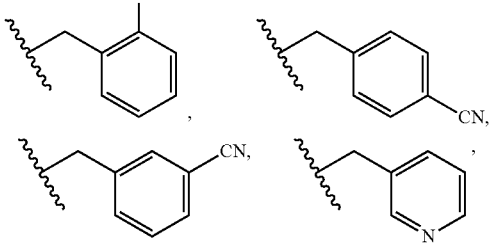

-continued

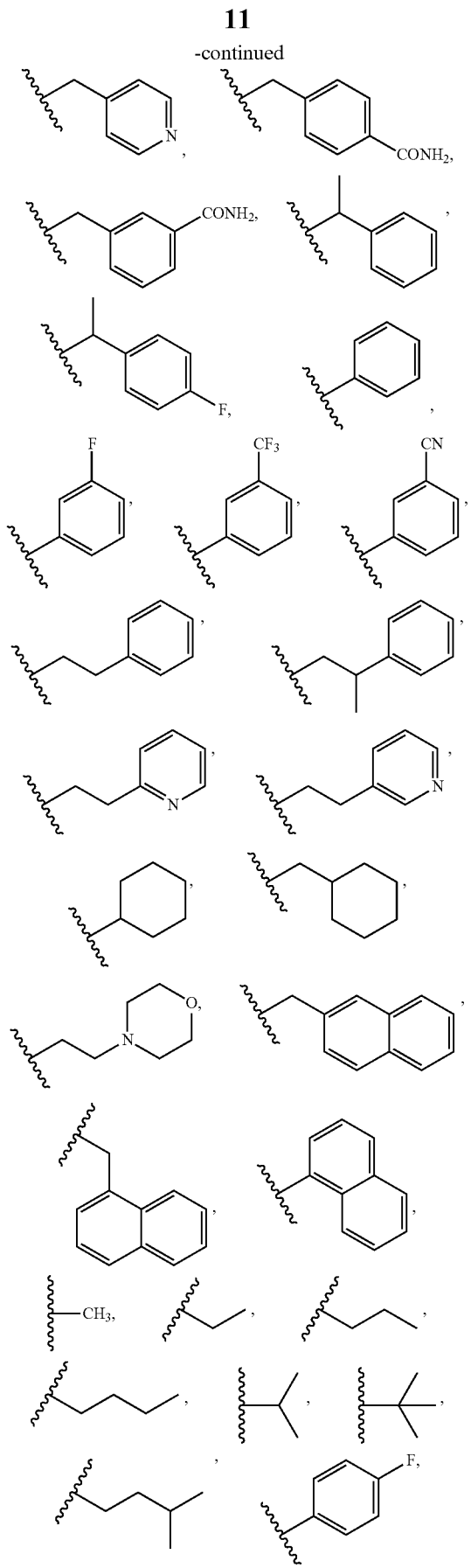

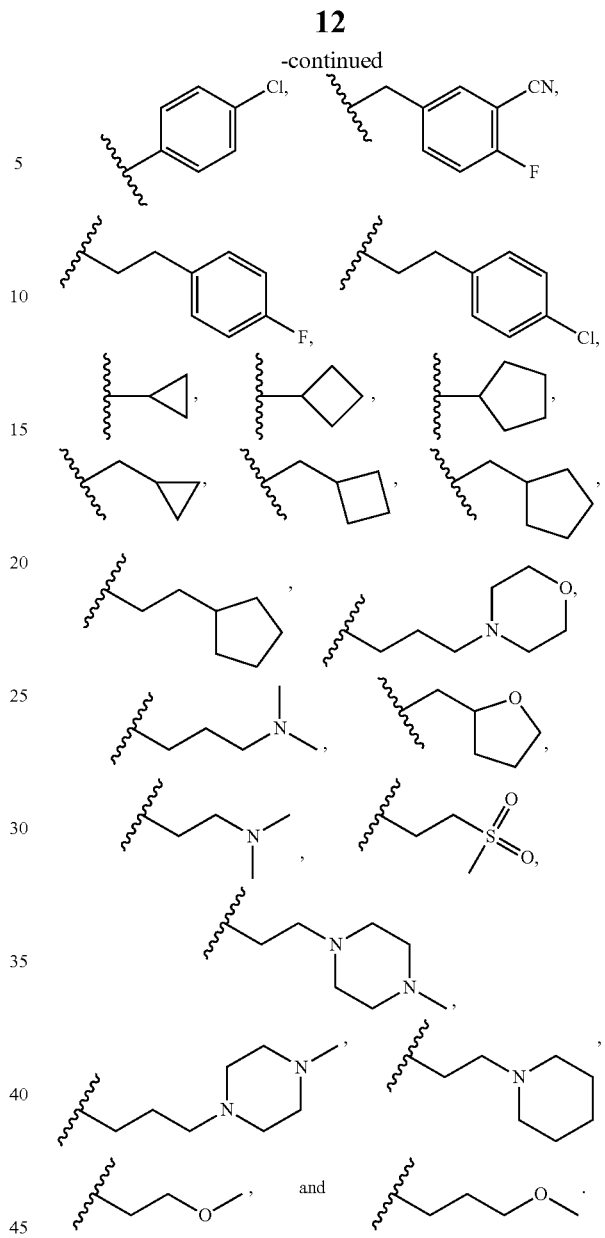

In one embodiment, Z is selected from an unsubstituted phenyl ring; a phenyl ring substituted with a halogen, —CF₃, a nitrile, or —CONH₂; pyridinyl; cyclohexane; naphthalene; and morpholine.

Another aspect of the present invention relates to a method of inhibiting activity of a kinase in a cell. This method involves contacting the cell with a compound of formula (I) of the present invention under conditions effective to inhibit activity of the kinase in the cell.

In one embodiment, the kinase is a dual-specificity tyrosine phosphorylation-regulated kinase ("DYRK"). The kinase may be a dual-specificity tyrosine phosphorylation-regulated kinase 1A ("DYRK1A").

The cell may be a mammalian cell. Mammalian cells include cells from, for example, mice, hamsters, rats, cows, sheep, pigs, goats, and horses, monkeys, dogs (e.g., *Canis familiaris*), cats, rabbits, guinea pigs, and primates, including humans. For example, the cell may be a human cell.

In one embodiment, the cell is a pancreatic beta cell. If needed, methods for determining whether a cell has a pancreatic beta cell phenotype are known in the art and include, without limitation, incubating the cell with glucose and testing whether insulin expression in the cell is increased or induced. Other methods include testing whether beta cell specific transcription factors are expressed, the detection of beta cell specific gene products with the help of RNA quantitative PCR, the transplantation of a candidate cell in diabetic mice, and subsequent testing of the physiologic response following said transplantation as well analyzing the cells with electron microscopy.

In another embodiment, the cell is a cancer cell.

In yet another embodiment, the cell is a neural cell.

Methods of the present invention may be carried out ex vivo or in vivo. When carried out ex vivo, a population of cells may be, according to one embodiment, provided by obtaining cells from a pancreas and culturing the cells in a liquid medium suitable for the in vitro or ex vivo culture of mammalian cells, in particular human cells. For example, and without limitation, a suitable and non-limiting culture medium may be based on a commercially available medium such as RPMI1640 from Invitrogen.

A further aspect of the present invention relates to a method of increasing cell proliferation in a population of pancreatic beta cells. This method involves contacting a population of pancreatic beta cells with a compound of the present invention (i.e., a compound of formula (I)) under conditions effective to increase cell proliferation in the population of pancreatic beta cells.

In one embodiment, contacting is carried out with a composition (i.e., a single composition) comprising the compound.

The method may further involve contacting the population of pancreatic beta cells with a transforming growth factor beta (TGFβ) superfamily signaling pathway inhibitor. In accordance with this embodiment, the method may be carried out with a composition comprising the compound and the TGFβ superfamily signaling pathway inhibitor. In another embodiment, the compound of formula (I) and the TGFβ superfamily signaling pathway inhibitor separately contact a population of pancreatic beta cells simultaneously or in sequence.

TGFβ superfamily signaling pathway inhibitors include small molecules and other (e.g., neutralizing monoclonal antibodies, synthetic/recombinant peptide inhibitors, and siRNA) inhibitors of the BMP family of receptors, activing and inhibin receptors, GDF11 receptors and related receptors.

TGFβ superfamily signaling pathway inhibitors are also known in the art and include, without limitation, SB431542, SB505124, A-83-01, Decorin, soluble TGF-β receptor, lerdelimumab, metelimumab, AP-12009, Follistatin, FLRG, GAST-1, GDF8 propeptide, MYO-029, Noggin, chordin, Cer/Dan, ectodin, and Sclerostin (see Tsuchida et al., "Inhibitors of the TGF-beta Superfamily and their Clinical Applications," *Mini Rev. Med. Chem.* 6(11):1255-61 (2006), which is hereby incorporated by reference in its entirety.

Other inhibitors of TGF-β signaling include, without limitation, 2-(3-(6-Methylpyridin-2-yl)-1H-pyrazol-4-yl)-1,5 naphthyridine; [3-(Pyridin-2-yl)-4-(4-quinolyl)]-1H-pyrazole; 3-(6-Methylpyridin-2-yl)-4-(4-quinolyl)-1-phenylthiocarbamoyl-1H-pyrazole; SB-431542; SM16; SB-505124; and 2-(3-(6-Methylpyridin-2-yl)-1H-pyrazol-4-yl)-1,5 naphthyridine (ALK5 Inhibitor II) (see U.S. Pat. No. 8,298,825, which is hereby incorporated by reference in its entirety).

Inhibitors of TGF-β signaling are described in Callahan et al., *J Med. Chem.* 45:999-1001 (2002); Sawyer et al., *J Med. Chem.* 46:3953-3956 (2003); Gellibert et al., *J Med. Chem.* 47:4494-4506 (2004); Tojo et al., *Cancer Sci.* 96:791-800 (2005); Valdimarsdottir et al., *APMIS* 113:773-389 (2005); Petersen et al., *Kidney International* 73:705-715 (2008); Yingling et al., *Nature Rev. Drug Disc.* 3:1011-1022 (2004); Byfield et al., *Mol. Pharmacol.* 65:744-752 (2004); Dumont et al., *Cancer Cell* 3:531-536 (2003); PCT Publication No. WO 2002/094833; PCT Publication No. WO 2004/026865; PCT Publication No. WO 2004/067530; PCT Publication No. WO 2009/032667; PCT Publication No. WO 2004/013135; PCT Publication No. WO 2003/097639; PCT Publication No. WO 2007/048857; PCT Publication No. WO 2007/018818; PCT Publication No. WO 2006/018967; PCT Publication No. WO 2005/039570; PCT Publication No. WO 2000/031135; PCT Publication No. WO 1999/058128; U.S. Pat. Nos. 6,509,318; 6,090,383; 6,419,928; 9,927,738; 7,223,766; 6,476,031; 6,419,928; 7,030,125; 6,943,191; U.S. Patent Application Publication No. 2005/0245520; U.S. Patent Application Publication No. 2004/0147574; U.S. Patent Application Publication No. 2007/0066632; U.S. Patent Application Publication No. 2003/0028905; U.S. Patent Application Publication No. 2005/0032835; U.S. Patent Application Publication No. 2008/0108656; U.S. Patent Application Publication No. 2004/015781; U.S. Patent Application Publication No. 2004/0204431; U.S. Patent Application Publication No. 2006/0003929; U.S. Patent Application Publication No. 2007/0155722; U.S. Patent Application Publication No. 2004/0138188 and U.S. Patent Application Publication No. 2009/0036382, which are hereby incorporated by reference in their entirety.

Exemplary inhibitors of TGF-β signaling include, but are not limited to, AP-12009 (TGF-β Receptor type II antisense oligonucleotide), Lerdelimumab (CAT 152, antibody against TGF-β Receptor type II) GC-1008 (antibody to all isoforms of human TGF-β), ID11 (antibody to all isoforms of murine TGF-β), soluble TGF-β, soluble TGF-β Receptor type II, dihydropyrroloimidazole analogs (e.g., SKF-104365), triarylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methylsulfinyl phenyl)-5-(4-pyridyl)-1H-imidazole)), RL-0061425, 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine), SB-431542 (4-(5-Benzol[1,3]dioxol-5-yl-4-pyridin-2-yl-1H-imidazol-2-yl)-benzamide), GW788388 (4-(4-(3-(pyridin-2-yl)-1H-pyrazol-4-yl)pyridin-2-yl)-N-(tetrahydro-2H-pyran-4-yl) benzamide), A-83-01 (3-(6-Methyl-2-pyridinyl)-N-phenyl-4-(4-quinolinyl)-1H-pyrazole-1-carbothioamide), Decorin, Lefty 1, Lefty 2, Follistatin, Noggin, Chordin, Cerberus, Gremlin, Inhibin, BIO (6-bromo-indirubin-3'-oxime), Smad proteins (e.g., Smad6, Smad7), and Cystatin C.

Inhibitors of TGF-β signaling also include molecules which inhibit TGF-β Receptor type I. Inhibitors of TGF-β Receptor type I include, but are not limited to, soluble TGF-β Receptor type I; AP-11014 (TGF-β Receptor type I antisense oligonucleotide); Metelimumab (CAT 152, TGF-β Receptor type I antibody); LY550410; LY580276 (3-(4-fluorophenyl)-5,6-dihydro-2-(6-methylpyridin-2-yl)-4H-pyrrolo[1,2-b]pyrazole); LY364947 (4-[3-(2-Pyridinyl)-1H-pyrazol-4-yl]-quinoline); LY2109761; LY573636 (N-((5-bromo-2-thienyl)sulfonyl)-2,4-dichlorobenzamide); SB-505124 (2-(5-Benzo[1,3]dioxol-5-yl-2-tert-butyl-3H-imidazol-4-yl)-6-methylpyridine); SD-208 (2-(5-Chloro-2-fluorophenyl)-4-[(4-pyridyl)amino]pteridine); SD-093; KI2689; SM16; FKBP12 protein; and 3-(4-(2-(6-methylpyridin-2-yl)H-imidazo[1,2-a]pyridin-3-yl)quinolin-7-yloxy)-N,N-dimethylpropan-1-amine.

Inhibitors of TGF-β Receptor type I are described in Byfield and Roberts, *Trends Cell Biol.* 14:107-111 (2004); Sawyer et al., *Bioorg. Med. Chem. Lett.* 14:3581-3584 (2004); Sawyer et al., *J Med. Chem.* 46:3953-3956 (2003); Byfield et al., *Mol. Pharmacol.* 65:744-752 (2004); Gellibert et al., *J Med. Chem.* 47:4494-4506 (2004); Yingling et al., *Nature Rev. Drug Disc.* 3:1011-1022 (2004); Dumont et al., *Cancer Cell* 3:531-536 (2003); Tojo et al., *Cancer Sci.* 96:791-800 (2005); PCT Publication No. WO 2004/026871; PCT Publication No. WO 2004/021989; PCT Publication No. WO 2004/026307; PCT Publication No. WO 2000/012497; U.S. Pat. Nos. 5,731,424; 5,731,144; 7,151,169; U.S. Patent Application Publication No. 2004/00038856 and U.S. Patent Application Publication No. 2005/0245508, all of which are herein incorporated in their entirety.

In one embodiment, the TGFβ superfamily signaling pathway inhibitor includes compounds that interfere with TGFβ superfamily ligands, receptors, and/or downstream signaling molecules (e.g., SMADs) or nuclear targets (e.g., chromatin modifying complexes and transcription factors).

In one embodiment, the TGFβ superfamily signaling pathway inhibitor may be antisera that neutralize, e.g., TGFβ ligand.

In another embodiment, the TGFβ superfamily signaling pathway inhibitor is selected from the group consisting of an inhibitor of TGFβ/TGFβ receptor binding, activin or inhibin/activin receptor binding, and bone morphogenetic protein (BMP)/BMP receptor binding.

In a specific embodiment, the TGFβ superfamily signaling pathway inhibitor is an inhibitor of TGFβ/TGFβ receptor binding selected from the group consisting of LY364947 and GW788388.

In another specific embodiment, the TGFβ superfamily signaling pathway inhibitor is an inhibitor of activin or inhibin/activin receptor binding selected from the group consisting of SB431542 and Alk5 inhibitor II. Additional exemplary inhibitors of activin or inhibin/activin receptor binding may be selected from the group consisting of SB-505124, BYM388, follistatin, follistatin-related protein (FSRP), follistatin domains (i.e., Fs2, Fs12, Fs123), A-83-01, Cripto, GW788388, BAMBI, and Sotatercept (see Byfield et al., "SB-505124 is a Selective Inhibitor of Transforming Growth Factor-Beta Type I Receptors ALK4, ALK5, and ALK7," *Mol. Pharmacol.* 65(3):744-52 (2004); Lach-Trifilieffa et al., "An Antibody Blocking Activin Type II Receptors Induces Strong Skeletal Muscle Hypertrophy and Protects from Atrophy," *Mol. Cell. Biol.* 34(4):606-18 (2014); Zhang et al., "Inhibition of Activin Signaling Induces Pancreatic Epithelial Cell Expansion and Diminishes Terminal Differentiation of Pancreatic β-Cells," *Diabetes* 53(8):2024-33 (2004); Harrington et al., "Structural Basis for the Inhibition of Activin Signalling by Follistatin," *EMBO J.* 25(5):1035-45 (2006); Tojo et al., "The ALK-5 Inhibitor A-83-01 Inhibits Smad Signaling and Epithelial-to-Mesenchymal Transition by Transforming Growth Factor-Beta," *Cancer Sci.* 96(11):790-800 (2005); Yan et al., "Human BAMBI Cooperates with Smad7 to Inhibit Transforming Growth Factor-Beta Signaling," *J Biol. Chem.* 284(44):30097-104 (2009); Tan et al., "Targeted Inhibition of Activin Receptor-Like Kinase 5 Signaling Attenuates Cardiac Dysfunction Following Myocardial Infarction," *Am. J Physiol. Heart Circ. Physiol.* 298(5):H1415-25 (2010); and Gokoffski et al., "Activin and GDF11 Collaborate in Feedback Control of Neuroepithelial Stem Cell Proliferation and Fate," *Develop.* 138(19):4131-42 (2011), which are hereby incorporated by reference in their entirety).

In another specific embodiment, the TGFβ superfamily signaling pathway inhibitor is an inhibitor of BMP/BMP receptor binding. An exemplary inhibitor of BMP/BMP receptor binding is LDN193189. Additional exemplary BMP inhibitors may be selected from the group consisting of noggin, sclerostin, chordin, CTGF, follistatin, gremlin, inhibin, DMH1, DMH2, Dorsomorphin, K02288, LDN212854, DM 3189, BMP-3, and BAMBI (see WO 2014018691 A1 and Mohedas et al., "Development of an ALK2-Biased BMP Type I Receptor Kinase Inhibitor," *ACS Chem. Biol.* 8(6):1291-302 (2013); Yan et al., "Human BAMBI Cooperates with Smad7 to Inhibit Transforming Growth Factor-Beta Signaling," *J. Biol. Chem.* 284(44): 30097-104 (2009), which are hereby incorporated by reference in their entirety).

According to another embodiment, the TGFβ superfamily signaling pathway inhibitor is a SMAD signaling pathway inhibitor. Exemplary SMAD signaling pathway inhibitors may be selected from the group including, without limitation, SMAD3 siRNA, SMAD 2/3 siRNA, PD169316, SB203580, SB202474, specific inhibitor of Smad3 (SIS3), HSc025, and SB525334 (see Qureshi et al., "Smad Signaling Pathway is a Pivotal Component of Tissue Inhibitor of Metalloproteinases-3 Regulation by Transforming Growth Factor Beta in Human Chondrocytes," *BBA Mol. Cell Res.* 1783(9):1605-12 (2008); Hasegawa et al., "A Novel Inhibitor of Smad-Dependent Transcriptional Activation Suppresses Tissue Fibrosis in Mouse Models of Systemic Sclerosis, *Arthritis Rheum.* 60(11):3465-75 (2009); and Ramdas et al., "Canonical Transforming Growth Factor-β Signaling Regulates Disintegrin Metalloprotease Expression in Experimental Renal Fibrosis via miR-29," *Am. J. Pathol.* 183(6):1885-96 (2013), which are hereby incorporated by reference in their entirety).

Additional exemplary SMAD signaling pathway inhibitors include, without limitation, miR-100, LDN 193189, SMAD-binding peptide aptamers (e.g., Trx-FoxH1, Trx-Le1, Trx-CBP, Trx-SARA), pirfenidone, and LDN193189 (see Fu et al., "MicroRNA-100 Inhibits Bone Morphogenetic Protein-Induced Osteoblast Differentiation by Targeting Smad," *Eur. Rev. Med. Pharmacol. Sci.* 20(18):3911-19 (2016); Boergermann et al., "Dorsomorphin and LDN-193189 Inhibit BMP-Mediated Smad, p38 and Akt signalling in C2C12 Cells," *Int. J Biochem. Cell Biol.* 42(11): 1802-7 (2010); Cui et al., "Selective Inhibition of TGF-Responsive Genes by Smad-Interacting Peptide Aptamers from FoxH1, Lef1 and CBP," *Oncogene* 24:3864-74 (2005); Zhao et al., "Inhibition of Transforming Growth Factor-Beta1-Induced Signaling and Epithelial-to-Mesenchymal Transition by the Smad-Binding Peptide Aptamer Trx-SARA," *Mol. Biol. Cell* 17:3819-31 (2006); Li et al., "Oral Pirfenidone Protects Against Fibrosis by Inhibiting Fibroblast Proliferation and TGF-β Signaling in a Murine Colitis Model," *Biochem. Pharmacol.* 117:57-67 (2016); and Cook et al., "BMP Signaling Balances Murine Myeloid Potential Through SMAD-Independent p38MAPK and NOTCH Pathways," *Blood* 124(3):393-402 (2014), which are hereby incorporated by reference in their entirety).

In another specific embodiment, the TGFβ superfamily signaling pathway inhibitor is an inhibitor of the trithorax complex. Exemplary trithorax complex inhibitors include, without limitation, WDR5-0103, MI-1, MI-2, MI-2-2, MLS001171971-01, ML227, MCP-1, RBB5 siRNA, and MLL1 siRNA (see Senisterra et al., "Small-Molecule Inhibition of MLL Activity by Disruption of its Interaction with WDR5," *Biochem. J.* 449(1):151-9 (2013); Cierpicki et al., "Challenges and Opportunities in Targeting the Menin-MLL Interaction," *Future Med. Chem.* 6(4):447-62 (2014); Lee et al., "Roles of DPY30 in the Proliferation and Motility of Gastric Cancer Cells," *PLOS One* 10(7):e0131863 (2015); and Zhou et al., "Combined Modulation of Polycomb and Trithorax Genes Rejuvenates β Cell Replication," *J Clin. Invest.* 123(11):4849-4858 (2013), which are hereby incorporated by reference in their entirety).

In another embodiment, the TGFβ superfamily signaling pathway inhibitor is an inhibitor of the polycomb repressive complex 2 ("PRC2"). Exemplary PRC2 inhibitors include GSK926, EPZ005687, GSK126, GSK343, Eli, UNC1999, EPZ6438, Constellation Compound 3, EZH2 siRNA, and 3-deazaneplanocin A (see Verma et al., "Identification of Potent, Selective, Cell-Active Inhibitors of the Histone Lysine Methyltransferase EZH2," *ACS Med. Chem. Lett.* 3:1091-6 (2012); Xu et al., "Targeting EZH2 and PRC2 Dependence as Novel Anticancer Therapy," *Exp. Hematol.* 43:698-712 (2015); Knutson et al., "A Selective Inhibitor of EZH2 Blocks H3K27 Methylation and Kills Mutant Lymphoma Cells," *Nat. Chem. Biol.* 8:890-6 (2012); Qi et al., "Selective Inhibition of Ezh2 by a Small Molecule Inhibitor Blocks Tumor Cells Proliferation," *Proc. Natl Acad. Sci. USA* 109:21360-65 (2012); McCabe et al., "EZH2 Inhibition as a Therapeutic Strategy for Lymphoma with EZH2-Activating Mutations," *Nature* 492:108-12 (2012); Nasveschuk et al., "Discovery and Optimization of Tetramethylpiperidinyl Benzamides as Inhibitors of EZH2," *ACS Med. Chem. Lett.* 5:378-83 (2014); Brooun et al., "Polycomb Repressive Complex 2 Structure with Inhibitor Reveals a Mechanism of Activation and Drug Resistance," *Nature Comm.* 7:11384 (2016); Fiskus et al., "Histone Deacetylase Inhibitors Deplete Enhancer of Zeste 2 and Associated Polycomb Repressive Complex 2 Proteins in Human Acute Leukemia Cells," *Mol. Cancer Ther.* 5(12):3096-104 (2006); and Fiskus et al., "Combined Epigenetic Therapy with the Histone Methyltransferase EZH2 Inhibitor 3-Deazaneplanocin A and the Histone Deacetylase Inhibitor Panobinostat Against Human AML Cells," *Blood* 114(13):2733-43 (2009), which are hereby incorporated by reference in their entirety.)

According to one embodiment, "pancreatic beta cells" are primary human pancreatic beta cells.

In one embodiment of carrying out this and other methods of the present invention, contacting does not induce beta cell death or DNA damage. Moreover, contacting may induce beta cell differentiation and increase glucose-stimulated insulin secretion.

In another embodiment, the method is carried out to enhance cell survival. For example, the method may be carried out to enhance cell survival of a treated population of cells relative to an untreated population of cells. Alternatively, the method may be carried out to decrease cell death or apoptosis of a treated population of cells relative to an untreated population of cells.

A further aspect of the present invention relates to a composition comprising a compound according to the first aspect of the invention and a carrier.

In one embodiment, the composition may further comprise a transforming growth factor beta (TGFβ) superfamily signaling pathway inhibitor.

The carrier may be a pharmaceutically-acceptable carrier.

While it may be possible for the compounds of the present invention (i.e., compounds of formula (I)) to be administered as the raw chemical, it may be preferable to present them as a pharmaceutical composition. In accordance with an embodiment of the present invention, there is provided a pharmaceutical composition comprising a compound of formula (I) or a pharmaceutically acceptable salt or solvate thereof, together with one or more pharmaceutically carriers thereof and optionally one or more other therapeutic ingredients.

The carrier(s) must be "acceptable" in the sense of being compatible with the other ingredients of the formulation and not deleterious to the recipient thereof. Furthermore, notwithstanding the statements herein regarding the term "compound" including salts thereof as well, so that independent claims reciting "a compound" will be understood as referring to salts thereof as well, if in an independent claim reference is made to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

Formulations include those suitable for oral, parenteral (including subcutaneous, intradermal, intramuscular, intravenous, and intraarticular), rectal and topical (including dermal, buccal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula (I) or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier," and this expression is intended to include one or more inert excipients, which include, for example and without limitation, starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula (I) to insure the stability of the formulation. The composition may contain other additives as needed including, for example, lactose, glucose, fructose, galactose, trehalose, sucrose, maltose, raffinose, maltitol, melezitose, stachyose, lactitol, palatinate, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to, binders, fillers, disintegrants, lubricants, anti-microbial agents, and coating agents.

Dose ranges for adult humans vary, but may generally be from about 0.005 mg to 10 g/day orally. Tablets or other forms of presentation provided in discrete units may conveniently contain an amount of compound of formula (I) which is effective at such dosage or as a multiple of the same, for instance, units containing 5 mg to 500 mg, or around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

Additional information about pharmaceutical compositions and their formulation is described in *Remington: The Science and Practice of Pharmacy*, 20$^{th}$ Edition, 2000, which is hereby incorporated by reference in its entirety.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g., PCT Publication No. WO 97/11682, which is hereby incorporated by reference in its entirety) via a liposomal formulation (see, e.g., EP Patent No. 736299, PCT Publication No. WO 99/59550, and PCT Publication No. WO 97/13500, which is hereby incorporated by reference in its entirety), via formulations described in PCT Publication No. WO 03/094886 (which is hereby incorporated by reference in its entirety) or in some other form. The agents can also be administered transdermally (i.e., via reservoir-type or matrix-type patches, microneedles, thermal poration, hypodermic needles, iontophoresis, electroporation, ultrasound, or other forms of sonophoresis, jet injection, or a combination of any of the preceding methods (Prausnitz et al. *Nature Reviews Drug Discovery* 3:115 (2004), which is hereby incorporated by reference in its entirety). The agents can be administered locally.

The agents can be administered in the form a suppository or by other vaginal or rectal means. The agents can be administered in a transmembrane formulation as described in PCT Publication No. WO 90/07923, which is hereby incorporated by reference in its entirety. The agents can be administered non-invasively via the dehydrated particles described in U.S. Pat. No. 6,485,706, which is hereby incorporated by reference in its entirety. The agents can be administered in an enteric-coated drug formulation as described in PCT Publication No. WO 02/49621, which is hereby incorporated by reference in its entirety. The agents can be administered intranasally using the formulation described in U.S. Pat. No. 5,179,079, which is hereby incorporated by reference in its entirety. Formulations suitable for parenteral injection are described in PCT Publication No. WO 00/62759, which is hereby incorporated by reference in its entirety. The agents can be administered using the casein formulation described in U.S. Patent Application Publication No. 2003/0206939 and PCT Publication No. WO 00/06108, which are hereby incorporated by reference in their entirety. The agents can be administered using the particulate formulations described in U.S. Patent Application Publication No. 20020034536, which is hereby incorporated by reference in its entirety.

The agents, alone or in combination with other suitable components, can be administered by pulmonary route utilizing several techniques including, but not limited to, intratracheal instillation (delivery of solution into the lungs by syringe), intratracheal delivery of liposomes, insufflation (administration of powder formulation by syringe or any other similar device into the lungs), and aerosol inhalation. Aerosols (e.g., jet or ultrasonic nebulizers, metered-dose inhalers ("MDIs"), and dry-Powder inhalers ("DPIs")) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e., HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include, but are not limited to, bile salts and those described in U.S. Pat. No. 6,524,557 and references therein, which are hereby incorporated by reference in their entirety. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers that can be added to dry powder formulations include those described in U.S. Pat. No. 6,632,456, which is hereby incorporated by reference in its entirety. PCT Publication No. WO 02/080884, which is hereby incorporated by reference in its entirety, describes new methods for the surface modification of powders. Aerosol formulations may include those described in U.S. Pat. Nos. 5,230,884 and 5,292,499; PCT Publication Nos. WO 017/8694 and 01/78696; and U.S. Patent Application Publication No. 2003/019437, 2003/0165436; and PCT Publication No. WO 96/40089 (which includes vegetable oil), which are hereby incorporated by reference in their entirety. Sustained release formulations suitable for inhalation are described in U.S. Patent Application Publication Nos. 2001/0036481, 2003/0232019, and 2004/0018243 as well as in PCT Publication Nos. WO 01/13891, 02/067902, 03/072080, and 03/079885, which are hereby incorporated by reference in their entirety.

Pulmonary formulations containing microparticles are described in PCT Publication No. WO 03/015750, U.S. Patent Application Publication No. 2003/0008013, and PCT Publication No. WO 00/00176, which are hereby incorporated by reference in their entirety. Pulmonary formulations containing stable glassy state powder are described in U.S. Patent Application Publication No. 2002/0141945 and U.S. Pat. No. 6,309,671, which are hereby incorporated by reference in their entirety. Other aerosol formulations are described in EP Patent No. 1338272, PCT Publication No. WO 90/09781, U.S. Pat. Nos. 5,348,730 and 6,436,367, PCT Publication No. WO 91/04011, and U.S. Pat. Nos. 6,294,153 and 6,290,987, which are hereby incorporated by reference in their entirety, which describe a liposomal based formulation that can be administered via aerosol or other means.

Powder formulations for inhalation are described in U.S. Patent Application Publication No. 2003/0053960 and PCT Publication No. WO 01/60341, which are hereby incorporated by reference in their entirety. The agents can be administered intranasally as described in U.S. Patent Application Publication No. 2001/0038824, which is hereby incorporated by reference in its entirety.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy.

Other devices for generating aerosols employ compressed gases, usually hydrofluorocarbons and chlorofluorocarbons, which are mixed with the medicament and any necessary excipients in a pressurized container. These devices are likewise described in standard textbooks such as Sprowls and Remington.

The agent can be incorporated into a liposome to improve half-life. The agent can also be conjugated to polyethylene glycol ("PEG") chains. Methods for pegylation and additional formulations containing PEG-conjugates (i.e., PEG-based hydrogels, PEG modified liposomes) can be found in Harris and Chess, *Nature Reviews Drug Discovery* 2:214-221, which is hereby incorporated by reference in its entirety, and the references therein. The agent can be administered via a nanocochleate or cochleate delivery vehicle (BioDelivery Sciences International). The agents can be delivered transmucosally (i.e., across a mucosal surface such as the vagina, eye or nose) using formulations such as that described in U.S. Pat. No. 5,204,108, which is hereby incorporated by reference in its entirety. The agents can be formulated in microcapsules as described in PCT Publication No. WO 88/01165, which is hereby incorporated by reference in its entirety. The agent can be administered intra-orally using the formulations described in U.S. Patent Application Publication No. 2002/0055496, PCT Publication No. WO 00/47203, and U.S. Pat. No. 6,495,120, which are hereby incorporated by reference in their entirety. The agent can be delivered using nanoemulsion formulations described in PCT Publication No. WO 01/91728, which is hereby incorporated by reference in its entirety.

Another aspect of the present invention relates to a method of treating a subject for a condition associated with an insufficient level of insulin secretion. The method involves administering to a subject in need of treatment for a condition associated with an insufficient level of insulin secretion a compound or composition of the present invention.

In one embodiment, the treatment methods of the present invention are carried out under conditions effective to increase pancreatic beta cell mass in the subject to treat the subject for an insufficient level of insulin secretion.

In one embodiment, the compound or composition may be administered with or coincident with a TGFβ superfamily signaling pathway inhibitor.

As used herein, a condition associated with an insufficient level of insulin secretion means a condition where a subject produces a lower plasma level of insulin than is required to maintain normal glucose levels in the blood such that the subject with the condition associated with insufficient insulin secretion becomes hyperglycemic. In such a condition, the pancreatic beta cells of the afflicted subject secrete an insufficient level of insulin to maintain the presence of a normal concentration of glucose in the blood (i.e., normoglycemia).

According to one embodiment, one of the conditions associated with an insufficient level of insulin secretion is insulin resistance. Insulin resistance is a condition in which a subject's cells become less sensitive to the glucose-lowering effects of insulin. Insulin resistance in muscle and fat cells reduces glucose uptake (and, therefore, local storage of glucose as glycogen and triglycerides), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and type II diabetes occurs.

According to another embodiment, one of the conditions associated with an insufficient level of insulin secretion is diabetes. Diabetes can be divided into two broad types of diseases: type I (T1D) and type II (T2D). The term "diabetes" also refers herein to a group of metabolic diseases in which patients have high blood glucose levels, including type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes (e.g., steroid diabetes), and several forms of monogenic diabetes.

Thus, in one embodiment, the subject has been diagnosed as having one or more of type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes, or monogenic diabetes.

According to another embodiment, a condition associated with an insufficient level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance), high blood pressure; central obesity (also known as visceral, male-pattern or apple-shaped adiposity), meaning overweight with fat deposits mainly around the waist; decreased HDL cholesterol; and elevated triglycerides.

In one embodiment, the subject has been diagnosed as having metabolic syndrome or insulin resistance.

Other conditions that may be associated with an insufficient level of insulin secretion include, without limitation, hyperuricemia, fatty liver (especially in concurrent obesity) progressing to non-alcoholic fatty liver disease, polycystic ovarian syndrome (in women), and acanthosis nigricans.

Related disorders may also be treated pursuant to the treatment methods of the present invention including, without limitation, any disease associated with a blood or plasma glucose level outside the normal range, preferably hyperglycemia. Consequently, the term "related disorders" includes impaired glucose tolerance (IGT), impaired fasting glucose (IFG), insulin resistance, metabolic syndrome, postprandial hyperglycemia, and overweight/obesity. Such related disorders can also be characterized by an abnormal blood and/or plasma insulin level.

According to another embodiment, the methods of the present invention are carried out to treat a subject with conditions associated with beta cell failure or deficiency. Such conditions include, without limitation, type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes, or monogenic diabetes. Drug induced diabetes relates to a condition that is caused through the use of drugs that are toxic to beta cells (e.g., steroids, antidepressants, second generation antipsychotics, and immunosuppressive. Exemplary
immunosuppressive drugs include, but are not limited to, members of the cortisone family (e.g., prednisone and dexamethasome), rapamycin/sirolimus, everolimus, and calciuneurin inhibitors (e.g., FK-506/tacrolimus).

Additional conditions associated with beta cell deficiency include pancreatectomy, partial pancreatectomy, pancreas transplantation, and pancreatic islet transplantation.

In another embodiment, the methods of the present invention are carried out to treat a subject at risk of developing Type II Diabetes. In one embodiment, a patient at risk of developing Type II Diabetes has pre-diabetes/metabolic syndrome. In another embodiment, the patient at risk of developing Type II Diabetes has been treated with a psychoactive drug, including but not limited to a selective serotonin reuptake inhibitors ("SSRI") for depression, obsessive compulsive disorder ("OCD"), etc.

In carrying out the treatment methods of the present invention, a compound or composition of the present invention and a TGFβ superfamily signaling pathway inhibitor are administered under conditions effective to increase pancreatic beta cell mass in the subject to treat the subject for a condition associated with an insufficient level of insulin secretion.

According to one embodiment, a compound or composition of the present invention and/or TGFβ superfamily signaling pathway inhibitor are administered to increase pancreatic beta cell mass in the subject, which will result in an increased level of insulin secretion in the subject.

The compound and/or composition of the present invention and TGFβ superfamily signaling pathway inhibitor are, according to one embodiment, formulated as separate pharmaceutical compositions or a single pharmaceutical composition comprising both the compound of formula (I) and TGFβ superfamily signaling pathway inhibitor. According to one embodiment, such pharmaceutical composition(s) comprises a therapeutically effective amount of the compound of formula (I) and/or TGFβ superfamily signaling pathway inhibitor.

Thus, according to one embodiment, a combination or combinatorial therapy or treatment of a compound of the present invention and TGFβ superfamily signaling pathway inhibitor are administered. The terms "combination" or "combinatorial therapy" or "combinatory treatment" mean a treatment where at least two compounds are co-administered to a subject to cause a biological effect, in this case a synergistic effect. In a combinatorial therapy, the at least two drugs may be administered together or separately, at the same time or sequentially. Simultaneous administration is not required, as long as the drugs produce a synergistic effect in the subject to improve the subject's conditions. Also, the at least two drugs may be administered through different routes and protocols. As a result, although they may be formulated together, the drugs of a combination may also be formulated separately.

A further aspect of the present invention relates to a method of treating a subject for a neurological disorder. This method involves administering to a subject in need of treatment for a neurological disorder a compound of the present invention under conditions effective to treat the subject for the condition.

In one embodiment, the subject has diabetes and/or has been diagnosed as having one or more of Down's Syndrome and a neurodegenerative disease.

In carrying out the treatment methods of the present invention, administering of compounds to a subject may involve administering pharmaceutical compositions containing the compound(s) (i.e., a DYRK1A inhibitor of formula (I) and TGFβ superfamily signaling pathway inhibitor) in therapeutically effective amounts, which means an amount of compound effective in treating the stated conditions and/or disorders in the subject. Such amounts generally vary according to a number of factors well within the purview of ordinarily skilled artisans. These include, without limitation: the particular subject, as well as its age, weight, height, general physical condition, and medical history, the particular compound used, as well as the carrier in which it is formulated and the route of administration selected for it; the length or duration of treatment; and the nature and severity of the condition being treated.

Administering typically involves administering pharmaceutically acceptable dosage forms, which means dosage forms of compounds described herein and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

In carrying out treatment methods of the present invention, the drug (i.e., a compound of formula (I) and, optionally, a TGFβ superfamily signaling pathway inhibitor) may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

Pharmaceutical compositions according to the present invention may be formulated to release the active drug substantially immediately upon administration or at any predetermined time or time period after administration.

Controlled release formulations include (i) formulations that create a substantially constant concentration of the drug(s) within the body over an extended period of time; (ii) formulations that after a predetermined lag time create a substantially constant concentration of the drug(s) within the body over an extended period of time; (iii) formulations that sustain drug(s) action during a predetermined time period by maintaining a relatively, constant, effective drug level in the body with concomitant minimization of undesirable side effects associated with fluctuations in the plasma level of the active drug substance; (iv) formulations that localize drug(s) action by, e.g., spatial placement of a controlled release composition adjacent to or in the diseased tissue or organ; and (v) formulations that target drug(s) action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index ("TI") is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be pursued to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Thus, administering according to this aspect of the invention may be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Compounds may be administered alone or with suitable pharmaceutical carriers, and can be in solid or liquid form, such as tablets, capsules, powders, solutions, suspensions, or emulsions.

The subject may be a mammalian subject. In one embodiment, the subject is a human subject. Suitable human subjects include, without limitation, children, adults, and elderly subjects having a beta-cell and/or insulin deficiency.

In other embodiments, the subject may be bovine, ovine, porcine, feline, equine, murine, canine, lapine, etc.

In one embodiment, the administering step may increase the number of proliferating pancreatic beta cells in the subject by at least about 5%, 6%, 7%, or more.

In some embodiments, the administering increases glucose-stimulated insulin secretion in pancreatic beta cells of the subject.

In one embodiment of this and other aspects of the present invention, the designation of a compound is meant to designate the compound per se, as well as any pharmaceutically acceptable salt, hydrate, isomer, racemate, ester, or ether thereof. The designation of a compound is meant to designate the compound as specifically designated per se, as well as any pharmaceutically acceptable salt thereof.

Within the context of the present invention, by "treating" it is meant preventive or curative treatment.

In one embodiment, the term treatment designates in particular the correction, decrease in the rate of change, or reduction of an impaired glucose homeostasis. The level of glucose in blood fluctuates throughout the day. Glucose levels are usually lower in the morning, before the first meal of the day and rise after meals for some hours. Consequently, the term treatment includes the control of blood glucose level by increasing or decreasing blood glucose level depending on the condition of the subject and the daytime in order to reach normal glucose levels. The term treatment more particularly includes a temporary or persistent reduction of blood glucose level in a subject having diabetes or a related disorder. The term "treatment" or "treating" also designates an improvement in insulin release (e.g., by pancreatic beta cells).

As used herein, the phrase "control of blood glucose level" refers to the normalization or the regulation of the blood or plasma glucose level in a subject having abnormal levels (i.e., levels that are below or above a known reference, median, or average value for a corresponding subject with a normal glucose homeostasis).

EXAMPLES

Materials and Methods for Examples 1-2

Materials and Methods for Example 1-X. $^1$H and $^{13}$C NMR spectra were acquired on a Bruker DRX-600 spectrometer at 600 MHz for $^1$H and 150 MHz for 13 C. TLC was performed on silica coated aluminum sheets (thickness 200 μm) or alumina coated (thickness 200 μm) aluminum sheets supplied by Sorbent Technologies and column chromatography was carried out on Teledyne ISCO combiflash equipped with a variable wavelength detector and a fraction collector using RediSep Rf high performance silica flash columns by Teledyne ISCO. LCMS analysis was conducted on an Agilent Technologies G1969A high-resolution API-TOF mass spectrometer attached to an Agilent Technologies 1200 HPLC system. Samples were ionized by electrospray ionization (ESI) in positive mode. Chromatography was performed on a 2.1×150 mm Zorbax 300SB-$C_{18}$ 5 μm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). The temperature of the column was held at 50° C. for the entire analysis. The chemicals and reagents were purchased from Aldrich Co., Alfa Aesar, and Enamine, TCI USA. All solvents were purchased in anhydrous from Acros Organics and used without further purification.

All active compounds were synthesized independently in analytically pure form. They were chemically stable and exhibited a dose dependent DYRK1A binding without showing any erroneous/misleading readouts due to any aggregation, and decomposition, prevalent among known classes of Pan Assay Interference compounds (PAINS).

DYRK1A Binding Assays. Compounds were tested for DYRK1A binding activity at two different commercial kinase profiling services, Life Technologies and DiscoverX. Life Technologies uses the FRET-based LanthaScreen® Eu Kinase Binding Assay, whereas DiscoverX uses proprietary KINOMEscan® Assay (Fabian et al., "A Small Molecule-kinase Interaction Map for Clinical Kinase Inhibitors," *Nat. Biotechnol.* 23(3):329-336 (2005), which is hereby incorporated by reference in its entirety). Compounds were screened for DYRK1A activity at a single concentration of 30 μM in duplicates. Similarly, the dissociation constant $K_d$ of the hit compounds from the initial screening was determined at DiscoverX using their proprietary KINOMEscan® Assay. $K_d$ values are determined using eleven serial three fold dilutions with the highest concentration of 60 μM.

Synthesis of 5-(2-chloroacetyl)-1H-benzo[d]imidazol-2(3H)-one (Compound 2)

Kornberg et al., "Preparation of Piperidine Derivatives as Subtype Selective n-methyl-d-aspartate Antagonists Useful in the Treatment of Cerebral Vascular Disorders and PCT Publication No. WO 2002/050070, which are hereby incorporated by reference in their entirety:

(Compound 2)

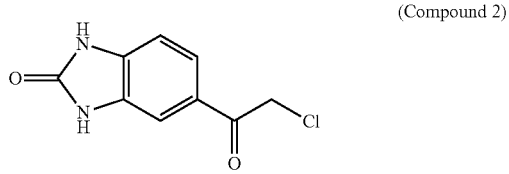 [SMILES: O=C(CCl)c1ccc2[nH]c(=O)[nH]c2c1]

To a suspension of aluminium chloride (5.16 g, 38.76 mmol) in DCE (20 mL) was added 2-chloroacetyl chloride (2.34 mL, 29.8 mmol) dropwise at 0° C. under Argon atmosphere and stirred for 30 minutes. A solution of 2-hydroxybenzimidazole 1 (2 g, 14.9 mmol) in DCE (5 mL) was added slowly to the above solution and stirred at 50° C. for 2 hours and then overnight at room temperature. Upon completion of reaction monitored by LC/MS, the mixture was poured onto ice to obtain the product as a white precipitate, which was filtered and washed with water and EtOAc. Consequently, the compound was dried under high vacuum to provide the desired product 5-(2-chloroacetyl)-1H-benzo[d]imidazol-2(3H)— one (compound 2) (3.1 g, 99%) as a white solid.

$^1$H-NMR (600 MHz, d6-DMSO): δ 11.13 (s, 1H), 10.98 (s, 1H), 7.69-7.67 (d, 1H), 7.49 (s, 1H), 7.05-7.04 (d, 1H), 5.13 (s, 2H); LCMS (TOF-ESI) for $C_9H_7ClN_2O_2$[M] 210.0196; Calculated: 211.0266; Found [M+H]+ for 211.0261.

Synthesis of N-benzyl-5-(benzo[d]imidazol-2(3H)-one)-6H-1,3,4-thiadiazin-2-amine hydrochloride salt (Compound 1)

Pfeiffer et al., Unexpected Ring Enlargement of 2-Hydrazono-2,3-dihydro-1,3-thiazoles to 1,3,4-Thiadiazines," *Helv. Chim. Acta.* 97(1):76-87 (2014), which is hereby incorporated by reference in its entirety:

HCl salt

A solution of 5-(2-chloroacetyl)-1H-benzo[d]imidazol-2(3H)-one (compound 2) (0.15 g, 0.714 mmol, 1 equiv.) and N-benzylhydrazinecarbothioamide (0.15 g, 1.1 equiv.) in DMF/HOAc (2 mL/0.2 mL) was stirred at room temperature for 12 hours. Upon completion of the reaction monitored by LC/MS, the mixture was concentrated under high vacuum to remove solvent, the residue was triturated with $CH_2Cl_2$, the precipitate was washed with $CH_2Cl_2$ and dried under high vacuum to give desired product 1 (0.22 g, 90%) as a white solid. $^1$H-NMR (600 MHz, $d_6$-DMSO): δ 11.01 (s, 1H), 10.94 (s, 1H), 7.54-7.53 (d, 1H), 7.48 (s, 1H), 7.44-7.39 (m, 4H), 7.37-7.35 (m, 1H), 7.07-7.05 (d, 1H), 4.71 (s, 2H), 4.22 (s, 2H); $^{13}$C-NMR (150 MHz, $d_6$-DMSO): δ 158.87, 155.41, 152.13, 135.79, 132.82, 130.31, 128.73, 127.94, 125.19, 120.73, 108.53, 106.60, 47.31, 22.21; HRMS (ESI): m/z [M+H]+ calcd for $C_{17}H_{16}N_5OS$+: 338.1070, found: 338.1070; Purity >95%.

General Procedure for the Synthesis of Compound 3

Pfeiffer et al., "Unexpected Ring Enlargement of 2-Hydrazono-2,3-dihydro-1,3-thiazoles to 1,3,4-Thiadiazines," *Helv. Chim. Acta.* 97(1):76-87 (2014), which is hereby incorporated by reference in its entirety:

(Compound 3)

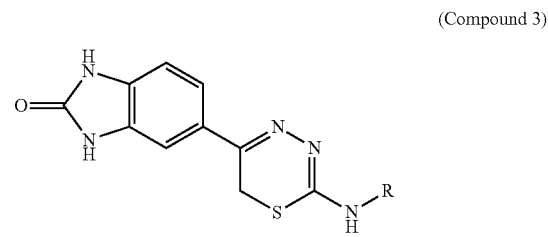

A solution of 5-(2-chloroacetyl)-1H-benzo[d]imidazol-2(3H)-one (Compound 2) (0.47 mmol, 1 equiv.) and N-alkylhydrazinecarbothioamide (1.1 equiv.) in DMF/HOAc (2 mL/0.2 mL) was stirred at room temperature for 12 hours. Upon completion of reaction monitored by LC/MS, the mixture was concentrated under high vacuum to remove solvent and aqueous ammonia solution was added to it. The resulting precipitate was filtered, washed with water and dried under high vacuum to give the desired 1,3,4-thiadiazines (Compound 3).

N-benzyl-5-(benzo[d]imidazol-2(3H)-one)-6H-1,3,4-thiadiazin-2-amine (Compound 3-1)

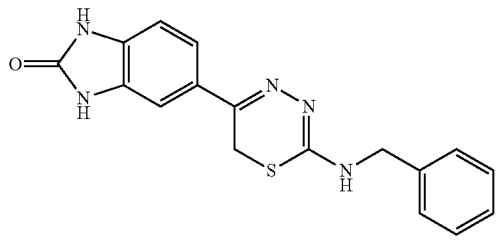
(Compound 3-1)

Yellow solid. Yield 90%. $^1$H-NMR (600 MHz, d$_6$-DMSO): δ 10.76 (s, 1H), 10.75 (s, 1H), 7.51 (s, 1H), 7.45 (m, 2H), 7.34 (m, 3H), 7.24 (m, 1H), 6.95 (d, 1H, J=7.8 Hz), 4.56 (s, 2H), 3.65 (s, 2H); MS (ESI) m/z 338.16 (M+H)+.

N-methyl-5-(benzo[d]imidazol-2(3H)-one)-6H-1,3,4-thiadiazin-2-amine (Compound 3-2)

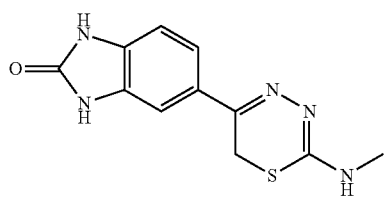
(Compound 3-2)

Yellow solid. Yield 88%. $^1$H-NMR (600 MHz, d$_6$-DMSO): δ 10.79 (s, 1H), 10.78 (s, 1H), 7.48 (s, 1H), 7.46 (m, 2H), 6.97 (d, 1H, J=7.8 Hz), 3.70 (s, 2H), 2.90 (s, 3H); MS (ESI) m/z 262.34 (M+H)+.

N-ethyl-5-(benzo[d]imidazol-2(3H)-one)-6H-1,3,4-thiadiazin-2-amine (Compound 3-3)

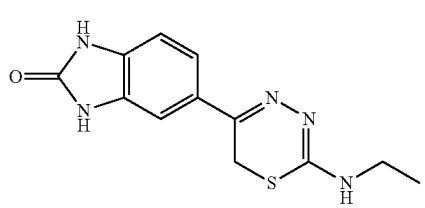
(Compound 3-3)

Yellow solid. Yield 62%. $^1$H-NMR (600 MHz, d$_6$-DMSO): δ 10.77 (s, 1H), 10.76 (s, 1H), 7.47 (s, 1H), 7.46 (m, 2H), 6.97 (d, 1H, J=8.4 Hz), 3.65 (s, 2H), 3.36 (m, 2H), 1.15 (t, 3H, J=7.2 Hz); MS (ESI) m/z 276.32 (M+H)+.

N-propyl-5-(benzo[d]imidazol-2(3H)-one)-6H-1,3,4-thiadiazin-2-amine (Compound 3-4)

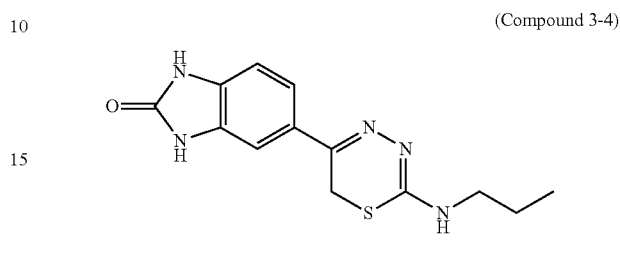
(Compound 3-4)

Yellow solid. Yield 52%. $^1$H-NMR (600 MHz, d$_6$-DMSO): δ 10.77 (s, 1H), 10.76 (s, 1H), 7.47 (s, 1H), 7.46 (m, 2H), 6.97 (d, 1H, J=8.4 Hz), 3.65 (s, 2H), 3.28 (m, 2H), 1.57 (m, 2H), 0.90 (t, 3H, J=7.2 Hz); MS (ESI) m/z 290.46 (M+H)+.

N-butyl-5-(benzo[d]imidazol-2(3H)-one)-6H-1,3,4-thiadiazin-2-amine (Compound 3-5)

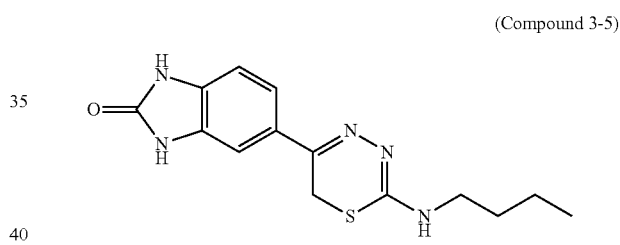
(Compound 3-5)

Yellow solid. Yield 43%. $^1$H-NMR (600 MHz, d$_6$-DMSO): δ 10.75 (s, 2H), 7.47 (s, 1H), 7.45 (m, 2H), 6.96 (d, 1H, J=8.4 Hz), 3.64 (s, 2H), 1.54 (m, 2H), 1.34 (m, 2H), 0.90 (t, 3H, J=7.2 Hz); MS (ESI) m/z 304.71 (M+H)+.

N-isopropyl-5-(benzo[d]imidazol-2(3H)-one)-6H-1,3,4-thiadiazin-2-amine (Compound 3-6)

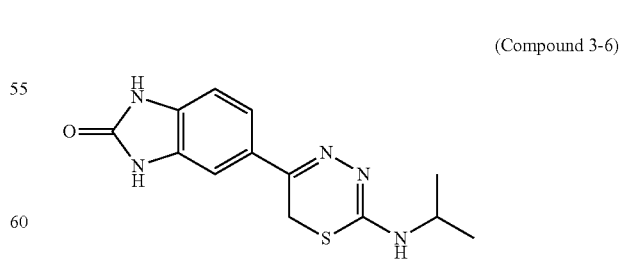
(Compound 3-6)

Yellow solid. Yield 73%. $^1$H-NMR (600 MHz, d$_6$-DMSO): δ 10.77 (s, 1H), 10.76 (s, 1H), 7.47 (s, 1H), 7.46 (m, 2H), 6.96 (d, 1H, J=8.4 Hz), 4.11 (s, 1H), 3.67 (s, 2H), 1.16 (t, 3H, J=6.6 Hz); MS (ESI) m/z 290.35 (M+H)+.

31

N-t-butyl-5-(benzo[d]imidazol-2(3H)-one)-6H-1,3,4-thiadiazin-2-amine (Compound 3-7)

(Compound 3-7)

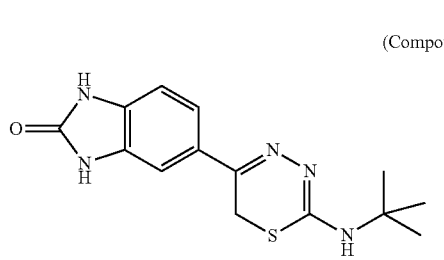

Yellow solid. Yield 79%. $^1$H-NMR (600 MHz, $d_6$-DMSO): δ 10.77 (s, 2H), 7.48 (s, 1H), 7.46 (m, 2H), 6.96 (d, 1H, J=8.4 Hz), 6.48 (s, 1H), 3.61 (s, 2H), 1.40 (s, 9H); MS (ESI) m/z 304.21 (M+H)+.

N-(3-methylbutyl)-5-(benzo[d]imidazol-2(3H)-one)-6H-1,3,4-thiadiazin-2-amine (Compound 3-8)

(Compound 3-8)

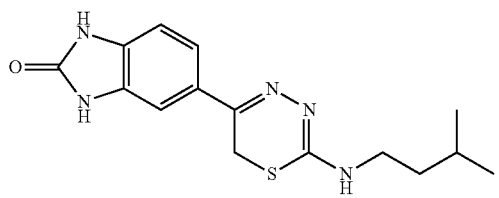

Yellow solid. Yield 68%. $^1$H-NMR (600 MHz, $d_6$-DMSO): δ 10.76 (s, 2H), 7.47 (s, 1H), 7.45 (m, 2H), 6.96 (d, 1H, J=8.4 Hz), 3.65 (s, 2H), 3.36 (m, 1H), 1.63 (m, 2H), 1.46 (m, 2H), 1.34 (m, 2H), 0.90 (d, 6H, J=6.6 Hz); MS (ESI) m/z 318.73 (M+H)+.

N-cyclohexyl-5-(benzo[d]imidazol-2(3H)-one)-6H-1,3,4-thiadiazin-2-amine (Compound 3-9)

(Compound 3-9)

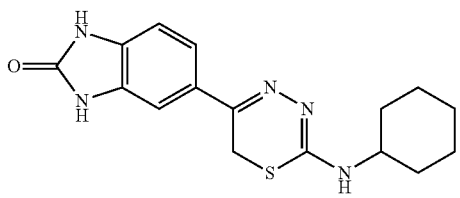

Yellow solid. Yield 80%. $^1$H-NMR (600 MHz, $d_6$-DMSO): δ 10.75 (s, 2H), 7.47 (s, 1H), 7.45 (d, 1H, J=7.8 Hz), 6.95 (d, 1H, J=8.4 Hz), 6.86 (s, 1H), 3.81 (s, 1H), 3.62 (s, 2H), 1.93 (m, 2H), 1.72 (m, 2H), 1.59 (m, 1H), 1.28 (m, 4H), 1.14 (m, 1H); MS (ESI) m/z 331.12 (M+H)+.

32

N-(2-cyclohexylmethyl)-5-(benzo[d]imidazol-2(3H)-one)-6H-1,3,4-thiadiazin-2-amine (Compound 3-10)

(Compound 3-10)

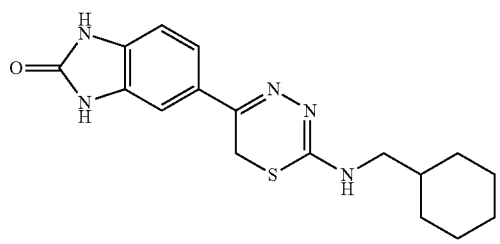

Yellow solid. Yield 45%. $^1$H-NMR (600 MHz, $d_6$-DMSO): δ 10.77 (s, 1H), 10.76 (s, 1H), 7.45 (m, 2H), 6.96 (d, 1H, J=7.8 Hz), 3.66 (s, 2H), 3.18 (m, 2H), 1.67 (m, 6H), 1.20 (m, 3H), 0.92 (m, 2H); MS (ESI) m/z 344.95 (M+H)+.

N-(2-(morpholino)ethyl)-5-(benzo[d]imidazol-2(3H)-one)-6H-1,3,4-thiadiazin-2-amine (Compound 3-11)

(Compound 3-11)

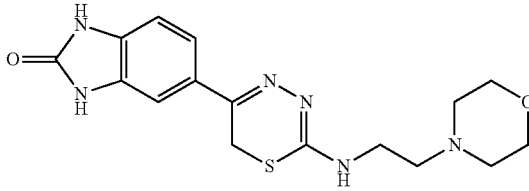

Yellow solid. Yield 44%. $^1$H-NMR (600 MHz, $d_6$-DMSO): δ 10.77 (s, 1H), 10.76 (s, 1H), 7.47 (s, 1H), 7.46 (m, 1H), 6.96 (d, 1H, J=7.8 Hz), 3.65 (m, 2H), 3.58 (m, 4H), 3.46 (m, 2H), 2.52 (m, 2H), 2.42 (m, 4H); MS (ESI) m/z 361.15 (M+H)+.

N-(4-chlorobenzyl)-5-(benzo[d]imidazol-2(3H)-one)-6H-1,3,4-thiadiazin-2-amine (Compound 3-12)

(Compound 3-12)

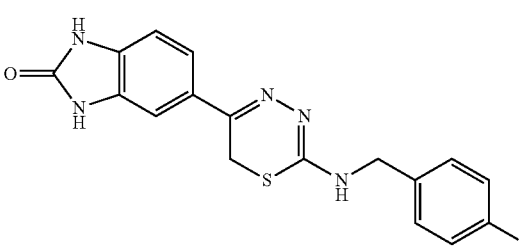

Yellow solid. Yield 53%. $^1$H-NMR (600 MHz, $d_6$-DMSO): δ 10.77 (s, 1H), 10.76 (s, 1H), 7.51 (s, 1H), 7.45 (m, 2H), 7.38 (m, 3H), 6.95 (d, 1H, J=8.4 Hz), 4.53 (s, 2H), 3.65 (s, 1H); MS (ESI) m/z 374.22 (M+H)+.

N-(3-chlorobenzyl)-5-(benzo[d]imidazol-2(3H)-one)-6H-1,3,4-thiadiazin-2-amine (Compound 3-13)

(Compound 3-13)

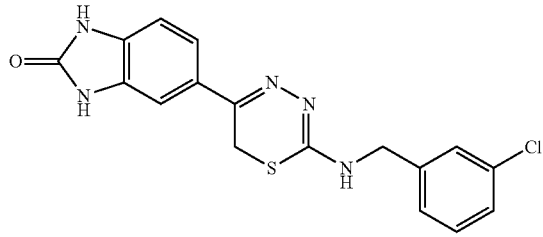

Yellow solid. Yield 49%. ¹H-NMR (600 MHz, d₆-DMSO): δ 10.79 (s, 1H), 10.77 (s, 1H), 7.46 (d, 2H, J=7.2 Hz), 7.41 (s, 1H), 7.36 (d, 1H, J=7.8 Hz), 7.33 (d, 2H, J=6.6 Hz), 6.96 (d, 1H, J=8.4 Hz), 4.56 (s, 2H), 3.72 (s, 2H); MS (ESI) m/z 372.54 (M+H)+.

N-(2-chlorobenzyl)-5-(benzo[d]imidazol-2(3H)-one)-6H-1,3,4-thiadiazin-2-amine (Compound 3-14)

(Compound 3-14)

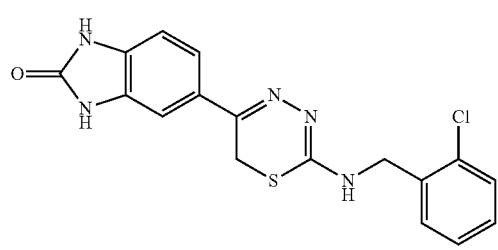

Yellow solid. Yield 57%. ¹H-NMR (600 MHz, d₆-DMSO): δ 10.79 (s, 1H), 10.77 (s, 1H), 7.46 (m, 3H), 7.32 (m, 3H), 6.96 (d, 1H, J=9 Hz), 4.61 (s, 2H), 3.73 (s, 2H); MS (ESI) m/z 372.38 (M+H)+.

N-(4-fluorobenzyl)-5-(benzo[d]imidazol-2(3H)-one)-6H-1,3,4-thiadiazin-2-amine (Compound 3-15)

(Compound 3-15)

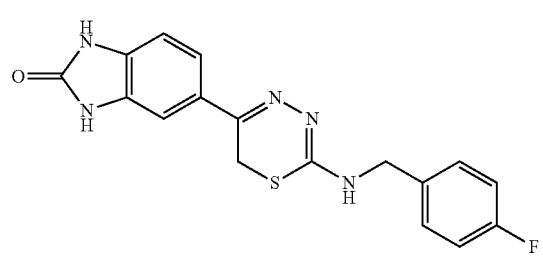

Yellow solid. Yield 36%. ¹H-NMR (600 MHz, d₆-DMSO): δ 10.77 (s, 1H), 10.76 (s, 1H), 7.45 (m, 2H), 7.39 (m, 2H), 7.15 (t, 3H, J=9 Hz), 6.94 (d, 1H, J=8.4 Hz), 4.53 (s, 2H), 3.67 (s, 2H); MS (ESI) m/z 356.83 (M+H)+.

N-(3-fluorobenzyl)-5-(benzo[d]imidazol-2(3H)-one)-6H-1,3,4-thiadiazin-2-amine (Compound 3-16)

(Compound 3-16)

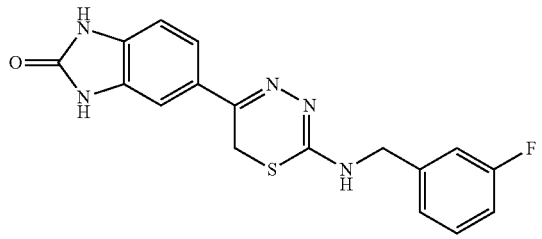

Yellow solid. Yield 62%. ¹H-NMR (600 MHz, d₆-DMSO): δ 10.78 (s, 1H), 10.77 (s, 1H), 7.46 (d, 2H, J=7.2 Hz), 7.38 (m, 1H), 7.17 (m, 2H), 7.08 (m, 1H), 6.96 (d, 1H, J=7.8 Hz), 4.56 (s, 2H), 3.70 (s, 2H); MS (ESI) m/z 356.09 (M+H)+.

N-(2-fluorobenzyl)-5-(benzo[d]imidazol-2(3H)-one)-6H-1,3,4-thiadiazin-2-amine (Compound 3-17)

(Compound 3-17)

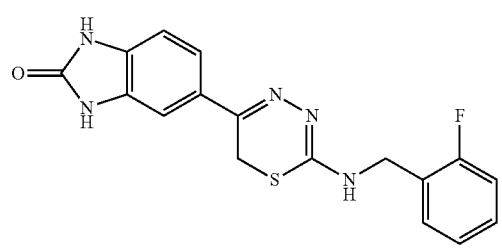

Yellow solid. Yield 44%. ¹H-NMR (600 MHz, d₆-DMSO): δ 10.81 (s, 1H), 10.79 (s, 1H), 7.46 (m, 3H), 7.33 (m, 1H), 7.20 (m, 2H), 6.96 (d, 1H, J=8.4 Hz), 4.61 (s, 2H), 3.76 (s, 2H); MS (ESI) m/z 356.79 (M+H)+.

N-(4-trifluoromethylbenzyl)-5-(benzo[d]imidazol-2(3H)-one)-6H-1,3,4-thiadiazin-2-amine (Compound 3-18)

(Compound 3-18)

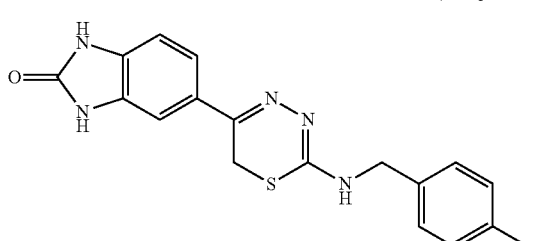

Yellow solid. Yield 33%. ¹H-NMR (600 MHz, d₆-DMSO): δ 10.77 (s, 1H), 10.76 (s, 1H), 7.71 (d, 2H, J=7.8 Hz), 7.56 (d, 2H, J=7.8 Hz), 7.46 (d, 2H, J=7.8 Hz), 6.95 (d, 1H, J=9 Hz), 4.63 (s, 2H), 3.66 (s, 2H); MS (ESI) m/z 406.92 (M+H)+.

N-(3-trifluoromethylbenzyl)-5-(benzo[d]imidazol-2(3H)-one)-6H-1,3,4-thiadiazin-2-amine (Compound 3-19)

(Compound 3-19)

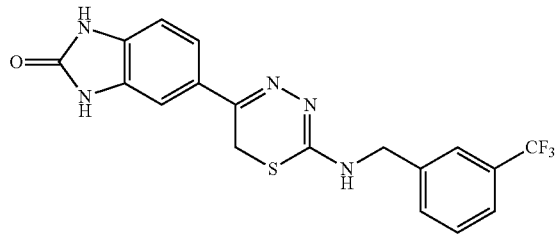

Yellow solid. Yield 54%. $^1$H-NMR (600 MHz, d$_6$-DMSO): δ 10.78 (s, 1H), 10.77 (s, 1H), 7.70 (m, 1H), 7.68 (d, 2H, J=7.2 Hz), 7.61 (m, 2H), 7.46 (m 2H), 6.95 (d, 1H, J=8.4 Hz), 4.64 (s, 2H), 3.68 (s, 2H); MS (ESI) m/z 406.92 (M+H)+.

N-(2-trifluoromethylbenzyl)-5-(benzo[d]imidazol-2(3H)-one)-6H-1,3,4-thiadiazin-2-amine (Compound 3-20)

(Compound 3-20)

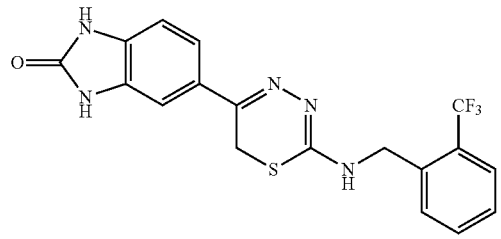

Yellow solid. Yield 23%. $^1$H-NMR (600 MHz, d$_6$-DMSO): δ 10.78 (s, 1H), 10.77 (s, 1H), 7.73 (d, 1H, J=7.8 Hz), 7.67 (d, 2H, J=7.2 Hz), 7.61 (m, 1H), 7.48 (m 2H), 6.95 (d, 1H, J=8.4 Hz), 4.75 (s, 2H), 3.72 (s, 2H); MS (ESI) m/z 406.71 (M+H)+.

N-(4-cyanobenzyl)-5-(benzo[d]imidazol-2(3H)-one)-6H-1,3,4-thiadiazin-2-amine (Compound 3-21)

(Compound 3-21)

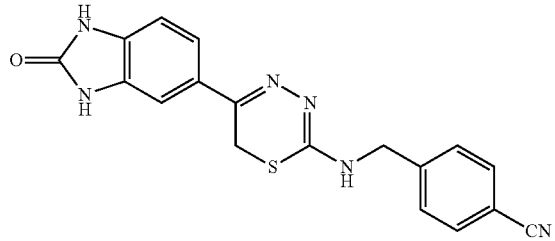

Yellow solid. Yield 45%. $^1$H-NMR (600 MHz, d$_6$-DMSO): δ 10.77 (s, 1H), 10.76 (s, 1H), 7.81 (d, 2H, J=8.4 Hz), 7.65 (s, 1H), 7.54 (d, 2H, J=7.8 Hz), 7.46 (m, 2H), 6.94 (d, 1H, J=8.4 Hz), 4.62 (s, 2H), 3.67 (s, 2H); MS (ESI) m/z 363.77 (M+H)+.

N-(3-cyanobenzyl)-5-(benzo[d]imidazol-2(3H)-one)-6H-1,3,4-thiadiazin-2-amine (Compound 3-22)

(Compound 3-22)

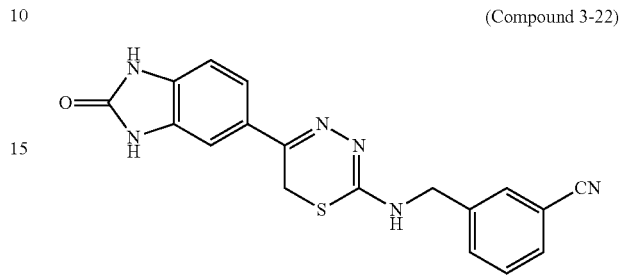

Yellow solid. Yield 45%. $^1$H-NMR (600 MHz, d$_6$-DMSO): δ 10.77 (s, 1H), 10.74 (s, 1H), 7.79 (s, 1H), 7.72 (m, 2H), 7.56 (t, 1H, J=7.8 Hz), 7.46 (m, 2H), 6.96 (d, 1H, J=8.4 Hz), 4.59 (s, 2H), 3.71 (s, 2H); MS (ESI) m/z 363.81 (M+H)+.

N-(pyridine-3yl)methyl-5-(benzo[d]imidazol-2(3H)-one)-6H-1,3,4-thiadiazin-2-amine (Compound 3-23)

(Compound 3-23)

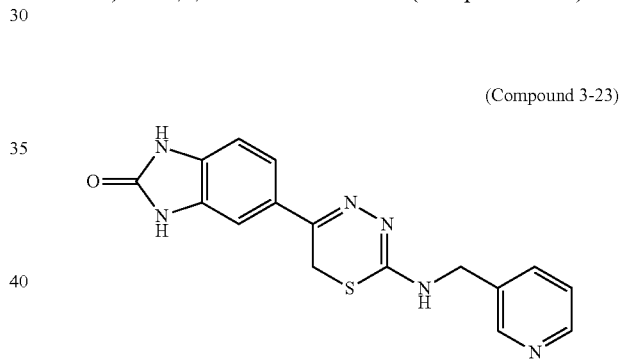

Yellow solid. Yield 43%. $^1$H-NMR (600 MHz, d$_6$-DMSO): δ 10.77 (s, 1H), 10.76 (s, 1H), 8.57 (s, 1H), 8.45 (s, 1H), 7.76 (d, 1H, J=6.6 Hz), 7.57 (s, 1H), 7.46 (m, 1H), 7.36 (m, 1H), 6.96 (d, 1H, J=8.4 Hz), 4.57 (s, 2H), 3.66 (s, 2H); MS (ESI) m/z 339.16 (M+H)+.

N-(pyridine-4yl)methyl-5-(benzo[d]imidazol-2(3H)-one)-6H-1,3,4-thiadiazin-2-amine (Compound 3-24)

(Compound 3-24)

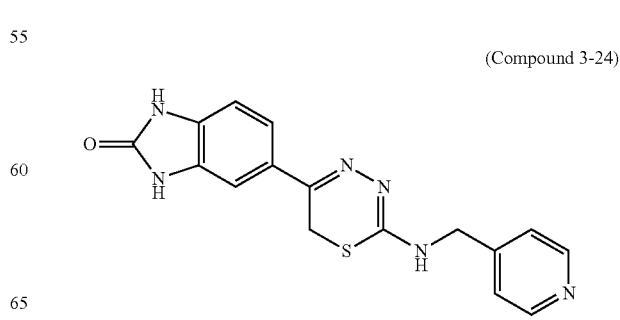

Yellow solid. Yield 34%. $^1$H-NMR (600 MHz, d$_6$-DMSO): δ 10.77 (s, 1H), 10.76 (s, 1H), 8.51 (m, 2H), 7.46 (m, 2H), 7.34 (m, 2H), 6.96 (d, 1H, J=9 Hz), 4.56 (s, 2H), 3.70 (s, 2H); MS (ESI) m/z 339.11 (M+H)+.

General Procedure for the Synthesis of Compound 4. To a solution of 3-24 or 3-(0.091 mmol) in DMSO (1 mL) was added 50% hydrogen peroxide solution (0.013 mL) at 0° C. followed by potassium carbonate (0.015 eq.). The reaction mixture was allowed to warm up to room temperature and stirred overnight. Upon the completion of reaction, the reaction mixture was vacuum dried and purified using flash chromatography with mixture of MeOH/DCM/NH$_3$ (10:89:1) as eluent to get the final product as yellow solid.

N-(4-carboxyaminobenzyl)-5-(benzo[d]imidazol-2(3H)-one)-6H-1,3,4-thiadiazin-2-amine (Compound 4-1)

(Compound 4-1)

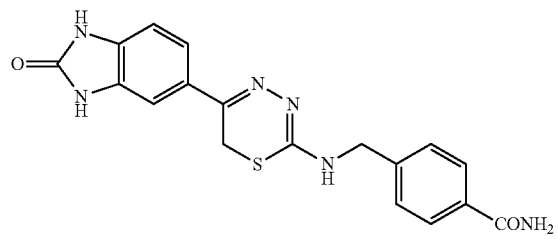

Yellow solid. Yield 14%. $^1$H-NMR (600 MHz, d$_6$-DMSO): δ 10.77 (s, 1H), 10.76 (s, 1H), 7.92 (m, 2H), 7.84 (m, 2H), 7.46 (m, 2H), 7.40 (m, 2H), 7.30 (m, 1H), 6.94 (d, 1H, J=7.8 Hz), 4.59 (s, 2H), 3.68 (s, 2H); MS (ESI) m/z 381.11 (M+H)+.

N-(3-carboxyaminobenzyl)-5-(benzo[d]imidazol-2(3H)-one)-6H-1,3,4-thiadiazin-2-amine (Compound 4-2)

(Compound 4-2)

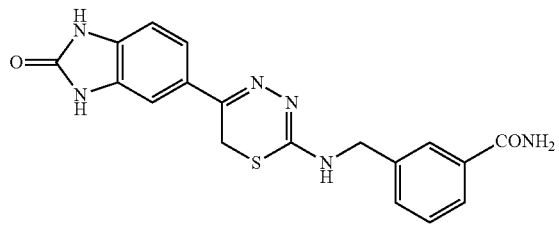

Yellow solid. Yield 42%. $^1$H-NMR (600 MHz, d$_6$-DMSO): δ 10.77 (s, 1H), 10.76 (s, 1H), 7.95 (m, 2H), 7.86 (m, 1H), 7.75 (m, 1H), 7.51 (m, 1H), 7.47 (m, 2H), 7.40 (m, 1H), 7.34 (m, 1H), 6.96 (d, 1H, J=7.8 Hz), 4.59 (s, 2H), 3.68 (s, 2H); MS (ESI) m/z 381.11 (M+H)+.

N-(1-phenylethyl)-5-(benzo[d]imidazol-2(3H)-one)-6H-1,3,4-thiadiazin-2-amine (Compound 3-25)

(Compound 3-25)

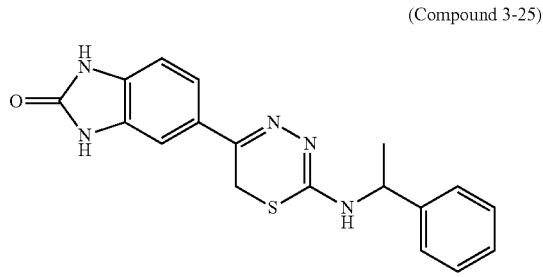 [SMILES: CC(NC1=NN=C(c2ccc3[nH]c(=O)[nH]c3c2)CS1)c1ccccc1]

Yellow solid. Yield 41%. $^1$H-NMR (600 MHz, d$_6$-DMSO): δ 10.76 (s, 1H), 10.75 (s, 1H), 7.42 (m, 2H), 7.36 (d, 2H, J=7.2 Hz), 7.32 (m, 2H), 7.21 (m, 1H), 6.94 (d, 1H, J=7.8 Hz), 5.20 (s, 1H), 3.72 (s, 1H), 3.52 (s, 1H), 1.43 (d, 3H, J=7.2 Hz); MS (ESI) m/z 352.79 (M+H)+.

N-(1-(4-fluorophenyl)ethyl)-5-(benzo[d]imidazol-2(3H)-one)-6H-1,3,4-thiadiazin-2-amine (Compound 3-26)

(Compound 3-26)

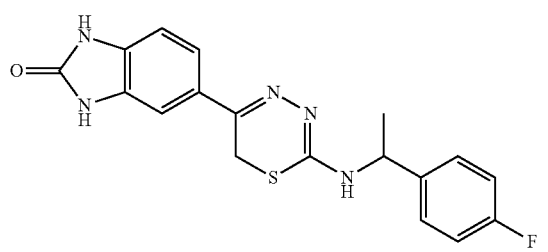

Yellow solid. Yield 41%. $^1$H-NMR (600 MHz, d$_6$-DMSO): δ 10.82 (s, 1H), 10.80 (s, 1H), 7.43 (m, 4H), 7.17 (m, 2 Hz), 6.96 (d, 1H, J=8.4 Hz), 5.15 (s, 1H), 3.81 (m, 1H), 3.67 (m, 1H), 1.44 (d, 3H, J=6.6 Hz); MS (ESI) m/z 370.72 (M+H)+.

N-(3-cyano-4-fluoro-benzyl)-5-(benzo[d]imidazol-2(3H)-one)-6H-1,3,4-thiadiazin-2-amine (Compound 3-27)

(Compound 3-27)

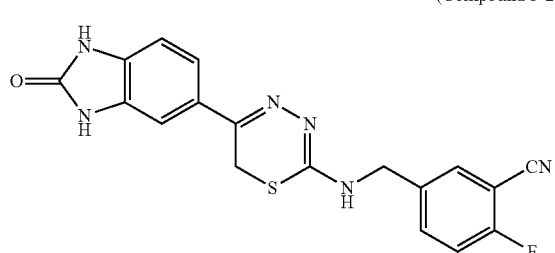

Yellow solid. Yield 48%. $^1$H-NMR (600 MHz, d$_6$-DMSO): δ 10.78 (s, 1H), 10.77 (s, 1H), 7.88 (m, 1H), 7.77 (m, 1H), 7.51 (t, 1H, J=9 Hz), 7.46 (m, 2H), 6.95 (d, 1H, J=9 Hz), 4.56 (s, 2H), 3.70 (s, 2H); MS (ESI) m/z 381.30 (M+H)+.

N-phenyl-5-(benzo[d]imidazol-2(3H)-one)-6H-1,3,4-thiadiazin-2-amine (Compound 3-28)

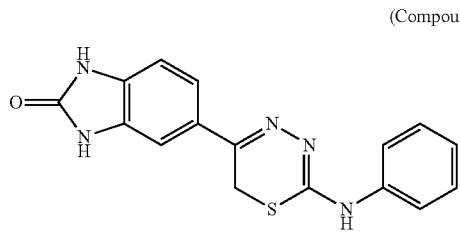

(Compound 3-28)

Yellow solid. Yield 66%. ¹H-NMR (600 MHz, d₆-DMSO): δ 10.82 (s, 1H), 10.80 (s, 1H), 7.39 (m, 2H), 7.30 (m, 2H), 7.02 (m, 2H), 6.96 (m, 1H), 6.83 (m, 2H), 3.89 (s, 2H); MS (ESI) m/z 324.67 (M+H)+.

N-(3-fluorophenyl)-5-(benzo[d]imidazol-2(3H)-one)-6H-1,3,4-thiadiazin-2-amine (Compound 3-29)

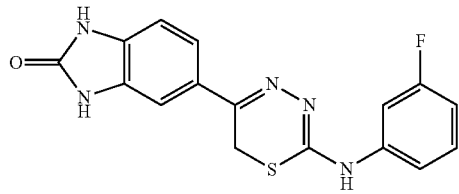

(Compound 3-29)

Yellow solid. Yield 69%. ¹H-NMR (600 MHz, d₆-DMSO): δ 10.83 (s, 1H), 10.81 (s, 1H), 7.49 (m, 2H), 7.30 (m, 2H), 7.36 (m, 2H), 7.05 (m, 1H), 6.98 (d, 1H, J=7.2 Hz), 6.66 (m, 1H), 3.91 (s, 2H); MS (ESI) m/z 342.41 (M+H)+.

N-(3-trifluoromethylphenyl)-5-(benzo[d]imidazol-2(3H)-one)-6H-1,3,4-thiadiazin-2-amine (Compound 3-30)

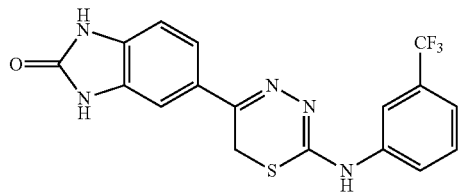

(Compound 3-30)

Yellow solid. Yield 74%. ¹H-NMR (600 MHz, d₆-DMSO): δ 10.84 (s, 1H), 10.82 (s, 1H), 7.54 (m, 2H), 7.36 (m, 2H), 7.15 (m, 2H), 6.98 (d, 1H, J=7.8 Hz), 3.92 (s, 2H); MS (ESI) m/z 392.36 (M+H)+.

N-(3-cyanophenyl)-5-(benzo[d]imidazol-2(3H)-one)-6H-1,3,4-thiadiazin-2-amine (Compound 3-31)

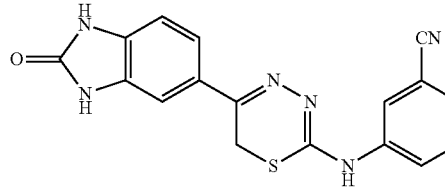

(Compound 3-31)

Yellow solid. Yield 68%. ¹H-NMR (600 MHz, d₆-DMSO): δ 10.84 (s, 1H), 10.81 (s, 1H), 7.51 (m, 3H), 7.41 (m, 2H), 7.17 (m, 2H), 6.98 (d, 1H, J=7.2 Hz), 3.94 (s, 2H); MS (ESI) m/z 349.12 (M+H)+.

N-(4-fluorophenyl)-5-(benzo[d]imidazol-2(3H)-one)-6H-1,3,4-thiadiazin-2-amine (Compound 3-32)

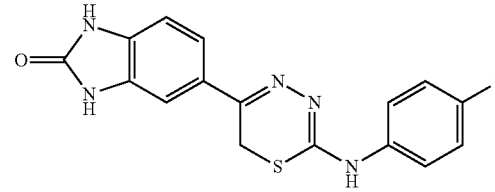

(Compound 3-32)

Yellow solid. Yield 74%. ¹H-NMR (600 MHz, d₆-DMSO): δ 10.82 (s, 1H), 10.79 (s, 1H), 7.41 (m, 3H), 7.13 (t, 2H, J=9 Hz), 6.98 (d, 1H, J=7.8 Hz), 6.84 (m, 1H), 3.89 (s, 2H); MS (ESI) m/z 342.43 (M+H)+.

N-(4-fluorophenyl)-5-(benzo[d]imidazol-2(3H)-one)-6H-1,3,4-thiadiazin-2-amine (Compound 3-33)

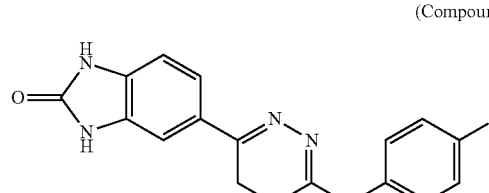

(Compound 3-33)

Yellow solid. Yield 67%. ¹H-NMR (600 MHz, d₆-DMSO): δ 10.82 (s, 1H), 10.80 (s, 1H), 7.82 (m, 1H), 7.58 (m, 1H), 7.38 (m, 3H), 6.98 (d, 1H, J=7.8 Hz), 6.84 (m, 1H), 3.89 (s, 2H); MS (ESI) m/z 358.44 (M+H)+.

N-(2-phenylethyl)-5-(benzo[d]imidazol-2(3H)-one)-6H-1,3,4-thiadiazin-2-amine (Compound 3-34)

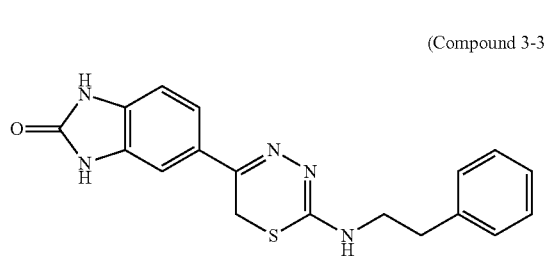
(Compound 3-34)

Yellow solid. Yield 60%. $^1$H-NMR (600 MHz, d$_6$-DMSO): δ 10.78 (s, 1H), 10.77 (s, 1H), 7.48 (m, 2H), 7.30 (m, 2H), 7.26 (m, 2H), 7.21 (m, 1H), 6.96 (d, 1H, J=8.4 Hz), 3.69 (s, 2H), 3.56 (m, 2H), 2.89 (m, 2H); MS (ESI) m/z 352.71 (M+H)+.

N-(2-(4-fluorophenyl)ethyl)-5-(benzo[d]imidazol-2(3H)-one)-6H-1,3,4-thiadiazin-2-amine (Compound 3-35)

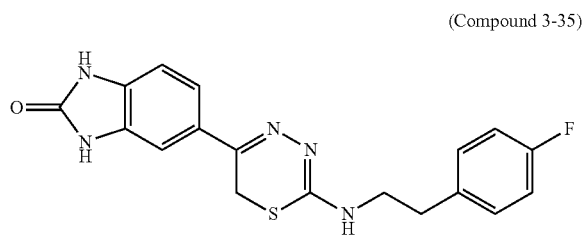 [SMILES: O=c1[nH]c2ccc(C3=NN=C(NCCc4ccc(F)cc4)SC3)cc2[nH]1]
(Compound 3-35)

Yellow solid. Yield 43%. $^1$H-NMR (600 MHz, d$_6$-DMSO): δ 10.78 (s, 1H), 10.77 (s, 1H), 7.48 (m, 2H), 7.29 (m, 2H), 7.13 (t, 2H, J=8.4 Hz), 6.96 (d, 1H, J=8.4 Hz), 3.68 (s, 2H), 3.54 (m, 2H), 2.88 (t, 2H, J=7.2 Hz); MS (ESI) m/z 370.21 (M+H)+.

N-(2-(4-chlorophenyl)ethyl)-5-(benzo[d]imidazol-2(3H)-one)-6H-1,3,4-thiadiazin-2-amine (Compound 3-36)

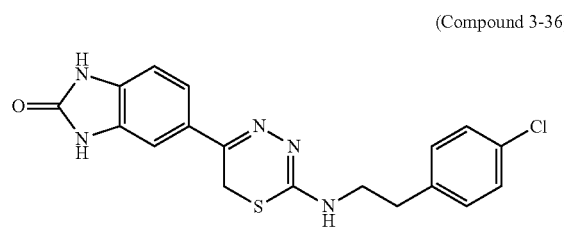
(Compound 3-36)

Yellow solid. Yield 60%. $^1$H-NMR (600 MHz, d$_6$-DMSO): δ 10.78 (s, 1H), 10.77 (s, 1H), 7.48 (m, 2H), 7.36 (d, 2H, J=8.4 Hz), 7.29 (d, 2H, J=8.4 Hz), 6.96 (d, 1H, J=7.8 Hz), 3.69 (s, 2H), 3.55 (m, 2H), 2.90 (t, 2H, J=7.2 Hz); MS (ESI) m/z 386.30 (M+H)+.

N-(3-phenylpropyl)-5-(benzo[d]imidazol-2(3H)-one)-6H-1,3,4-thiadiazin-2-amine (Compound 3-37)

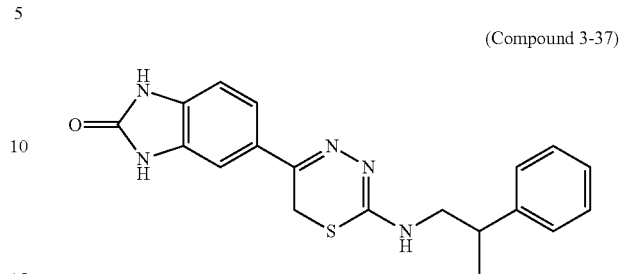
(Compound 3-37)

Yellow solid. Yield 41%. $^1$H-NMR (600 MHz, d$_6$-DMSO): δ 11.03 (s, 1H), 10.98 (s, 1H), 7.51 (d, 1H, J=8.4 Hz), 7.46 (s, 1H), 7.32 (m, 3H), 7.24 (m, 1H), 7.05 (d, 1H, J=8.4 Hz), 4.15 (s, 2H), 3.68 (s, 2H), 3.16 (m, 1H), 1.28 (d, 3H, J=6.6 Hz); MS (ESI) m/z 366.99 (M+H)+.

N-(2-(pyridine-1-yl)ethyl)-5-(benzo[d]imidazol-2(3H)-one)-6H-1,3,4-thiadiazin-2-amine (Compound 3-38)

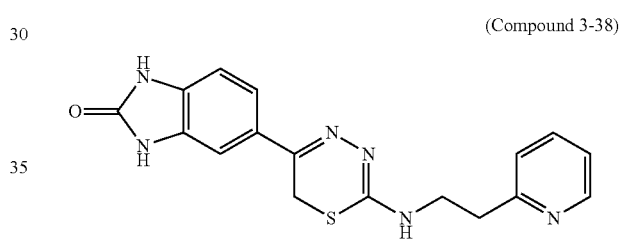
(Compound 3-38)

Yellow solid. Yield 44%. $^1$H-NMR (600 MHz, d$_6$-DMSO): δ 10.77 (s, 1H), 10.76 (s, 1H), 8.51 (d, 1H, J=4.8 Hz), 7.71 (m, 1H), 7.47 (m, 2H), 7.22 (t, 1H, J=4.8 Hz), 6.94 (d, 1H, J=8.4 Hz), 3.65 (m, 2H), 3.04 (t, 2H, J=7.2 Hz); MS (ESI) m/z 353.45 (M+H)+.

N-(2-(pyridine-3-yl)ethyl)-5-(benzo[d]imidazol-2(3H)-one)-6H-1,3,4-thiadiazin-2-amine (Compound 3-39)

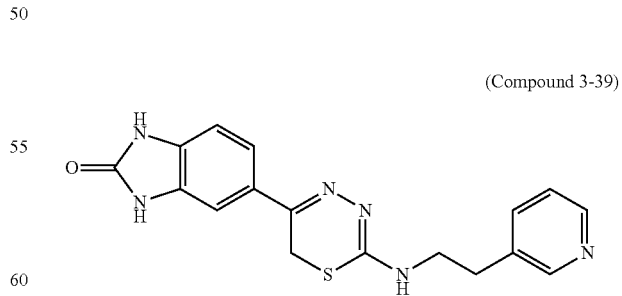
(Compound 3-39)

Yellow solid. Yield 25%. $^1$H-NMR (600 MHz, d$_6$-DMSO): δ 10.75 (s, 2H), 8.46 (s, 1H), 8.42 (m, 1H), 7.68 (d, 1H, J=7.2 Hz), 7.46 (m, 2H), 7.33 (m, 1H), 6.94 (d, 1H, J=8.4 Hz), 3.65 (m, 2H), 3.58 (m, 2H), 2.91 (t, 2H, J=7.2 Hz); MS (ESI) m/z 353.14 (M+H)+.

N-(2-naphthylmethyl)-5-(benzo[d]imidazol-2(3H)-one)-6H-1,3,4-thiadiazin-2-amine (Compound 3-40)

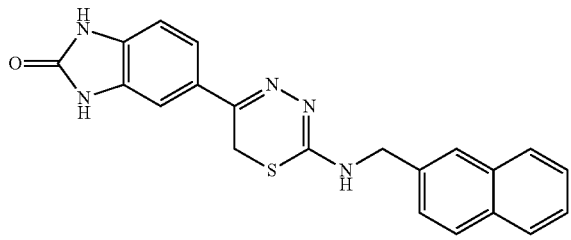

(Compound 3-40)

Yellow solid. Yield 39%. $^1$H-NMR (600 MHz, d$_6$-DMSO): δ 10.78 (s, 1H), 10.76 (s, 1H), 7.88 (m, 3H), 7.84 (m, 1H), 7.49 (m, 3H), 7.48 (m, 5H), 6.96 (d, 1H, J=8.4 Hz), 4.73 (s, 2H), 3.70 (s, 2H); MS (ESI) m/z 388.77 (M+H)+.

N-(1-naphthylmethyl)-5-(benzo[d]imidazol-2(3H)-one)-6H-1,3,4-thiadiazin-2-amine (Compound 3-41)

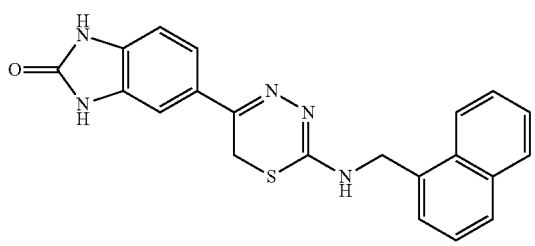

(Compound 3-41)

Yellow solid. Yield 75%. $^1$H-NMR (600 MHz, d$_6$-DMSO): δ 10.78 (s, 1H), 10.76 (s, 1H), 8.11 (d, 1H, J=8.4 Hz), 7.95 (m, 1H), 7.86 (d, 1H, J=7.8 Hz), 7.56 (m, 3H), 7.48 (m, 3H), 6.96 (d, 1H, J=7.8 Hz), 5.03 (s, 2H), 3.70 (s, 2H); MS (ESI) m/z 388.76 (M+H)+.

N-(1-naphthyl)-5-(benzo[d]imidazol-2(3H)-one)-6H-1,3,4-thiadiazin-2-amine (Compound 3-42)

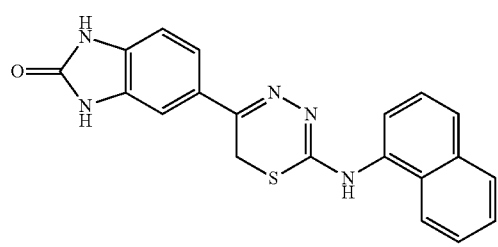

(Compound 3-42)

Yellow solid. Yield 56%. $^1$H-NMR (600 MHz, d$_4$-Methanol): δ 11.52 (s, 1H), 10.82 (s, 1H), 10.79 (s, 1H), 8.00 (d, 1H, J=7.8 Hz), 7.89 (d, 1H, J=7.8 Hz), 7.61 (d, 1H, J=7.8 Hz), 7.49 (m, 2H), 7.42 (m, 3H), 6.96 (d, 1H, J=7.8 Hz), 6.82 (s, 1H), 3.91 (s, 2H); MS (ESI) m/z 374.84 (M+H)+.

5-(2-(cyclopropylamino)-6H-1,3,4-thiadiazin-5-yl)-1H-benzo[d]imidazol-2(3H)-one (Compound 3-43)

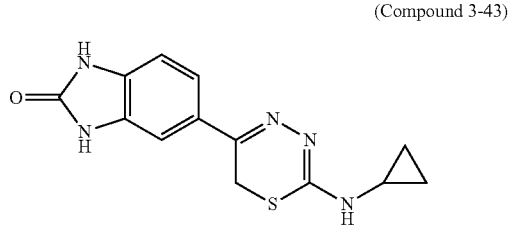 [SMILES: O=c1[nH]c2ccc(C3=NN=C(NC4CC4)SC3)cc2[nH]1]

(Compound 3-43)

Yellow solid. Yield 86%. $^1$H-NMR (600 MHz, d$_6$-DMSO): δ 10.76 (m, 2H), 7.42 (m, 2H), 6.94 (d, 1H, J=7.3 Hz), 3.70 (s, 2H), 2.76 (s, 1H), 0.67 (m, 2H), 0.47 (m, 2H); MS (ESI) m/z 288.0997 (M+H)+.

5-(2-(cyclopentylamino)-6H-1,3,4-thiadiazin-5-yl)-1H-benzo[d]imidazol-2(3H)-one (Compound 3-44)

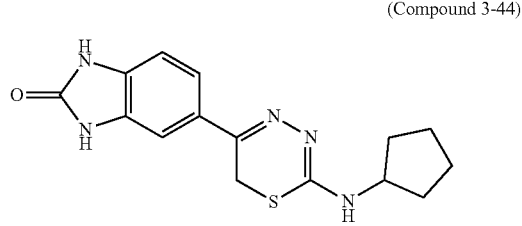 [SMILES: O=c1[nH]c2ccc(C3=NN=C(NC4CCCC4)SC3)cc2[nH]1]

(Compound 3-44)

Yellow solid. Yield 83%. $^1$H-NMR (600 MHz, d$_6$-DMSO): δ 10.74 (m, 2H), 7.45 (m, 2H), 6.94 (m, 2H), 4.23 (m, 1H), 3.62 (s, 2H), 1.87 (s, 2H), 1.65 (m, 2H), 1.50 (m, 4H); MS (ESI) m/z 316.1362 (M+H)+.

5-(2-(cyclobutylamino)-6H-1,3,4-thiadiazin-5-yl)-1H-benzo[d]imidazol-2(3H)-one (Compound 3-45)

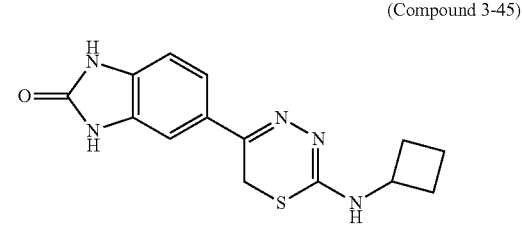 [SMILES: O=c1[nH]c2ccc(C3=NN=C(NC4CCC4)SC3)cc2[nH]1]

(Compound 3-45)

Yellow solid. Yield 81%. $^1$H-NMR (600 MHz, d$_6$-DMSO): δ 10.75 (m, 2H), 7.44 (m, 2H), 7.25 (br, 1H), 6.94 (d, 1H, J=8.5 Hz), 4.38 (br, 1H), 3.62 (s, 2H), 2.22 (m, 2H), 1.95 (m, 2H), 1.64 (m, 2H); MS (ESI) m/z 302.1182 (M+H)+.

5-(2-((cyclobutylmethyl)amino)-6H-1,3,4-thiadiazin-5-yl)-1H-benzo[d]imidazol-2(3H)-one (Compound 3-46)

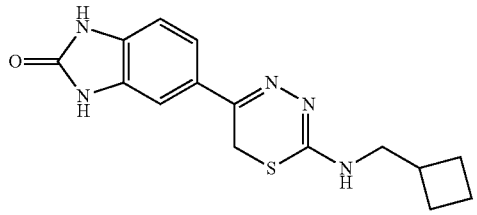
(Compound 3-46)

Yellow solid. Yield 75%. $^1$H-NMR (600 MHz, d$_6$-DMSO): δ 10.75 (s, 2H), 7.45 (m, 2H), 6.96 (m, 2H), 3.62 (s, 2H), 3.36 (s, 2H), 2.56 (s, 1H), 2.00 (m, 2H), 1.82 (m, 2H), 1.69 (m, 2H); MS (ESI) m/z 316.1139 (M+H)+.

5-(2-((cyclopropylmethyl)amino)-6H-1,3,4-thiadiazin-5-yl)-1H-benzo[d]imidazol-2(3H)-one (Compound 3-47)

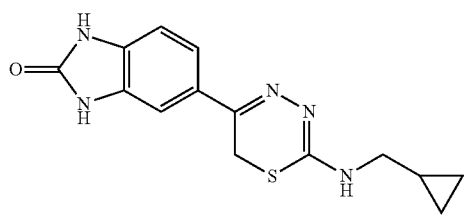
(Compound 3-47)

Yellow solid. Yield 41%. $^1$H-NMR (600 MHz, d$_6$-DMSO): δ 10.74 (s, 2H), 7.45 (m, 2H), 7.09 (br, 1H), 6.94 (d, 1H, J=8.5 Hz), 3.63 (s, 2H), 3.19 (s, 2H), 1.08 (s, 1H), 0.43 (m, 2H), 0.20 (m, 2H), 1.69 (m, 2H); MS (ESI) m/z 302.1102 (M+H)+.

5-(2-((cyclopentylmethyl)amino)-6H-1,3,4-thiadiazin-5-yl)-1H-benzo[d]imidazol-2(3H)-one (Compound 3-48)

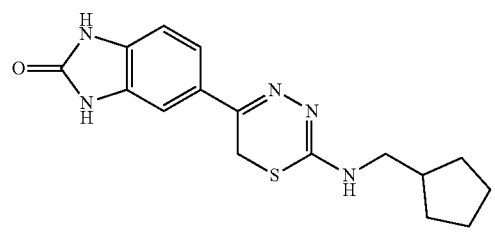
(Compound 3-48)

Yellow solid. Yield 59%. $^1$H-NMR (600 MHz, d$_6$-DMSO): δ 10.75 (s, 2H), 7.45 (m, 2H), 7.05 (br, 1H), 6.94 (d, 1H, J=8.5 Hz), 3.64 (s, 2H), 3.24 (s, 2H), 2.18 (m, 1H), 1.69 (m, 2H), 1.57 (m, 2H), 1.49 (m, 2H), 1.22 (m, 2H); MS (ESI) m/z 330.1456 (M+H)+.

5-(2-((2-cyclopentylethyl)amino)-6H-1,3,4-thiadiazin-5-yl)-1H-benzo[d]imidazol-2(3H)-one (Compound 3-49)

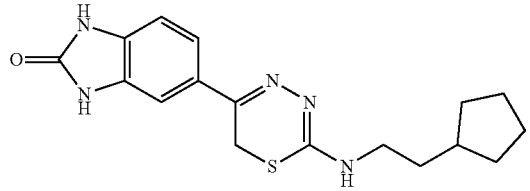
(Compound 3-49)

Yellow solid. Yield 65%. $^1$H-NMR (600 MHz, d$_6$-DMSO): δ 10.75 (s, 2H), 7.45 (m, 2H), 6.70 (m, 2H), 3.64 (s, 2H), 3.34 (s, 2H), 1.75 (m, 3H), 1.56 (m, 4H), 1.48 (m, 2H), 1.09 (m, 2H); MS (ESI) m/z 344.1815 (M+H)+.

5-(2-((3-morpholinopropyl)amino)-6H-1,3,4-thiadiazin-5-yl)-1H-benzo[d]imidazol-2(3H)-one (Compound 3-50)

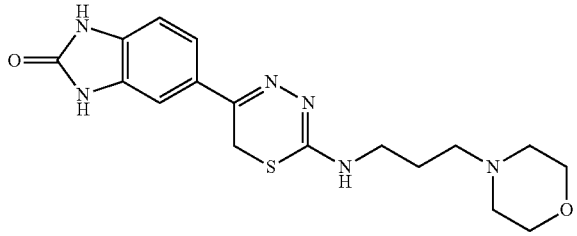
(Compound 3-50)

Brown solid. Yield 21%. $^1$H-NMR (600 MHz, d$_6$-DMSO): δ 10.75 (m, 2H), 7.45 (m, 2H), 7.00 (br, 1H), 6.70 (m, 2H), 6.95 (d, 1H, J=8.5 Hz), 3.60 (m, 6H), 3.35 (s, 2H), 2.34 (m, 6H), 1.72 (m, 2H); MS (ESI) m/z 375.1600 (M+H)+.

5-(2-((3-(dimethylamino)propyl)amino)-6H-1,3,4-thiadiazin-5-yl)-1H-benzo[d]imidazol-2(3H)-one (Compound 3-51)

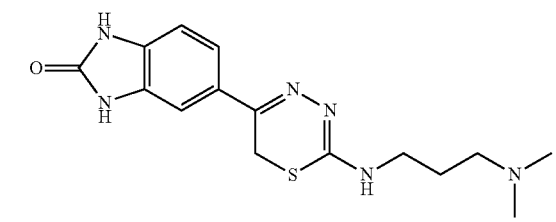
(Compound 3-51)

Brown solid. Yield 57%. $^1$H-NMR (600 MHz, d$_6$-DMSO): δ 10.76 (m, 2H), 7.45 (m, 2H), 7.00 (m, 2H), 3.65 (s, 2H), 3.35 (m, 6H), 2.28 (m, 6H), 1.74 (m, 2H); MS (ESI) m/z 375.1600 (M+H)+.

5-(2-(((tetrahydrofuran-2-yl)methyl)amino)-6H-1,3,
4-thiadiazin-5-yl)-1H-benzo[d]imidazol-2(3H)-one
(Compound 3-52)

(Compound 3-52)

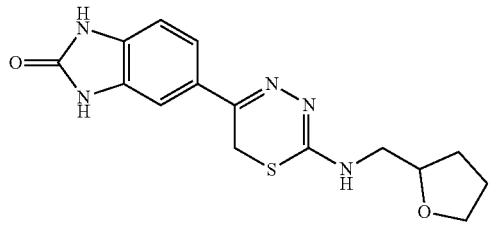

Yellow solid. Yield 60%. $^1$H-NMR (600 MHz, $d_6$-DMSO): δ 10.76 (m, 2H), 7.45 (m, 2H), 6.95 (d, 1H, J=7.3 Hz), 4.03 (m, 1H), 3.64 (m, 3H), 3.38 (s, 2H), 1.91 (m, 1H), 1.82 (m, 2H), 1.57 (m, 1H); MS (ESI) m/z 332.1184 (M+H)+.

5-(2-((2-(dimethylamino)ethyl)amino)-6H-1,3,4-
thiadiazin-5-yl)-1H-benzo[d]imidazol-2(3H)-one
(Compound 3-53)

(Compound 3-53)

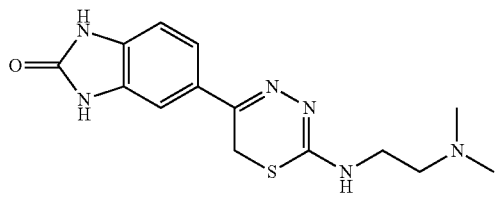

Yellow solid. Yield 34%. $^1$H-NMR (600 MHz, $d_6$-DMSO): δ 10.77 (m, 2H), 7.48 (m, 2H), 6.96 (d, 1H, J=8.5 Hz), 6.89 (br, 1H), 3.65 (m, 2H), 3.45 (s, 2H), 3.31 (s, 2H), 2.21 (s, 6H); MS (ESI) m/z 319.1354 (M+H)+.

5-(2-((2-(dimethylamino)ethyl)amino)-6H-1,3,4-
thiadiazin-5-yl)-1H-benzo[d]imidazol-2(3H)-one
(Compound 3-54)

(Compound 3-54)

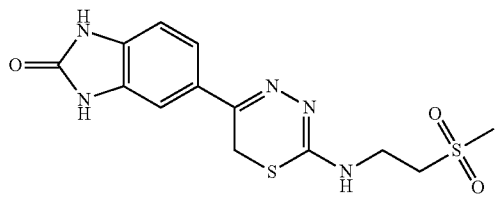

Yellow solid. Yield 64%. $^1$H-NMR (600 MHz, $d_6$-DMSO): δ 10.77 (s, 2H), 7.47 (m, 2H), 7.23 (br, 1H), 6.95 (d, 1H, J=7.3 Hz), 3.69 (m, 4H), 3.43 (m, 2H), 3.03 (s, 3H); MS (ESI) m/z 354.0693 (M+H)+.

5-(2-((2-(dimethylamino)ethyl)amino)-6H-1,3,4-
thiadiazin-5-yl)-1H-benzo[d]imidazol-2(3H)-one
(Compound 3-55)

(Compound 3-55)

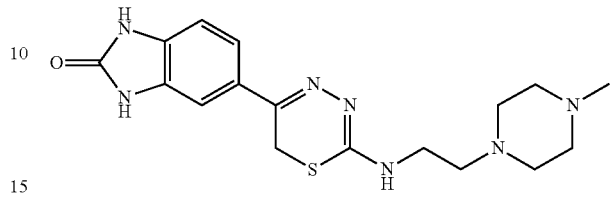

Yellow solid. Yield 52%. $^1$H-NMR (600 MHz, $d_4$-Methanol): δ 7.53 (s, 1H), 7.46 (d, 1H, J=8.5 Hz), 7.09 (d, 1H, J=8.5 Hz), 3.63 (s, 2H), 3.55 (t, 1H, J=6.1 Hz), 2.49 (m, 10), 2.23 (s, 3H); MS (ESI) m/z 374.1752 (M+H)+.

5-(2-((2-(dimethylamino)ethyl)amino)-6H-1,3,4-
thiadiazin-5-yl)-1H-benzo[d]imidazol-2(3H)-one
(Compound 3-56)

(Compound 3-56)

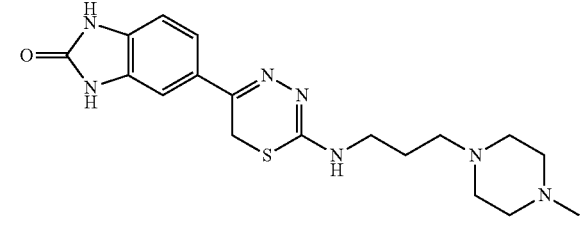

Yellow solid. Yield 47%. $^1$H-NMR (600 MHz, $d_4$-Methanol): δ 7.54 (s, 1H), 7.48 (d, 1H, J=8.5 Hz), 7.04 (d, 1H, J=8.5 Hz), 3.66 (s, 2H), 3.46 (t, 1H, J=7.3 Hz), 2.61 (m, 10H), 2.33 (s, 3H), 1.83 (m, 2H); MS (ESI) m/z 388.1905 (M+H)+.

5-(2-((2-(piperidin-1-yl)ethyl)amino)-6H-1,3,4-thiadiazin-5-yl)-1H-benzo[d]imidazol-2(3H)-one (Compound 3-57)

(Compound 3-57)

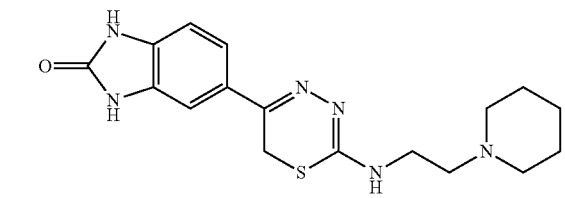

Yellow solid. Yield 57%. $^1$H-NMR (600 MHz, $d_6$-DMSO): δ 10.77 (m, 2H), 7.47 (s, 1H), 7.45 (d, 1H, J=7.3 Hz), 6.95 (d, 1H, J=8.5 Hz), 3.65 (s, 2H), 3.45 (s, 2H), 3.33 (s, 3H), 1.45 (m, 8H); MS (ESI) m/z 359.1669 (M+H)+.

5-(2-((2-methoxyethyl)amino)-6H-1,3,4-thiadiazin-5-yl)-1H-benzo[d]imidazol-2(3H)-one (Compound 3-58)

(Compound 3-58)

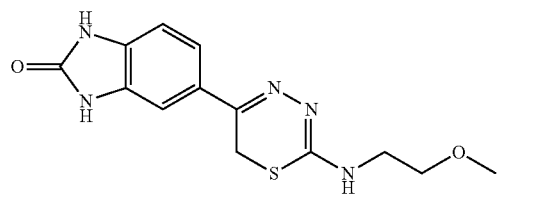

Yellow solid. Yield 56%. $^1$H-NMR (600 MHz, $d_4$-Methanol): δ 7.61 (s, 1H), 7.56 (d, 1H, J=8.5 Hz), 7.12 (d, 1H, J=8.5 Hz), 3.74 (s, 2H), 3.64 (m, 4H), 3.40 (s, 3H); MS (ESI) m/z 306.1024 (M+H)+.

5-(2-((3-methoxypropyl)amino)-6H-1,3,4-thiadiazin-5-yl)-1H-benzo[d]imidazol-2(3H)-one (Compound 3-59)

(Compound 3-59)

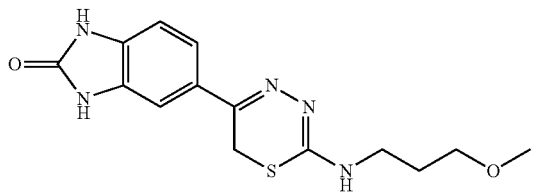

Yellow solid. Yield 59%. $^1$H-NMR (600 MHz, $d_4$-Methanol): δ 7.56 (m, 2H), 7.10 (s, 1H), 3.69 (s, 2H), 3.50 (m, 4H), 3.34 (s, 3H), 1.90 (s, 2H); MS (ESI) m/z 320.1195 (M+H)+.

General Procedure for the Synthesis of Compound 6

(Compound 6)

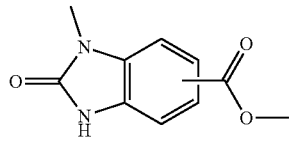

To a solution of Compounds 5-1 or 5-2 (2.78 mmol, 1 equiv.) in THF (20 mL) was added 1,1'-carbonyldiimidazole (4.16 mmol, 1.5 equiv.). The reaction mixture was stirred at room temperature for 16 h. After being quenched with water, the aqueous layer was extracted with EtOAc (2×40 mL). The combined organic extracts were washed with brine, dried over anhydrous $Na_2SO_4$, filtered, and concentrated. The residue was purified using flash chromatography with mixture of EtOAc/hexane (30:70) as eluent to afford Compounds 6.

Methyl 1-methyl-2-oxo-2,3-dihydro-1H-benzo[d]imidazole-5-carboxylate (Compound 6-1)

(Compound 6-1)

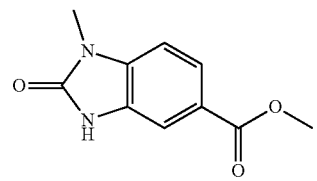

Gray solid. Yield 83%. $^1$H-NMR (600 MHz, $d_4$-Methanol): δ 7.84 (d, 1H, J=8.5 Hz), 7.69 (d, 1H, J=2.4 Hz), 7.17 (d, 1H, J=8.5 Hz), 3.89 (s, 3H), 3.41 (s, 3H); MS (ESI) m/z 207.0753 (M+H)+.

Methyl 3-methyl-2-oxo-2,3-dihydro-1H-benzo[d]imidazole-5-carboxylate (Compound 6-2)

(Compound 6-2)

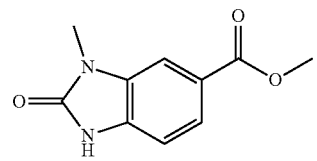

Pale yellow solid. Yield 92%. $^1$H-NMR (600 MHz, $CDCl_3$): δ 9.36 (s, 1H), 7.88 (d, 1H, J=8.5 Hz), 7.72 (s, 1H), 7.15 (d, 1H, J=7.3 Hz), 3.96 (s, 3H), 3.50 (s, 3H); MS (ESI) m/z 207.0768 (M+H)+.

General Procedure for the Synthesis of Compound 7

(Compound 7)

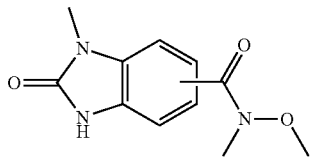

To a solution of Compounds 6-1 or 6-2 (1.46 mmol, 1 equiv.) in THF/$H_2O$ (5/1.5 mL) was added lithiumhydroxide (4.36 mmol, 3 equiv.). The reaction was stirred at 60° C. for 16 h. After cool down, the reaction mixture was adjusted to pH 2 by 1 N HCl. The solvent was removed and the crude product was used in next step without further purification. The crude product was dissolved in DMF (15 mL) then N,O-dimethylhydroxylamine hydrochloride (2.18 mmol, 1.5 equiv.), HATU (1.75 mmol, 1.2 equiv.), and $Et_3N$ (0.61 mL, 3 equiv.) were added. The reaction was stirred at room temperature for 16 h. After being quenched with water, the aqueous layer was extracted with EtOAc (2×40 mL). The combined organic extracts were washed with brine, dried over anhydrous $Na_2SO_4$, filtered, and concentrated. The residue was purified using flash chromatography with mixture of DCM/MeOH (95:5) as eluent to give Compounds 7.

N-methoxy-N,1-dimethyl-2-oxo-2,3-dihydro-1H-benzo[d]imidazole-5-carboxamide (Compound 7-1)

(Compound 7-1)

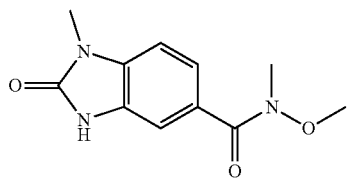

Black solid. Yield 73% over two steps. $^1$H-NMR (600 MHz, CDCl$_3$): δ 9.99 (s, 1H), 7.54 (m, 2H), 6.98 (d, 1H, J=7.3 Hz), 3.55 (s, 3H), 3.45 (s, 3H), 3.37 (s, 3H); MS (ESI) m/z 236.1030 (M+H)+.

N-methoxy-N,3-dimethyl-2-oxo-2,3-dihydro-1H-benzo[d]imidazole-5-carboxamide (Compound 7-2)

(Compound 7-2)

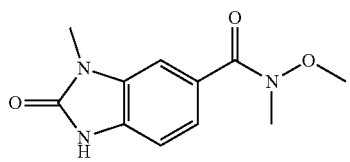

Yellow solid. Yield 27% over two steps. $^1$H-NMR (600 MHz, CDCl$_3$): δ 11.02 (s, 1H), 7.50 (d, 1H, J=6.1 Hz), 7.40 (s, 1H), 7.11 (d, 1H, J=8.5 Hz), 3.56 (s, 3H), 3.42 (s, 3H), 3.37 (s, 3H); MS (ESI) m/z 236.1035 (M+H)+.

General Procedure for the Synthesis of Compound 8

(Compound 8)

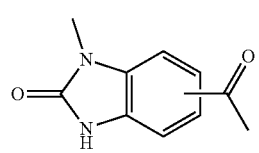

To a solution of Compound 7 (0.15 mmol, 1 equiv.) in THF (1.5 mL) was added 3 M MeMgCl (0.44 mmol, 3 equiv.) at 0° C. A temperature was slowly increased to room temperature. The reaction was stirred for 2 h. After being quenched with aq. NH$_4$Cl, the aqueous layer was extracted with EtOAc (2×10 mL). The combined organic extracts were washed with brine, dried over anhydrous Na$_2$SO$_4$, filtered, and concentrated. The residue was purified using flash chromatography with mixture of EtOAc/hexane (80:20) as eluent to give Compounds 8.

5-acetyl-1-methyl-1H-benzo[d]imidazol-2(3H)-one (Compound 8-1)

(Compound 8-1)

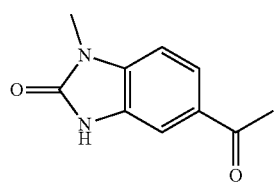

Yellow solid. Yield 55%. $^1$H-NMR (600 MHz, CDCl$_3$): δ 7.76 (d, 1H, J=8.5 Hz), 7.69 (s, 1H), 6.99 (d, 1H, J=8.5 Hz), 3.44 (s, 3H), 2.60 (s, 3H); MS (ESI) m/z 191.0804 (M+H)+.

6-acetyl-1-methyl-1H-benzo[d]imidazol-2(3H)-one (Compound 8-2)

(Compound 8-2)

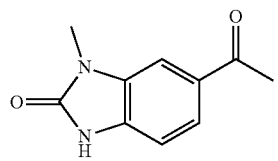

Yellow solid. Yield 95%. $^1$H-NMR (600 MHz, CDCl$_3$): δ 8.80 (s, 1H), 7.78 (d, 1H, J=7.3 Hz), 7.68 (s, 1H), 7.13 (d, 1H, J=8.5 Hz), 3.50 (s, 3H), 2.66 (s, 3H); MS (ESI) m/z 191.0820 (M+H)+.

General Procedure for the Synthesis of Compound 9

(Compound 9)

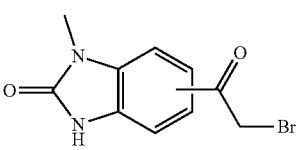

A solution of Compound 8 (0.35 mmol, 1 equiv.) and CuBr$_2$ (0.70 mmol, 2 equiv.) in DCM/EtOAc/EtOH (1/1/1 mL) was refluxed for 16 h. The solvent was removed in vacuo and the crude product was purified using flash chromatography with mixture of EtOAc/hexane (80:20) as eluent to give Compounds 9.

5-(2-bromoacetyl)-1-methyl-1H-benzo[d]imidazol-2(3H)-one (Compound 9-1)

(Compound 9-1)

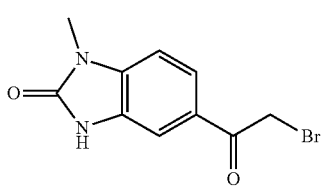

Brown solid. Yield 32%. ¹H-NMR (600 MHz, d₄-Methanol): δ 7.87 (d, 1H, J=9.8 Hz), 7.70 (s, 1H), 7.21 (d, 1H, J=8.5 Hz), 4.62 (s, 2H), 3.43 (s, 3H); MS (ESI) m/z 268.9970, 270.9885 (M+H)+.

6-(2-bromoacetyl)-1-methyl-1H-benzo[d]imidazol-2 (3H)-one (Compound 9-2)

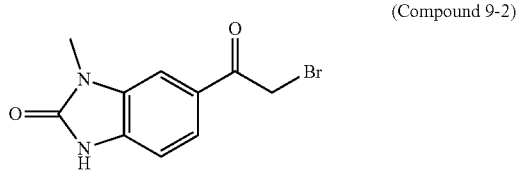
(Compound 9-2)

White solid. Yield 58%. ¹H-NMR (600 MHz, d₄-Methanol): δ 7.77 (d, 1H, J=8.5 Hz), 7.66 (s, 1H), 7.11 (d, 1H, J=8.5 Hz), 4.46 (s, 2H), 3.47 (s, 3H); MS (ESI) m/z 268.9923, 270.9896 (M+H)+.

N-methoxy-N,2-dimethyl-1H-benzo[d]imidazole-6-carboxamide (Compound 11)

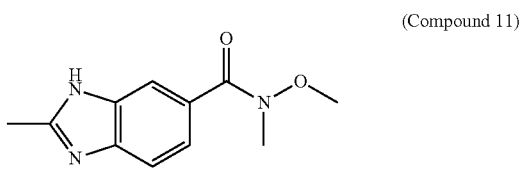
(Compound 11)

Compound 10 (0.57 mmol, 1 equiv.) was suspended in SOCl₂ (2 mL). The reaction was purged with nitrogen then refluxed for 18 h. SOCl₂ was removed in vacuo. The crude product was dissolved in DCM (4 mL) then N,O-dimethylhydroxylamine hydrochloride (0.74 mmol, 1.3 equiv.) and Et₃N (2.27 mmol, 4 equiv.) were added. The reaction mixture was stirred at 55° C. for 5 h. After being quenched with water, the aqueous layer was extracted with DCM (2×10 mL). The combined organic extracts were washed with brine, dried over anhydrous Na₂SO₄, filtered, and concentrated. The residue was purified using flash chromatography with mixture of DCM/MeOH (95:5 to 90:10) as eluent to give Compounds 11 (29.5 mg, 24%) as a yellow oil. ¹H-NMR (600 MHz, CD₃Cl): δ 10.75 (br, 1H), 7.87 (s, 1H), 7.52 (d, 1H, J=7.3 Hz), 7.43 (d, 1H, J=7.3 Hz), 3.56 (s, 3H), 3.38 (s, 3H), 2.54 (s, 3H); MS (ESI) m/z 220.1085 (M+H)+.

1-(2-methyl-1H-benzo[d]imidazol-6-yl)ethenone (Compound 12)

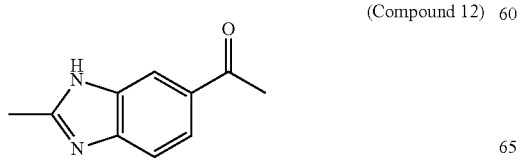
(Compound 12)

To a solution of Compound 11 (0.27 mmol, 1 equiv.) in THF (3 mL) was added 3 M MeMgCl (0.82 mmol, 3 equiv.) at 0° C. A temperature was slowly increased to room temperature. The reaction was stirred for 3 h. After being quenched with aq. NH₄Cl, the aqueous layer was extracted with EtOAc (2×15 mL). The combined organic extracts were washed with brine, dried over anhydrous Na₂SO₄, filtered, and concentrated. The residue was purified using flash chromatography with mixture of DCM/MeOH (95:5 to 90:10) as eluent to afford Compounds 12 (23.6 mg, 49%) as a white solid. ¹H-NMR (600 MHz, CD₃Cl): δ 8.16 (s, 1H), 7.85 (d, 1H, J=8.5 Hz), 7.53 (d, 1H, J=8.5 Hz), 6.15 (br, 1H), 2.64 (s, 3H), 2.63 (s, 3H); MS (ESI) m/z 175.0872 (M+H)+.

General Procedure for the Synthesis of Compound 13

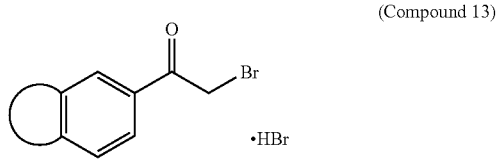
(Compound 13)

To a solution of HBr (0.15 mmol, 1.07 equiv.) in AcOH (1 mL) was added Compound 12 (0.14 mmol, 1 equiv). A solution of Br₂ (0.14 mmol, 1.01 equiv.) in AcOH (0.18 mL) was added. The reaction was stirred at 40° C. for 30 min then the reaction was cooled in an ice-bath. Trituration with EtOAc (3 mL) afforded Compound 13.

2-bromo-1-(2-methyl-1H-benzo[d]imidazol-6-yl) ethenone hydrobromide (Compound 13-1)

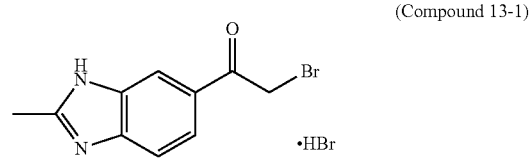
(Compound 13-1)

White solid. Yield 88%. MS (ESI) m/z 252.9970, 254.9955 (M+H)+.

1-(1H-benzo[d]imidazol-6-yl)-2-bromoethanone hydrobromide (Compound 13-2)

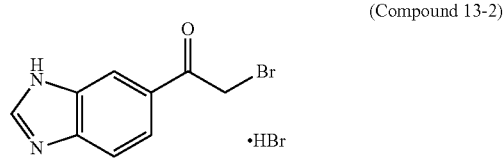 [SMILES: O=C(CBr)c1ccc2nc[nH]c2c1 ; Br]
(Compound 13-2)

Brown solid. Quantitative Yield. MS (ESI) m/z 238.9814, 240.9796 (M+H)+.

Compounds 14-1 to 14-8 were synthesized following the procedure for Compound 3.

5-(2-((4-fluorobenzyl)amino)-6H-1,3,4-thiadiazin-5-yl)-1-methyl-1H-benzo[d]imidazol-2(3H)-one (Compound 14-1)

(Compound 14-1)

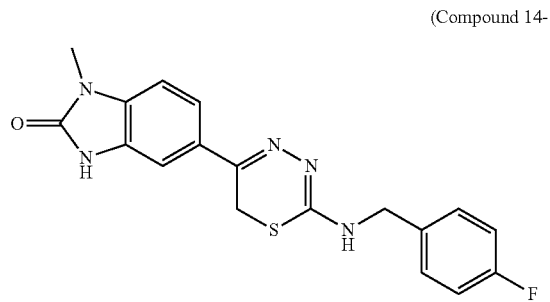

Yellow solid. Yield 37%. $^1$H-NMR (600 MHz, d$_6$-DMSO): δ 10.99 (s, 1H), 7.54 (m, 3H), 7.38 (m, 1H), 7.14 (m, 3H), 4.53 (d, 2H, J=4.9 Hz), 3.67 (s, 2H), 3.29 (s, 3H); MS (ESI) m/z 370.1137 (M+H)+.

5-(2-(benzylamino)-6H-1,3,4-thiadiazin-5-yl)-1-methyl-1H-benzo[d]imidazol-2(3H)-one (Compound 14-2)

(Compound 14-2)

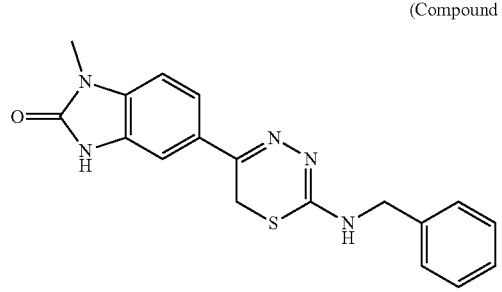

Pale yellow solid. Yield 99%. $^1$H-NMR (600 MHz, d$_4$-Methanol): δ 7.62 (m, 2H), 7.37 (m, 4H), 7.29 (m, 1H), 7.18 (d, 1H, J=8.5 Hz), 4.67 (s, 2H), 3.90 (s, 2H), 3.41 (s, 3H); MS (ESI) m/z 352.1235 (M+H)+.

6-(2-((4-fluorobenzyl)amino)-6H-1,3,4-thiadiazin-5-yl)-1-methyl-1H-benzo[d]imidazol-2(3H)-one (Compound 14-3)

(Compound 14-3)

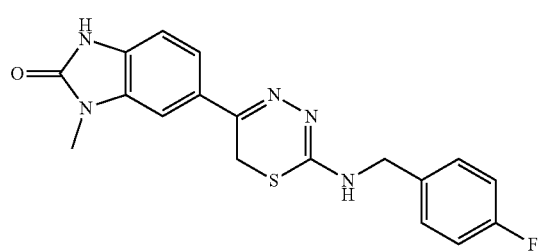

Pale yellow solid. Yield 93%. $^1$H-NMR (600 MHz, d$_6$-DMSO): δ 11.23 (s, 1H), 7.62 (s, 1H), 7.59 (d, 1H, J=8.5 Hz), 7.45 (m, 2H), 7.24 (m, 2H), 7.01 (d, 1H, J=7.3 Hz), 4.68 (s, 2H), 4.25 (s, 2H), 3.32 (s, 3H); MS (ESI) m/z 370.1566 (M+H)+.

6-(2-(benzylamino)-6H-1,3,4-thiadiazin-5-yl)-1-methyl-1H-benzo[d]imidazol-2(3H)-one (Compound 14-4)

(Compound 14-4)

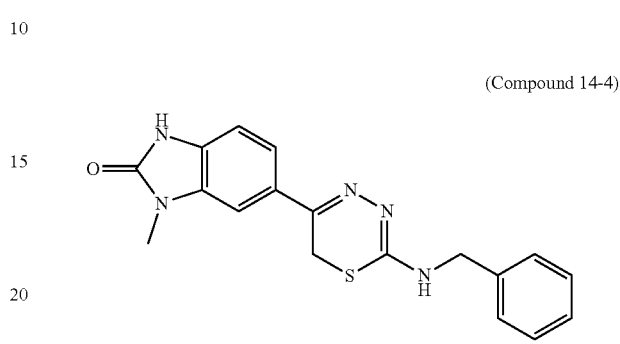

Yellow solid. Yield 34%. $^1$H-NMR (600 MHz, d$_6$-DMSO): δ 11.26 (s, 1H), 7.63 (s, 1H), 7.59 (d, 1H, J=8.5 Hz), 7.41 (m, 5H), 7.12 (d, 1H, J=7.3 Hz), 4.73 (s, 2H), 4.31 (s, 2H), 3.32 (s, 3H); MS (ESI) m/z 352.1239 (M+H)+.

N-(4-fluorobenzyl)-5-(2-methyl-1H-benzo[d]imidazol-6-yl)-6H-1,3,4-thiadiazin-2-amine (Compound 14-5)

(Compound 14-5)

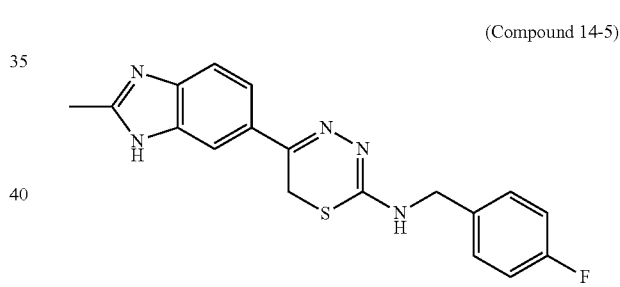

Yellow solid. Yield 79%. $^1$H-NMR (600 MHz, d$_6$-DMSO): δ 8.13 (m, 1H), 7.95 (m, 1H), 7.80 (m, 1H), 7.43 (m, 2H), 7.22 (m, 2H), 4.68 (s, 2H), 4.29 (s, 2H), 2.71 (s, 3H); MS (ESI) m/z 354.1186 (M+H)+.

N-benzyl-5-(2-methyl-1H-benzo[d]imidazol-6-yl)-6H-1,3,4-thiadiazin-2-amine (Compound 14-6)

(Compound 14-6)

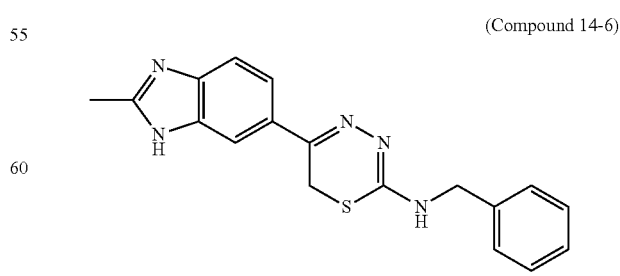

Yellow solid. Yield 51%. $^1$H-NMR (600 MHz, d$_6$-DMSO): δ 7.93 (s, 1H), 7.72 (d, 1H, J=7.3 Hz), 7.47 (d, 1H, J=8.5 Hz), 7.34 (m, 4H), 7.24 (t, 1H, J=7.3 Hz), 4.56 (s, 2H), 3.76 (s, 2H), 3.32 (s, 3H); MS (ESI) m/z 336.1273 (M+H)+.

5-(1H-benzo[d]imidazol-6-yl)-N-(4-fluorobenzyl)-6H-1,3,4-thiadiazin-2-amine (Compound 14-7)

(Compound 14-7)

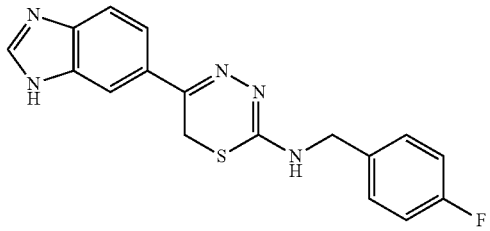

Yellow solid. Yield 66%. $^1$H-NMR (600 MHz, $d_6$-DMSO): δ 8.26 (s, 1H), 8.01 (s, 1H), 7.89 (s, 1H), 7.49 (s, 2H), 7.28 (m, 2H), 7.17 (s, 1H), 4.75 (s, 2H), 4.39 (s, 2H); MS (ESI) m/z 340.1031 (M+H)+.

5-(1H-benzo[d]imidazol-6-yl)-N-benzyl-6H-1,3,4-thiadiazin-2-amine (Compound 14-8)

(Compound 14-8)

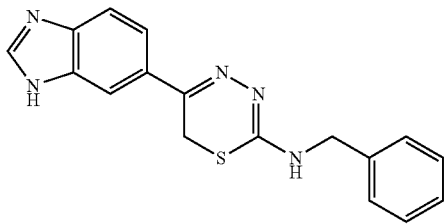

Yellow solid. Yield 99%. $^1$H-NMR (600 MHz, $d_6$-DMSO): δ 8.28 (s, 1H), 8.07 (s, 1H), 7.83 (s, 1H), 7.62 (s, 1H), 7.34 (m, 4H), 7.25 (s, 1H), 4.58 (s, 2H), 3.83 (s, 2H); MS (ESI) m/z 322.1127 (M+H)+.

Example 1—Evaluation of In Vitro DYRK1A Activity

Compound 1, a 1,3,4-thiadiazine compound identified in a screening assay, was evaluated for testing of in vitro DYRK1A activity at 30 μM concentration at Life Technologies using a FRET-based LanthaScreen® Eu Kinase Binding Assay. Compound 1 had an $IC_{50}$ of 9.41 μM against DYRK1A ($K_d$ of 7.5 μM against DYRK1A). This data was confirmed by a second assay, KINOMEscan® (Fabian et al., "A Small Molecule-kinase Interaction Map for Clinical Kinase Inhibitors," *Nat. Biotechnol.* 23(3):329-336 (2005), which is incorporated by reference in its entirety), which measures DYRK1A binding. The results obtained were consistent with those of the Life Technologies inhibition assay with the $K_d$ of 7.3 μM for Compound 1 in the DiscoverX assay.

Example 2—Hit-to-Lead Optimization and Structure-Activity Relationship Studies (SAR)

The structure of the 1,3,4-thiadiazine (Compound 1) (HCl salt) was confirmed by independent synthesis (FIG. 1) and comparison to a commercially purchased sample. NMR, LC-MS, and biological data confirmed the identity of Compound 1 in all aspects. The neutral analog of Compound 1 (Compound 3-1, non-salt) was found to have comparable DYRK1A activity with $K_d$ of 4.5 μM ($IC_{50}$=4.32 μM) (Table 1). With a novel scaffold in hand, a hit-to-lead SAR study was conducted to improve Compound 1's DYRK1A binding potency and studies to further explore its predicted binding mode. Systematic structural modifications were introduced at the 2-amino position, keeping the rest of the molecule intact.

TABLE 1

Binding Affinity at 30 μM and $K_d$'s of the Thiadiazine DYRK1A Inhibitors

| Compound | R | Screening (30 μM) LifeTech[a] | Screening (30 μM) DiscoverX[b] | $K_d$ (nM)[c] |
|---|---|---|---|---|
| 1 | benzyl, HCl salt | 43 | 81 | 7300 (9415)[d] |
| 3-1 | benzyl | — | — | 4500 (9415)[d] |
| 3-2 | methyl | 63 | 0.5 | — |
| 3-3 | ethyl | 69 | 0 | — |
| 3-4 | n-propyl | 48 | 2.9 | — |
| 3-5 | n-butyl | 24 | 0 | — |
| 3-6 | isopropyl | 59 | 2.3 | — |
| 3-7 | tert-butyl | 46 | 0.75 | — |
| 3-8 | isobutyl | 33 | 0.6 | 3400 |
| 3-9 | cyclohexyl | 47 | 22 | 3100 |
| 3-10 | cyclohexylmethyl | 92 | 2.5 | 650 |

TABLE 1-continued
Binding Affinity at 30 μM and K$_d$'s of the Thiadiazine DYRK1A Inhibitors
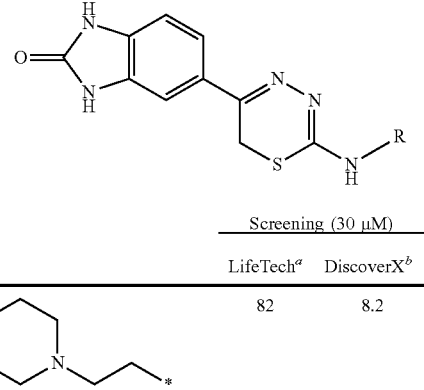
| Com- pound | R | Screening (30 μM) LifeTech[a] | DiscoverX[b] | K$_d$ (nM)[c] |
|---|---|---|---|---|
| 3-11 | 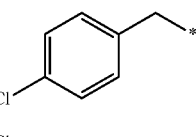 | 82 | 8.2 | 1100 |
| 3-12 | 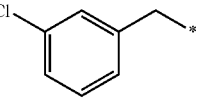 | 93 | 19 | 185 |
| 3-13 | 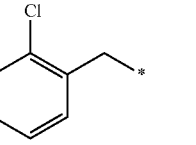 | — | — | 420 |
| 3-14 | 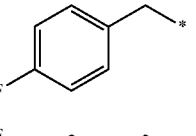 | — | — | 840 |
| 3-15 | 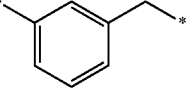 | 95 | 8.9 | 71 |
| 3-16 | 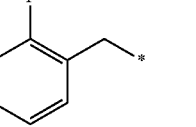 | — | — | 900 |
| 3-17 | 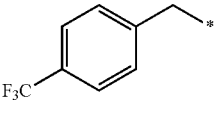 | — | — | 810 |
| 3-18 | 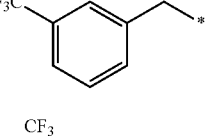 | 53 | 40 | 13000 |
| 3-19 | 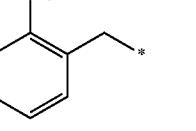 | 20 | 23 | 660 |
| 3-20 | 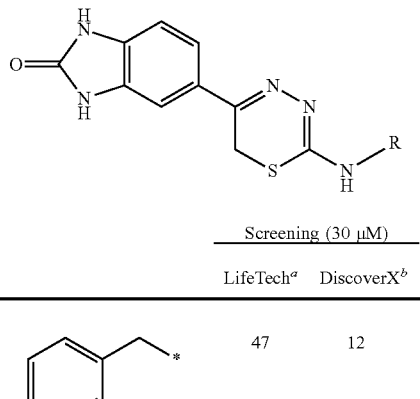 | 24 | 38 | 7700 |
TABLE 1-continued
Binding Affinity at 30 μM and K$_d$'s of the Thiadiazine DYRK1A Inhibitors
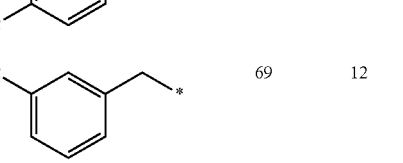
| Com- pound | R | Screening (30 μM) LifeTech[a] | DiscoverX[b] | K$_d$ (nM)[c] |
|---|---|---|---|---|
| 3-21 | 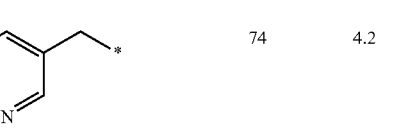 | 47 | 12 | 6200 |
| 3-22 |  | 69 | 12 | 320 |
| 3-23 | 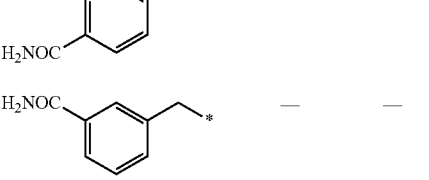 | 74 | 4.2 | 860 |
| 3-24 |  | — | — | 2200 |
| 4-1 | 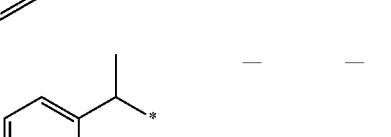 | 87 | — | 460 |
| 4-2 | 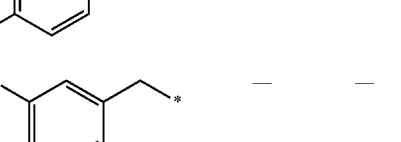 | — | — | 440 |
| 3-25 | 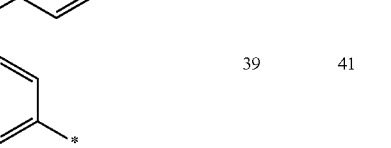 | 57 | 3.7 | 1100 |
| 3-26 |  | — | — | 2300 |
| 3-27 | NC, F (image not referenced) | — | — | 3000 |
| 3-28 | (phenyl) | 39 | 41 | 19000 |

TABLE 1-continued

Binding Affinity at 30 μM and $K_d$'s of the Thiadiazine DYRK1A Inhibitors

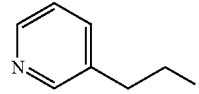

Figure 2:
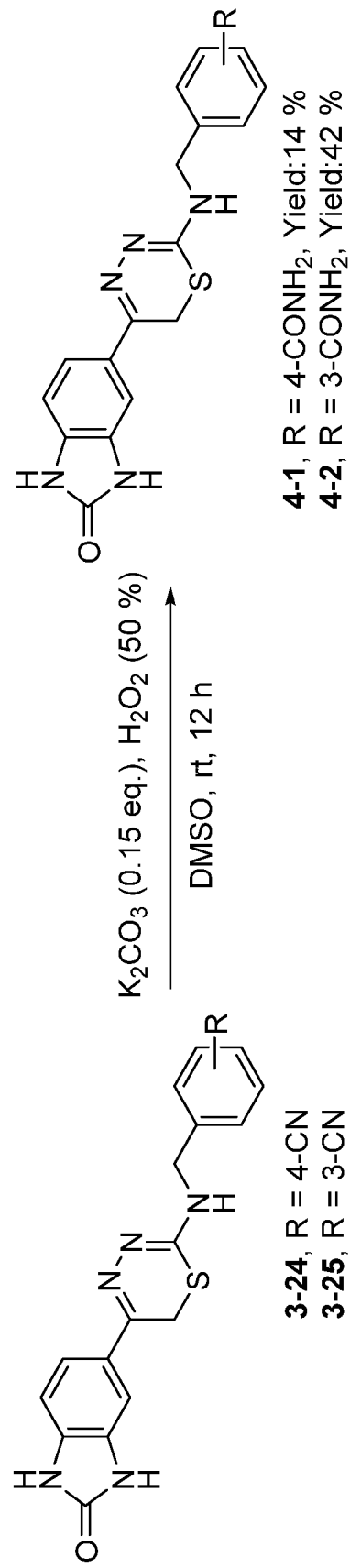
FIG. 2 is a schematic illustration showing the synthesis of 1,3,4-thiadiazine compound 4-1 and compound 4-2. Compounds 4-1 and 4-2 were prepared by partial hydrolysis of the corresponding cyano derivative using basic hydrogen peroxide solution as outlined in FIG. 2.

| Compound | R | Screening (30 μM) LifeTech[a] | Screening (30 μM) DiscoverX[b] | $K_d$ (nM)[c] |
|---|---|---|---|---|
| 3-29 | 3-F-C6H4- | — | — | 7000 |
| 3-30 | 3-CF3-C6H4- | — | — | 14000 |
| 3-31 | 3-CN-C6H4- | — | — | 3800 |
| 3-32 | 4-F-C6H4- | — | — | 16000 |
| 3-33 | 4-Cl-C6H4- | — | — | 7800 |
| 3-34 | PhCH2CH2- | 61 | 0.5 | 1600 |
| 3-35 | 4-F-C6H4-CH2CH2- | — | — | 15000 |
| 3-36 | 4-Cl-C6H4-CH2CH2- | — | — | 17000 |
| 3-37 | PhCH(CH3)- | — | — | 950 |
| 3-38 | 2-pyridyl-CH2CH2- | 87 | 8.4 | 1600 |
| 3-39 | 3-pyridyl-CH2CH2- | — | — | 2200 |
| 3-40 | 2-naphthyl-CH2- | 24 | 64 | n.d. |
| 3-41 | 1-naphthyl-CH2- | 11 | 36 | 7300 |
| 3-42 | 1-naphthyl- | 32 | 82 | n.d. | n.d. = not determined
[a] = % DYRK1A inhibition at 30 μM
[b] = Compounds were screened at 30 μM (n = 2), and results for primary screen binding interactions are reported as '% DMSO Ctrl', where lower values indicate stronger affinity
[c] = $K_d$ values are determined using eleven serial three fold dilutions (in duplicate)
[d] = Value in parenthesis is $IC_{50}$ determined at Life Technologies Compound 1 and its related neutral analogues (non-salt) were synthesized by following the synthetic protocol outlined in FIGS. 1-2 (Pfeiffer et al., "Unexpected Ring Enlargement of 2-Hydrazono-2,3-dihydro-1,3-thiazoles to 1,3,4-Thiadiazines," Helv. Chim. Acta 97(1):76-87 (2014), which is hereby incorporated by reference in its entirety). Acylation of commercially available 2-benzimidazole with chloroacetyl chloride in the presence of $AlCl_3$ gave compound 2 in 99% yield (PCT Publication No. WO 2002/050070 to Kornberg et al., which is hereby incorporated by reference in its entirety). Subsequently, the α-chloro ketone 2 underwent cyclo-condensation (Pfeiffer et al., "Unexpected Ring Enlargement of 2-Hydrazono-2,3-dihydro-1,3-thiazoles to 1,3,4-Thiadiazines," Helv. Chim. Acta 97(1):76-87 (2014), which is hereby incorporated by reference in its entirety) with purchased or synthesized thiosemicarbazides containing various R-groups to afford the desired thiadiazine analogues in range of 23-90% yield.

As shown in Table 1, the DYRK1A binding activity was found to be sensitive to the substitution pattern of the 2-benzylamino moiety. Notably, it was observed that the introduction of fluorobenzylamino (Compounds 3-12 to 3-14) and chlorobenzylamino (Compounds 3-15 to 3-17)

substituents at the 2-position of the thiadiazine improved the DYRK1A binding affinity of Compound 3-1 by 25- to 60-fold. Among these analogs, p-substituted benzylamino thiadiazines showed better DYRK1A binding compared to their respective o- and m-substituted benzylamino analogues. Specifically, Compounds 3-12 and 3-15 bearing p-chloro and p-fluorobenzylamino showed 24 to 60 fold improvement with $K_d$ of 185 nm and 71 nm, respectively, as compared to the original Compound 1 ($K_d$=7300 nM) and Compound 3-1 ($K_d$=4500 nm). However, in case of trifluoromethylbenzylamino (compounds 3-18 to 3-20) and cyano-substituted benzylamino thiadiazine analogues (Compounds 3-21 to 3-22), the improvement in binding activity was not as significant. Two exceptions are for m-trifluorobenzylamino thiadiazine (Compound 3-19) and m-cyanobenzylamino thiadiazine analogues (Compound 3-22) with $K_d$ of 660 and 320 nM, respectively, a 7-15-fold improvement in DYRK1A binding as compared to original hit Compound 3-1. For trifluoromethyl-substituted (Compounds 3-18 to 3-20) and cyano substituents, the m-substituted benzyl thiadiazines were significantly more potent than corresponding o- and p-substituted analogs. This SAR differs from that of halogen substituents, which showed improved DYRK1A binding for the p-substituted benzyl group as compared to their o- and m-analogs.

Figure 3:
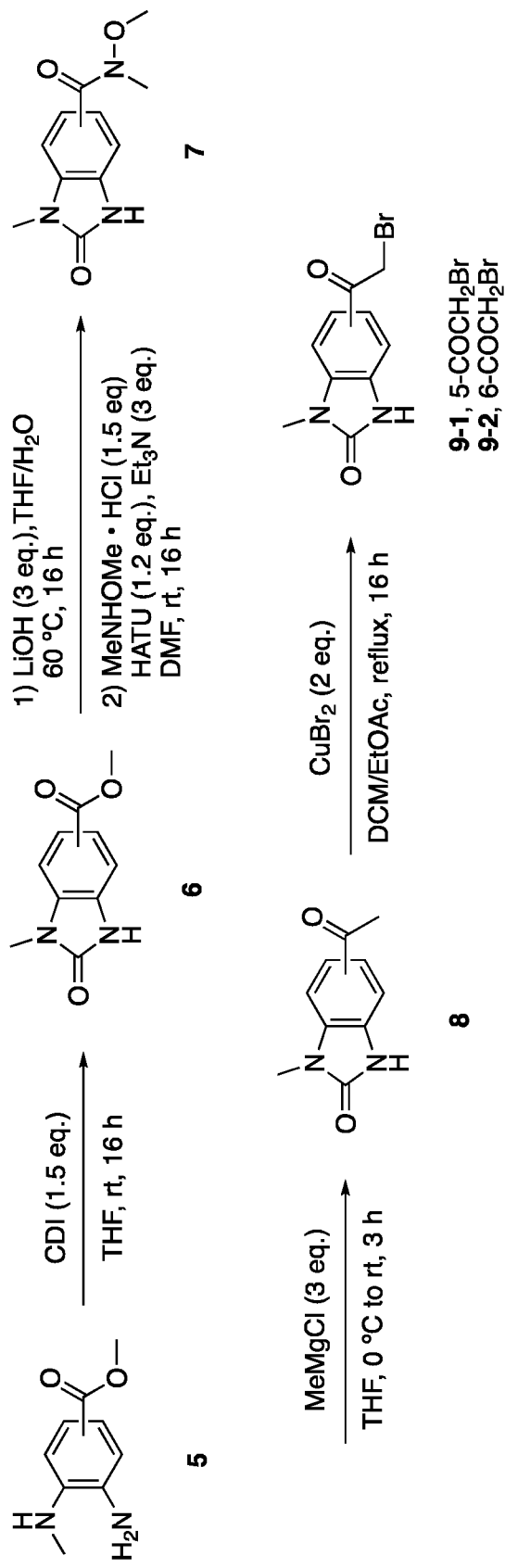
FIG. 3 is a schematic illustration showing the synthesis of 5- or 6-(2-bromoacetyl)-1-methyl-1H-benzo[d]imidazol-2 (3H)-one. Intermediate compounds 9-1 and 9-2 were synthesized by following the procedure in FIG. 3. CDI mediated cyclization of commercially available compound 5 furnished 1-methyl-1H-benzo[d]imidazol-2(3H)-one (compound 6). A methyl ester was hydrolyzed under basic condition to afford a free carboxylic acid which was then coupled with N,O-dimethylhydroxylamine to afford compound 7. The Weinreb-Nahm ketone synthesis of compound 7 yielded methyl ketone (compound 8). Bromination of compound 8 furnished intermediate compound 9.
Figure 4:
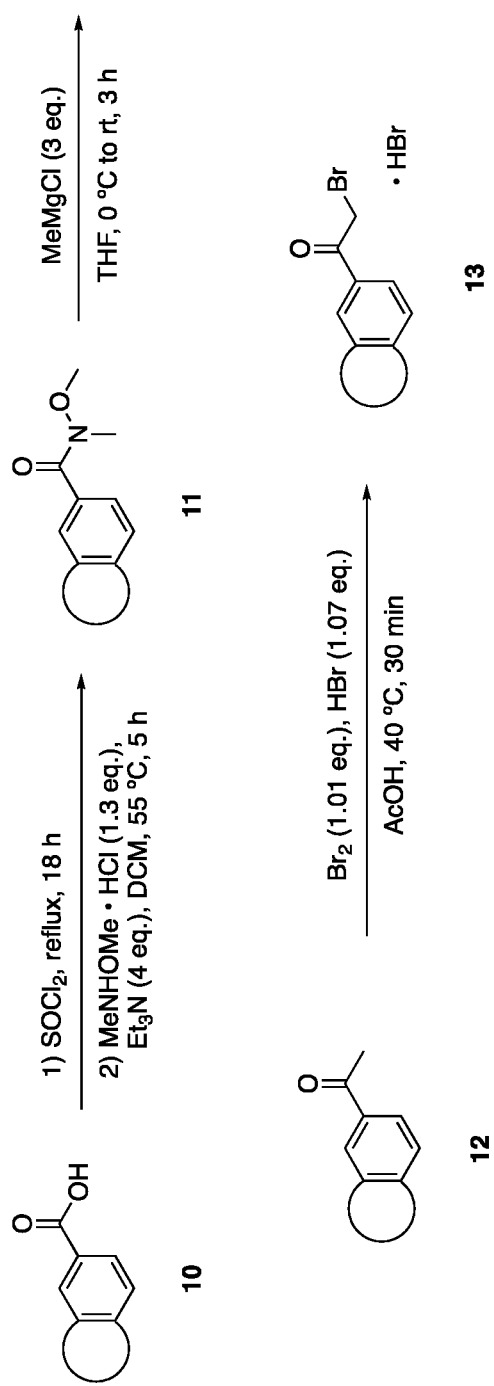
FIG. 4 is a schematic illustration showing the synthesis of α-bromoketone compounds 13. Various α-bromoketones 13 were synthesized from bromination of commercially available methyl ketones (compounds 12) or synthesized methyl ketone by following the scheme in FIG. 4.
Figure 5:
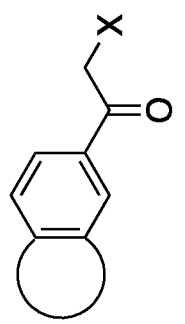
FIG. 5 is a schematic illustration showing the synthesis of 1,3,4-thiadiazine compound 14. The benzimidazolone group of thiadiazine analogue was modified following the general procedure for the synthesis of compound 3 by cyclo-condensation of intermediate compounds 9 or 13 with thiosemicarbazides to furnish compound 14.
Figure 5:
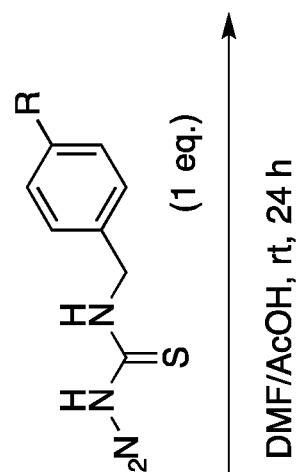
Figure 5:
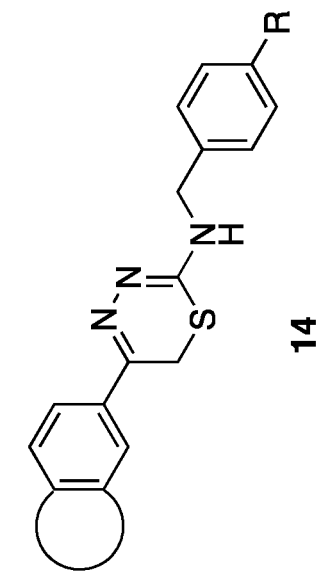

FIGS. 3-5 show the synthesis of various thiadiazine compounds and their intermediates. Tables 2 and 3 show the binding affinities of selected thiadiazine DYRK1 inhibitors.

TABLE 2

Binding Affinity at 10 μM and $K_d$'s of the Thiadiazine DYRK1A Inhibitors

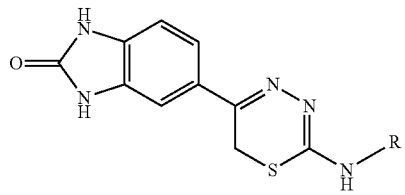

| Compound | R | Screening (10 μM) | $K_d$ (nM) |
|---|---|---|---|
| 3-43 | 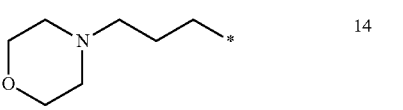 | 14 | — |
| 3-44 |  | 15 | — |
| 3-45 |  | 22 | — |
| 3-46 |  | 26 | — |
| 3-47 |  | 6.8 | 1400 |
| 3-48 | 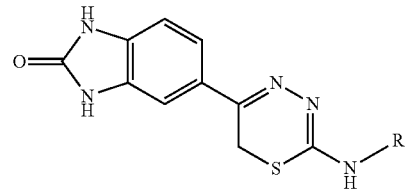 | 6.1 | 3700 |

TABLE 2-continued

Binding Affinity at 10 μM and $K_d$'s of the Thiadiazine DYRK1A Inhibitors

| Compound | R | Screening (10 μM) | $K_d$ (nM) |
|---|---|---|---|
| 3-49 |  | 7.8 | 4300 |
| 3-50 |  | 14 | — |
| 3-51 |  | 65 | — |
| 3-52 |  | 47 | — |
| 3-53 | 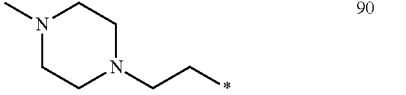 | 46 | — |
| 3-54 | 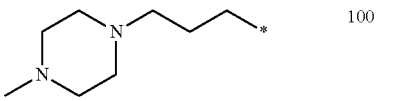 | 40 | — |
| 3-55 |  | 90 | — |
| 3-56 |  | 100 | — |
| 3-57 | 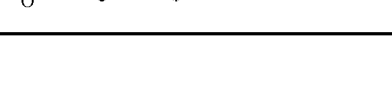 | 100 | — |
| 3-58 | | 9.5 | — |
| 3-59 | | 12 | — |

TABLE 3

Binding Affinity at 10 μM and $K_d$'s of the Thiadiazine DYRK1A Inhibitors

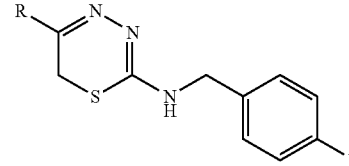

| Compound | R | R' | Screening (10 μM) | $K_d$ (nM) |
|---|---|---|---|---|
| 14-1 |  | F | — | 43000 |
| 14-2 | | H | — | 37000 |
| 14-3 | 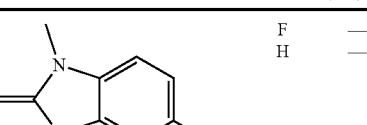 | F | — | 8800 |
| 14-4 | | H | — | 17000 |
| 14-5 | 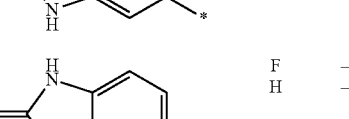 | F | 22 | 6800 |
| 14-6 | | H | 40 | — |
| 14-7 | 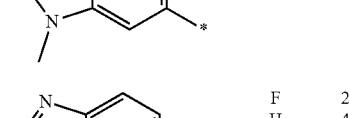 | F | 11 | 1200 |
| 14-8 | | H | 12 | — |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound of formula (I) having the following structure:

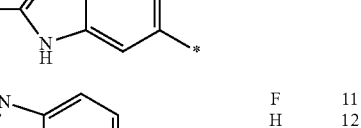

(I)

or a stereoisomer, pharmaceutically acceptable salt, oxide, or solvate thereof, wherein
$R^1$ is optionally present;
$R^1$, when present, and $R^2$ are independently selected at each occurrence thereof from H, $CH_3$, $CF_3$, halogen, and cyano;
X is selected from S, SO, and $SO_2$;
$R^3$ is selected from H, D, halogen, and $C_1$-$C_6$ substituted or unsubstituted alkyl;
Y is selected from a bond and branched or linear $C_1$-$C_6$ substituted or unsubstituted alkyl;
Z is selected from substituted or unsubstituted aryl, heteroaryl, cycloalkyl, alkyl, heterocycle, ether, amine, and sulfonyl;
$R^6$ is optionally present, and when present is oxo or $C_1$ alkyl; and
═══ is a single or double bond,
with the proviso that when $R^1$ and $R^2$ are both H, $R^3$ is H, X is S, and Y is $CH_2$, then Z cannot be phenyl.

2. The compound according to claim 1, wherein
$R^1$ and $R^2$ are H;
X is S; and
$R^3$ is H.

3. The compound according to claim 1, wherein Z is an unsubstituted phenyl ring or a phenyl ring substituted with a halogen, —$CF_3$, a nitrile, or —$CONH_2$.

4. The compound according to claim 1, wherein Z is selected from pyridinyl, cyclohexane, naphthalene, and morpholine.

5. The compound according to claim 1, wherein Y is selected from a bond, —$CH_2$—, —$CH(CH_3)$—, —$CH_2CH_2$—, —$CH_2CH(CH_3)$— and —$CH(CH_3)CH_2$—.

6. The compound according to claim 1, having the following structure:

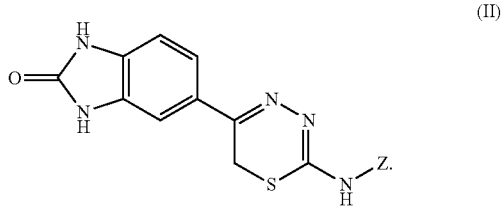

(II)

7. The compound according to claim 6, wherein Z is selected from

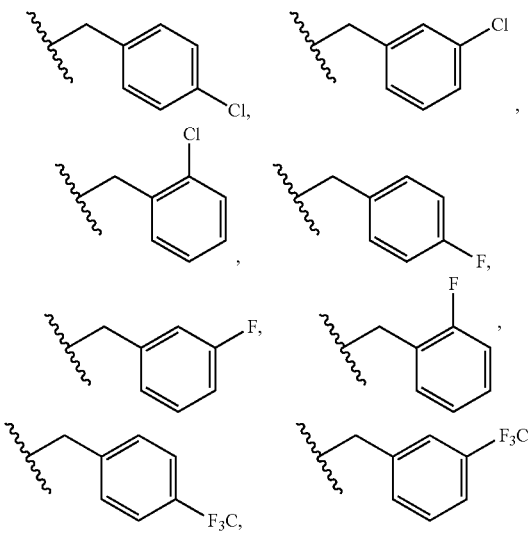

-continued

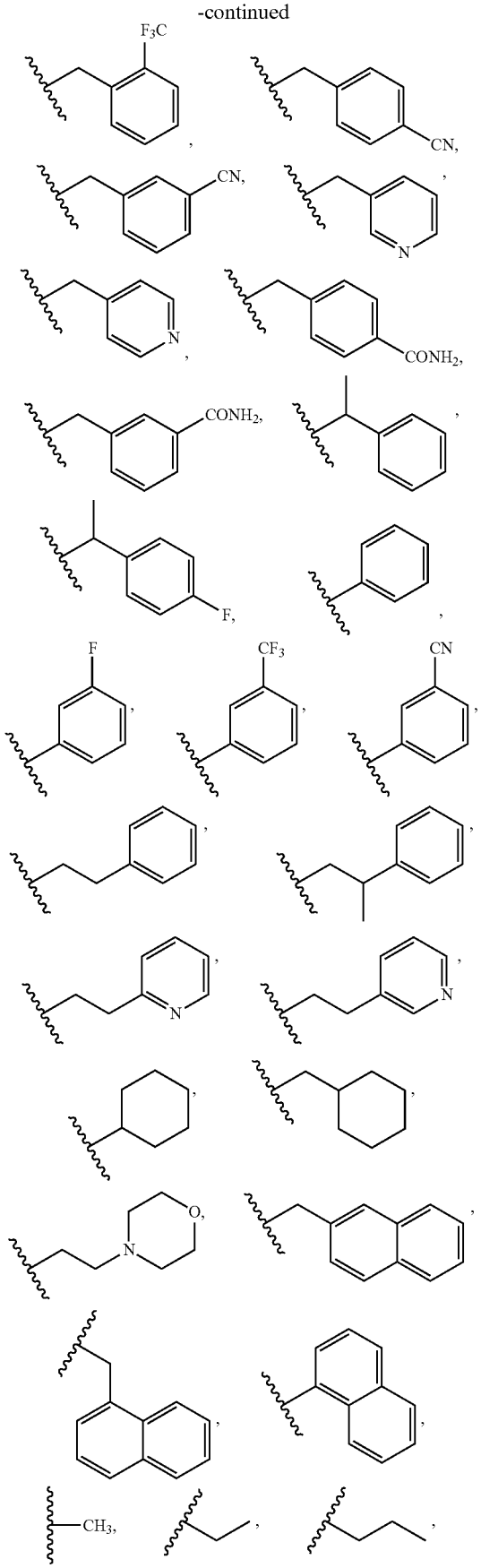

-continued

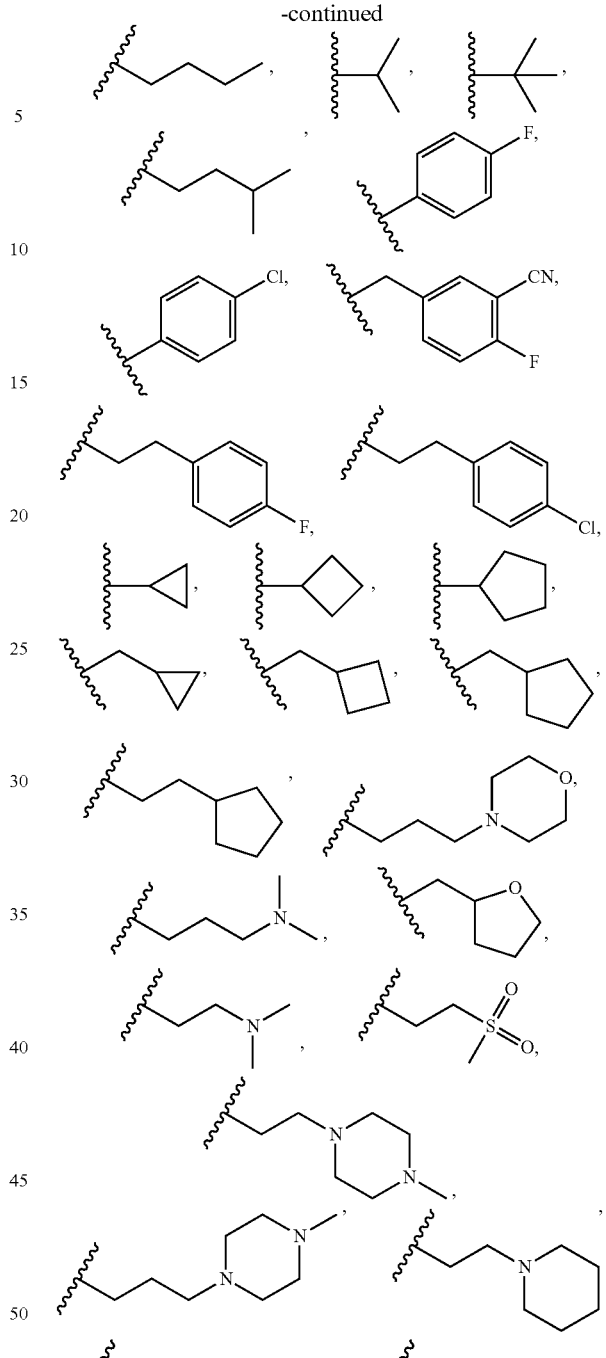

8. A method of inhibiting activity of a dual-specificity tyrosine phosphorylation-regulated kinase 1A (DYRK1A) in a cell, said method comprising:
 contacting the cell with a compound according to claim 1 under conditions effective to inhibit activity of the DYRK1A in the cell.

9. The method according to claim 8, wherein said method is carried out ex vivo.

10. The method according to claim 8, wherein said method is carried out in vivo.

11. A method of increasing cell proliferation in a population of pancreatic beta cells, said method comprising:

contacting a population of pancreatic beta cells with a compound according to claim 1 under conditions effective to increase cell proliferation in the population of pancreatic beta cells.

12. The method according to claim 11 further comprising:

contacting the population of pancreatic beta cells with a transforming growth factor beta (TGFβ) superfamily signaling pathway inhibitor.

13. A composition comprising:

a compound according to claim 1 and a carrier.

14. The composition according to claim 13 further comprising:

a transforming growth factor beta (TGFβ) superfamily signaling pathway inhibitor.

15. The composition according to claim 13, wherein the carrier is a pharmaceutically-acceptable carrier.

16. A method for the treatment of a condition associated with insufficient insulin secretion, said method comprising:

administering to a subject in need of treatment of a condition associated with insufficient insulin secretion a compound of claim 1 under conditions effective to treat the subject for the condition.

17. The method according to claim 16 further comprising:

administering a transforming growth factor beta (TGFβ) superfamily signaling pathway inhibitor.

* * * * *